(12) United States Patent
Martinis et al.

(10) Patent No.: US 7,785,827 B2
(45) Date of Patent: Aug. 31, 2010

(54) METHOD AND COMPOSITION FOR LEUCYL-TRNA SYNTHETASES AND DERIVATIVES THEREOF THAT ACTIVATE AND AMINOACYLATE NON-LEUCINE AMINO ACID TO TRNA ADAPTOR MOLECULES

(75) Inventors: Susan A. Martinis, Houston, TX (US); James M. Briggs, Katy, TX (US); Richard S. Mursinna, Houston, TX (US); Keun Woo Lee, Houston, TX (US); Tommie L. Lincecum, Houston, TX (US); Amy M. Williams, Houston, TX (US); Yuxin Zhai, Houston, TX (US)

(73) Assignee: University of Houston System, Houston, TX (US)

( * ) Notice: Subject to any disclaimer, the term of this patent is extended or adjusted under 35 U.S.C. 154(b) by 716 days.

(21) Appl. No.: 10/251,648

(22) Filed: Sep. 20, 2002

(65) Prior Publication Data
US 2004/0203094 A1 Oct. 14, 2004

Related U.S. Application Data

(60) Provisional application No. 60/323,582, filed on Sep. 20, 2001.

(51) Int. Cl.
C07K 14/47 (2006.01)
C07H 21/04 (2006.01)
C12P 21/06 (2006.01)
(52) U.S. Cl. .................. 435/69.1; 435/183; 435/320.1; 536/23.5
(58) Field of Classification Search ........................ None
See application file for complete search history.

(56) References Cited

OTHER PUBLICATIONS

Mursinna et al A Conserved Threonine within *Escherishia coli* Leucyl-tRNA Synthetase Prevents Hydrolytic Editing of Leucyl-tRNALeu Biochemistry 2001, 40, 5376-5381.*
Chen et al (CPI Domain in *Escherichia coli* Leucyl-tRNA Synthetase Is Crucial for Its Editing Function, Biochemistry 2000, 39, 6726-6731.*
Hohmann, S., and Thevelein, J. M., The Cell Division Cycle Gene CDC60 Encodes Cytosolic Leucyl-tRNA Synthetase in Saccharomyces Cerevisiae, Gene 120, pp. 43-49, 1992.
Apostol, I., J. Levine, J. Lippincott, J. Leach, E. Hess, C.B. Glascock, M. Weickert, and R. Blackmore. 1997. Incorporation of norvaline at leucine positions in recombinant human hemoglobin expressed in *Escherichia coli*. J Biol Chem 272: 28980-28988.
Asahara, H., H. Himeno, K. Tamura, T. Hasegawa, K. Watanabe, and M. Shimizu. 1993. Recognition nucleotides of *Escherichia coli* tRNALeu and its elements facilitating discrimination from tRNASer and tRNATyr. J. Mol. Biol. 231:219-229.
Asahara, H., N. Nameki, and T. Hasegawa. 1998. In vitro selection of RNAs aminoacylated by *Escherichia coli* leucyl-tRNA synthetase. J Mol Biol 283:605-18.
Baldwin, A. N., and Berg, P. 1966. Transfer ribonucleic acid-induced hydrolysis of valyladenylate bound to isoleucyl ribonucleic acid synthetase. J Biol Chem 241, 839-845.
Chen, J. F., N. N. Guo, T. Li, E. D. Wang, and Y. L. Wang. 2000. CP1 domain in *Escherichia coli* leucyl-tRNA synthetase is crucial for its editing function. Biochemistry 39:6726-31.
Chen, J. F., Li, T., Wang, E. D., and Wang, Y. L. 2001. Effect of alanine-293 replacement on the activity, ATP binding, and editing of *Escherichia coli* leucyl-tRNA synthetase. Biochemistry 40, 1144-1149.
Cornish, V., K. Hahn, and P. Schultz. 1996. Site-specific protein modification using a ketone handle. J. Am. Chem. Soc. 118:8150-8151.
Cusack, S., A. Yaremchuk, and M. Tukalo. 2000. The 2 Å crystal structure of leucyl-tRNA synthetase and its complex with a leucyl-adenylate analogue. EMBO J 19:2351-2361.
Dietrich, A., P. Romby, L. Marechal-Drouard, P. Guillemaut, and R. Giegé. 1990. Solution conformation of several free tRNALeu species from bean, yeast and *Escherichia coli* and interaction of these tRNAs with bean cytoplasmic leucyl-tRNA synthetase. A phosphate alkylation study with ethylnitrosourea. Nucl. Acids Res. 18:2589-2597.
Doring, V., H. D. Mootz, L. A. Nangle, T. L. Hendrickson, V. de Crecy-Lagard, P. Schimmel, and P. Marliere. 2001. Enlarging the amino acid set of *Escherichia coli* by infiltration of the valine coding pathway. Science 292:501-4.
Englisch, S., Englisch, U., von der Haar, F., and Cramer, F. 1986. The proofreading of hydroxy analogues of leucine and isoleucine by leucyl-tRNA synthetases from *E. coli* and yeast. Nucleic Acids Res 14, 7529-7539.
Fersht, A. R. 1977. Editing mechanisms in protein synthesis. Rejection of valine by the isoleucyl-tRNA synthetase. Biochemistry 16, 1025-1030.
Fukai, S., Nureki, O., Sekine, S., Shimada, A., Tao, J., Vassylyev, D. G., and Yokoyama, S. 2000. Structural basis for double-sieve discrimination of L-valine from L- isoleucine and L-threonine by the complex of tRNA(Val) and valyl-tRNA synthetase. Cell 103, 793-803.
Giegé, R., M. Sissler, and C. Florentz. 1998. Universal rules and idiosyncratic features in tRNA identity. Nucl. Acids. Res. 26:5017-35.

(Continued)

*Primary Examiner*—Manjunath N Rao
*Assistant Examiner*—Kagnew H Gebreyesus
(74) *Attorney, Agent, or Firm*—Monique Vander Molen; Jennifer Sickler; Gardere Wynne Sewell LLP

(57) ABSTRACT

A method and composition for tRNA synthetases that activate and aminoacylate nonstandard and noncognate amino acids to tRNA adaptor molecules is described that can be used to generate custom designed protein products for uses in medicinal, therapeutic, diagnostic, biotechnology, engineering, and spectroscopy applications. Some tRNA synthetases naturally misactivate and misaminoacylate noncognate amino acids. Many of these tRNA synthetases, including but not limited to leucyl-, isoleucyl-, and valyl-tRNA synthetases, have evolved proofreading and editing mechanisms to correct these mistakes. Inactivation of the enzyme's editing activity allows and facilitates production and accumulation of tRNAs that are misaminoacylated with nonstandard and noncognate amino acids. These misaminoacylated tRNAs can be used to introduce novel amino acids into proteins.

29 Claims, 51 Drawing Sheets

OTHER PUBLICATIONS

Heckler, T. G., L. H. Chang, Y. Zama, T. Naka, M. S. Chorghade, and S. M. Hecht. 1984. T4 RNA ligas mediated preparation of novel "chemically misacylated" tRNAPheS. Biochemistry 23:1468-73.

Hendrickson, T. L., T. K. Nomanbhoy, and P. Schimmel. 2000. Errors from selective disruption of the editing center in a tRNA synthetase. Biochemistry 39:8180-6.

Higgins, D. G., Thompson, J. D., and Gibson, T. J. 1996. Using CLUSTAL for multiple sequence alignments. Methods Enzymol 266, 383-402.

Kiick, K. L., J. C. van Hest, and D. A. Tirrell. 2000. Expanding the Scope of Protein Biosynthesis by Altering the Methionyl-tRNA Synthetase Activity of a Bacterial Expression Host Angew Chem Int Ed Engl 39:2148-2152.

Kiick, K. L., R. Weberskirch, and D. A. Tirrell. 2001. Identification of an expanded set of translationally active methionine analogues in *Escherichia coli*. FEBS Lett 502:25-30.

Lee, K. W., J.M. Briggs. 2002 Molecular Modeling Study of the Editing Activity of *Escherichia coli* Leucyl-tRNA Synthetase: Two Amino Acid Binding Sites in the editing domain., Proteins: Str. Function Gen., in press.

Lee, N., and H. Suga. 2001. A minihelix-loop RNA acts as a trans-aminoacylation catalyst. Rna 7:1043-51.

Lin, L., S. P. Hale, and P. Schimmel. 1996. Aminoacylation error correction. Nature 384:33-34.

Lincecum, T. L., and S. A. Martinis. 2000. The tRNA synthetase proofreading and editing active sites: A novel antibiotic target. SAAS Bulletin Biochem. Biotech. 13:25-33.

Liu, D. R., T. J. Magliery, M. Pastrnak, and P. G. Schultz. 1997a. Engineering a tRNA and aminoacyl-tRNA synthetase for the site-specific incorporation of unnatural amino acids into proteins in vivo. Proc Natl Acad Sci U S A 94:10092-7.

Liu, D. R., T. J. Magliery, and P. G. Schultz. 1997b. Characterization of an 'orthogonal' suppressor tRNA derived from *E. coli* tRNA2(Gln). Chem Biol 4:685-91.

Lohse, P. A., and J. W. Szostak. 1996. Ribozyme-catalysed amino-acid transfer reactions. Nature 381:442-4.

Martinis, S. A., and P. Schimmel. 1992. Enzymatic Aminoacylation of Sequence-Specific RNA Minihelices and Hybrid Duplexes with Methionine. Proc. Natl. Acad. Sci. U. S. A. 89:65-69.

Martinis, S. A., and P. Schimmel. 1996. Aminoacyl tRNA Synthetases: General Structures and Relationships., p. 887-901. In F. C. Neidhardt (ed.), *Escherichia coli* and *Salmonella* Cellular and Molecular Biology, 2nd Ed. ASM Press, Washington D. C.

Martinis, S. A., and G. E. Fox. 1997. Non-standard amino acid recognition by *Escherichia coli* leucyl-tRNA synthetase. Nucleic Acids Symp Ser 36:125-8.

Martinis, S. A., P. Plateau, J. Cavarelli, and C. Florentz. 1999a. Aminoacyl-tRNA Synthetases: A Family of Expanding Functions. EMBO J. 18:4591-4596.

Martinis, S. A., P. Plateau, J. Cavarelli, and C. Florentz. 1999b. Aminoacyl-tRNA Synthetases: A New Image for a Classical Family, Biochimie 81:683-700.

Mendel, D., V. W. Cornish, and P. G. Schultz. 1995. Site-directed mutagenesis with an expanded genetic code. Annu Rev Biophys Biomol Struct 24:435-62.

Mursinna, R. S., T. L. Lincecum, Jr., and S. A. Martinis. 2001. A conserved threonine within *Escherichia coli* leucyl-tRNA synthetase prevents hydrolytic editing of leucyl-tRNALeu. Biochemistry 40:5376-81.

Mursinna, R.S. and S.A. Martinis. 2002. Rational Design to Block Amino Acid Editing of a tRNA Synthetase. J. Am. Chem. Soc. 124:7286-7287.

Niemz, A., and D. A. Tirrell. 2001. Self-association and membrane-binding behavior of melittins containing trifluoroleucine. J Am Chem Soc 123:7407-13.

Noren, C. J., S. J. Anthony-Cahill, M. C. Griffith, and P. G. Schultz. 1989. A general method for site-specific incorporation of unnatural amino acids into proteins. Science 244:182-8.

Normanly, J., R. C. Ogden, S. J. Horvath, and J. Abelson. 1986. Changing the Identity of a Transfer RNA. Nature 321:213-219.

Norris, A. T., and Berg, P. 1964. Mechanism of aminoacyl RNA synthesis: studies with isolated aminoacyl adenylate complexes of isoleucyl RNA synthetase. Biochemistry 52: 330-337.

Nureki, O., D. G. Vassylyev, M. Tateno, A. Shimada, T. Nakama, S. Fukai, M. Konno, T. L. Hendrickson, P. Schimmel, and S. Yokoyama. 1998. Enzyme structure with two catalytic sites for double-sieve selection of substrate Science 280:578-582.

Nureki, O., D. G. Vassylyev, M. Tateno, A. Shimada, T. Nakama, S. Fukai, M. Konno, T. L. Hendrickson, P. Schimmel, and S. Yokoyama. 1999. Proofreading by isoleucyl-tRNA synthetase: response. Science 283:453.

Payne, R. C., B. P. Nichols, and S. M. Hecht. 1987. *Escherichia coli* tryptophan synthase: synthesis of catalytically competent alpha sub-unit in a cell-free system containing preacylated tRNAs. Biochemistry 26:3197-205.

Rennert, O., and H. Anker. 1963. On the incorporation of 5', 5', 5'—trifluoroleucine into proteins of *E. coli*. Biochemistry 3:471-476.

Saito, H., and H. Suga. 2001. A Ribozyme Exclusively Aminoacylates the 3'-Hydroxyl Group of the tRNA Terminal Adenosine. J Am Chem Soc 123:7178-9.

Sampson, J. R., and Uhtenbeck, O. C. 1988. Biochemical and physical characterization of an unmodified yeast phenylalanine transfer RNA transcribed in vitro. Proc. Natl. Acad. Sci., U. S. A. 85, 1033-1037.

Schimmel, P., and Schmidt, E. 1995. Making connections: RNA-dependent amino acid recognition. Trends Biochem Sci 20, 1-2.

Schimmel, P., and D. Soll. 1997. When protein engineering confronts the tRNA world. Proc Natl Acad Sci U S A 94:10007-9.

Sharma, N., R. Furter, P. Kast, and D. A. Tirrell. 2000. Efficient introduction of aryl bromide functionality into proteins in vivo. FEBS Lett 467:37-40.

Starzyk, R. M., T. A. Webster, and P. Schimmel. 1987. Evidence for dispensable sequences inserted into a nucleotide fold. Science 237:1614-1618.

Suga, H., J. A. Cowan, and J. W. Szostak. 1998a. Unusual metal ion catalysis in an acyl-transferase ribozyme. Biochemistry 37:10118-25.

Suga, H., P. A. Lohse, and J. W. Szostak. 1998b. Structural and kinetic characterization of an acyl transferase ribozyme. J. Am. Chem. Soc. 120:1151-1156.

Szostak, J. W. 1992. In vitro Genetics. Trends Biochem. Sci. 17:89-93.

Tang, Y., G. Ghirlanda, W. A. Petka, T. Nakajima, W. F. DeGrado, and D. A. Tirrell. 2001a. Fluorinated Colled-Coil Proteins Prepared In Vivo Display Enhanced Thermal and Chemical Stability This work was supported by a grant from the U.S. Army Research Office. Angew Chem Int Ed Engl 40:1494-1496.

Tang, Y., G. Ghirlanda, N. Vaidehi, J. Kua, D. T. Mainz, I. W. Goddard, W. F. DeGrado, and D. A. Tirrell. 2001b. Stabilization of coiled-coil peptide domains by introduction of trifluoroleucine. Biochemistry 40:2790-6.

Tang, Y., and D. A. Tirrell. Attenuation of the Editing Activity of the *Escherichia coli* Leucyl-tRNA Synthetase Allows Incorporation of Novel Amino Acids into Proteins in Vivo, Biochemistry 2002:41:10635-10645.

Thompson, J. D., D. G. Higgins, and T. J. Gibson. 1994. CLUSTAL W: Improving the sensitivity of progressive multiple sequence alignment through sequence weighting, positions-specific gap penalties, and weight matrix choice. Nucl. Acids Res. 22:4673-4680.

Tuerk, C., and L. Gold. 1990. Systematic Evolution of Ligands by Exponential Enrichment: RNA Ligands to Bacteriophage T4 DNA Polymerase. Science 249:505-510.

Varshney, U., C.-P. Lee, and U. L. RajBhandary. 1991. Direct Analysis of Aminoacylation Levels of tRNAs in vivo: Application to Studying Recognition of *E. coli* Initiator tRNA Mutants by Glutaminyl-tRNA Synthetase. J. Biol. Chem. 266:24712-24718.

Wang, L., A. Brock, B. Herberich, and P. G. Schultz. 2001. Expanding the genetic cde of *Escherichia coli*. Science 292:498-500.

\* cited by examiner

```
              A A A   A A
          243 ↓ ↓ ↓   ↓ ↓                 264
Ec  LeuRS  L T V Y T T R P D T F M G C T Y L A V A A G   SEQ ID NO.:42
Tt  LeuRS  I P V F T T R P D T L F G A T F L V L A P E   SEQ ID NO.:43
Bs  LeuRS  F T V F T T R P D T L F G A T Y T V L A P E   SEQ ID NO.:44
Scm LeuRS  L I V F T T R P E T L F A V Q Y V A L A L D   SEQ ID NO.:45

217                              238
Ec  ValRS  L V V A T T R P E T L L G D T G V A V N P E   SEQ ID NO.:46
Bs  ValRS  I E I A T T R P E T M L G D T A V A V H P E   SEQ ID NO.:47
Bst ValRS  I E V A T T R P E T M L G D T A V A V H P D   SEQ ID NO.:48

237                              258
Ec  IleRS  L V I W T T T P W T L P A N R A I S I A P D   SEQ ID NO.:49
Tt  IleRS  L L I W T T T P W T L P G N V A A V H P E   SEQ ID NO.:50
Sa  IleRS  F I I W T T T P W T I P S N V A I T V H P E   SEQ ID NO.:51
```

Figure 2

A. Cognate Leucine Bound to Wild-type and T252A Mutant CP1
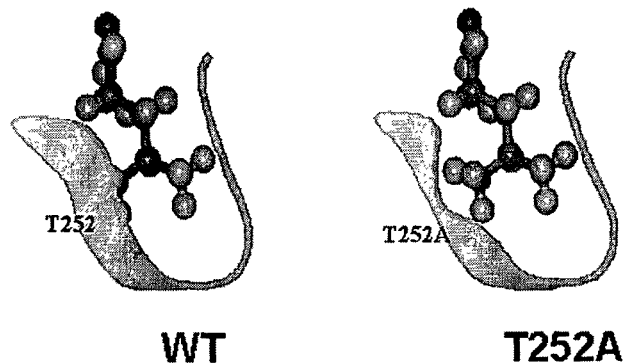
WT          T252A
B. CP1 Amino Acid Substrate Binding Pocket
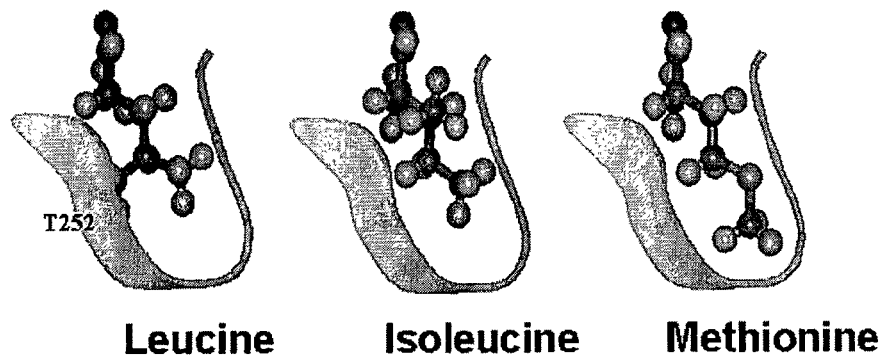
Leucine     Isoleucine     Methionine
Figure 6

```
                        A           A      AA   AA
                        ↓           ↓      ↓↓   ↓↓
ScL-cyt  404  K G T G - - V V T C V P S N S P D D Y I T T K D L L H K   SEQ ID NO.:52
CeL-cyt       K G T G - - V V T S V P S D S P D D F A A L S D L K K K   SEQ ID NO.:53
NcL-cyt       K G T G - - V V T S V P S D S P D D C A M M T E L A K K   SEQ ID NO.:54
HsL-cyt       K G T G - - V V T S V P S D S P D D I A A L R D L K K K   SEQ ID NO.:55

EcL      330  Y G T G - - A V M A V P G H D Q R D Y E F - - A S K Y G   SEQ ID NO.:56
TtL           Y G T G - - A I M A V P A H D Q R D Y E F - - A R K F G   SEQ ID NO.:57
BsL           Y G T G - - A V M A V P G H D E R D F E F - - A K T F G   SEQ ID NO.:58
ScL-mit       Y G S A P S A V M G C P G H D N R D F E F W Q T N C P G   SEQ ID NO.:59

EcV      222  K G T G - - C V K I T P A H D F N D Y E V - - G K R H A   SEQ ID NO.:60
BsV           F G S G - - A V K I T P A H D P N D F E L - - G N R H N   SEQ ID NO.:61
BstV          F G S G - - A V K I T P A H D P N D F E I - - G N R H N   SEQ ID NO.:62

EcI      262  A G T G - - A V H T A P G H G P D D Y V I - - G Q K Y G   SEQ ID NO.:63
TtI           D G T G - - I V H Q A P A F G A E D L E T - - A R V Y G   SEQ ID NO.:64
SaI           E G T G - - I V H I A P A H G E D D Y Q L - - V L E R D   SEQ ID NO.:65
```

Figure 12

```
                           A    A
                           ↓    ↓
EcL       330  YGTG--AVMAVPGHDQRDYEF--ASK
TtL            YGTG--AIMAVPAHDQRDYEF--ARK
BsL            YGTG--AVMAVPGHDERDFEF--AKT
ScL-mit        YGSAPSAVMGCPGHDNRDFEFWQTNC
BsV            FGSG--AVKITPAHDPNDFEL--GNR
GsV            FGSG--AVKITPAHDPNDFEI--GNR
EcV       222  KGTG--CVKITPAHDFNDYEV--GKR
```

Figure 50

SEQUENCE LISTING

<160> NUMBER OF SEQ ID NOS: 65

<210> SEQ ID NO 1
<211> LENGTH: 32
<212> TYPE: DNA
<213> ORGANISM: artificial
<220> FEATURE:
<223> OTHER INFORMATION: oligo

<400> SEQUENCE: 1
ctacccgccc ggacgccttt atgggttgta cc                32

<210> SEQ ID NO 2
<211> LENGTH: 32
<212> TYPE: DNA
<213> ORGANISM: artificial
<220> FEATURE:
<223> OTHER INFORMATION: oligo

<400> SEQUENCE: 2
gatgggcggg cctgcggaaa tacccaacat gg                32

<210> SEQ ID NO 3
<211> LENGTH: 16
<212> TYPE: DNA
<213> ORGANISM: artificial
<220> FEATURE:
<223> OTHER INFORMATION: oligo

<400> SEQUENCE: 3
cgaaggcgtg gagatc                                  16

<210> SEQ ID NO 4
<211> LENGTH: 28
<212> TYPE: DNA
<213> ORGANISM: artificial
<220> FEATURE:
<223> OTHER INFORMATION: oligo

<400> SEQUENCE: 4
gcgcccggac ttctttatgg gttgtacc                     28

<210> SEQ ID NO 5
<211> LENGTH: 30
<212> TYPE: DNA
<213> ORGANISM: artificial
<220> FEATURE:
<223> OTHER INFORMATION: oligo

<400> SEQUENCE: 5
gggtacaacc cataaagaag tccgggcggg                   30

<210> SEQ ID NO 6
<211> LENGTH: 17
<212> TYPE: DNA
<213> ORGANISM: artificial
<220> FEATURE:
<223> OTHER INFORMATION: oligo

<400> SEQUENCE: 6

-continued

```
ccgaaggcgt ggagatc                                                    17

<210> SEQ ID NO 7
<211> LENGTH: 27
<212> TYPE: DNA
<213> ORGANISM: artificial
<220> FEATURE:
<223> OTHER INFORMATION: oligo

<400> SEQUENCE: 7
cccgcccgga ctactttatg ggttgta                                         27

<210> SEQ ID NO 8
<211> LENGTH: 29
<212> TYPE: DNA
<213> ORGANISM: artificial
<220> FEATURE:
<223> OTHER INFORMATION: oligo

<400> SEQUENCE: 8
ggtacaaccc ataaagtagt ccgggcggg                                       29

<210> SEQ ID NO 9
<211> LENGTH: 63
<212> TYPE: DNA
<213> ORGANISM: artificial
<220> FEATURE:
<223> OTHER INFORMATION: oligo

<400> SEQUENCE: 9
ggtttgtgca acaagtcctt ggtggtaatg taggcatctg gtgaattaga tggtacacac     60
gtg                                                                   63

<210> SEQ ID NO 10
<211> LENGTH: 63
<212> TYPE: DNA
<213> ORGANISM: artificial
<220> FEATURE:
<223> OTHER INFORMATION: oligo

<400> SEQUENCE: 10
cacgtgtgta ccatctaatt caccagatgc ctaccataca tccaaggact tgttgcacaa     60
acc                                                                   63

<210> SEQ ID NO 11
<211> LENGTH: 27
<212> TYPE: DNA
<213> ORGANISM: artificial
<220> FEATURE:
<223> OTHER INFORMATION: oligo

<400> SEQUENCE: 11
ggtaccgggg cacgcccagc gcgacta                                         27

<210> SEQ ID NO 12
<211> LENGTH: 27
<212> TYPE: DNA
<213> ORGANISM: artificial
<220> FEATURE:
<223> OTHER INFORMATION: oligo

<400> SEQUENCE: 12
ccatggcccc gtgcgggtcg cgctgat                                         27
```

-continued

```
<210> SEQ ID NO 13
<211> LENGTH: 30
<212> TYPE: DNA
<213> ORGANISM: artificial
<220> FEATURE:
<223> OTHER INFORMATION: oligo

<400> SEQUENCE: 13
gggcacgacc agcgcgccta cgagtttgcc                                         30

<210> SEQ ID NO 14
<211> LENGTH: 30
<212> TYPE: DNA
<213> ORGANISM: artificial
<220> FEATURE:
<223> OTHER INFORMATION: oligo

<400> SEQUENCE: 14
ggcaaactcg taggcgcgct ggtcgtgccc                                         30

<210> SEQ ID NO 15
<211> LENGTH: 36
<212> TYPE: DNA
<213> ORGANISM: artificial
<220> FEATURE:
<223> OTHER INFORMATION: oligo

<400> SEQUENCE: 15
ggtaccgggg cacgcccagc gcgcctacga gtttgc                                  36

<210> SEQ ID NO 16
<211> LENGTH: 36
<212> TYPE: DNA
<213> ORGANISM: artificial
<220> FEATURE:
<223> OTHER INFORMATION: oligo

<400> SEQUENCE: 16
ggcaaactcg taggcgcgct gggcgtgccc cggtac                                  36

<210> SEQ ID NO 17
<211> LENGTH: 30
<212> TYPE: DNA
<213> ORGANISM: artificial
<220> FEATURE:
<223> OTHER INFORMATION: oligo

<400> SEQUENCE: 17
gggcacgacc agcgcgccta cgagtttgcc                                         30

<210> SEQ ID NO 18
<211> LENGTH: 30
<212> TYPE: DNA
<213> ORGANISM: artificial
<220> FEATURE:
<223> OTHER INFORMATION: oligo

<400> SEQUENCE: 18
ggcaaactcg taggcgcgct ggtcgtgccc                                         30

<210> SEQ ID NO 19
<211> LENGTH: 29
<212> TYPE: DNA
<213> ORGANISM: artificial
<220> FEATURE:
<223> OTHER INFORMATION: oligo
```

-continued

```
<400> SEQUENCE: 19
cccgcccgga ctactttatg ggttgtacc                                           29

<210> SEQ ID NO 20
<211> LENGTH: 14
<212> TYPE: DNA
<213> ORGANISM: artificial
<220> FEATURE:
<223> OTHER INFORMATION: oligo

<400> SEQUENCE: 20
gaaggcgtgg agat                                                           14

<210> SEQ ID NO 21
<211> LENGTH: 42
<212> TYPE: DNA
<213> ORGANISM: artificial
<220> FEATURE:
<223> OTHER INFORMATION: oligo

<400> SEQUENCE: 21
gaagtattac tgcctgtcta gccttcccta tccttctggt cg                            42

<210> SEQ ID NO 22
<211> LENGTH: 42
<212> TYPE: DNA
<213> ORGANISM: artificial
<220> FEATURE:
<223> OTHER INFORMATION: oligo

<400> SEQUENCE: 22
cgaccagaag gatagggaag gctagacagg cagtaatact tc                            42

<210> SEQ ID NO 23
<211> LENGTH: 18
<212> TYPE: DNA
<213> ORGANISM: artificial
<220> FEATURE:
<223> OTHER INFORMATION: oligo

<400> SEQUENCE: 23
gttgtcgtac gtccacgg                                                       18

<210> SEQ ID NO 24
<211> LENGTH: 32
<212> TYPE: DNA
<213> ORGANISM: artificial
<220> FEATURE:
<223> OTHER INFORMATION: oligo

<400> SEQUENCE: 24
cttcgtattg atggaggccg gcacgggcgc ag                                       32

<210> SEQ ID NO 25
<211> LENGTH: 32
<212> TYPE: DNA
<213> ORGANISM: artificial
<220> FEATURE:
<223> OTHER INFORMATION: oligo

<400> SEQUENCE: 25
gaagcataac tacctccggc cgtgcccgcg tc                                       32

<210> SEQ ID NO 26
<211> LENGTH: 17
```

<212> TYPE: DNA
<213> ORGANISM: artificial
<220> FEATURE:
<223> OTHER INFORMATION: oligo

<400> SEQUENCE: 26
cggctctgag ccagatc                                                    17

<210> SEQ ID NO 27
<211> LENGTH: 35
<212> TYPE: DNA
<213> ORGANISM: artificial
<220> FEATURE:
<223> OTHER INFORMATION: oligo

<400> SEQUENCE: 27
gccacgttga gaccggaata tatgtatgga caaac                                35

<210> SEQ ID NO 28
<211> LENGTH: 35
<212> TYPE: DNA
<213> ORGANISM: artificial
<220> FEATURE:
<223> OTHER INFORMATION: oligo

<400> SEQUENCE: 28
gtttgtccat acatatattc cggtctcaac gtggc                                35

<210> SEQ ID NO 29
<211> LENGTH: 27
<212> TYPE: DNA
<213> ORGANISM: artificial
<220> FEATURE:
<223> OTHER INFORMATION: oligo

<400> SEQUENCE: 29
ggtgttacac cacaagaata tattggt                                         27

<210> SEQ ID NO 30
<211> LENGTH: 34
<212> TYPE: DNA
<213> ORGANISM: artificial
<220> FEATURE:
<223> OTHER INFORMATION: oligo

<400> SEQUENCE: 30
cacgtgtgta ccatctgctt caccagatga ctac                                 34

<210> SEQ ID NO 31
<211> LENGTH: 34
<212> TYPE: DNA
<213> ORGANISM: artificial
<220> FEATURE:
<223> OTHER INFORMATION: oligo

<400> SEQUENCE: 31
gtagtcatct ggtgaagcag atggtacaca cgtg                                 34

<210> SEQ ID NO 32
<211> LENGTH: 24
<212> TYPE: DNA
<213> ORGANISM: artificial
<220> FEATURE:
<223> OTHER INFORMATION: oligo

<400> SEQUENCE: 32
gctaccaagg gtactggtgt cgtc                                          24

<210> SEQ ID NO 33
<211> LENGTH: 32
<212> TYPE: DNA
<213> ORGANISM: artificial
<220> FEATURE:
<223> OTHER INFORMATION: oligo

<400> SEQUENCE: 33
cgtgtgtacc atctaatgca ccagatgcct ac                                 32

<210> SEQ ID NO 34
<211> LENGTH: 32
<212> TYPE: DNA
<213> ORGANISM: artificial
<220> FEATURE:
<223> OTHER INFORMATION: oligo

<400> SEQUENCE: 34
gtaggcatct ggtgcattag atggtacaca cg                                 32

<210> SEQ ID NO 35
<211> LENGTH: 33
<212> TYPE: DNA
<213> ORGANISM: artificial
<220> FEATURE:
<223> OTHER INFORMATION: oligo

<400> SEQUENCE: 35
ccatctaatt caccagctga ctacattacc acc                                33

<210> SEQ ID NO 36
<211> LENGTH: 33
<212> TYPE: DNA
<213> ORGANISM: artificial
<220> FEATURE:
<223> OTHER INFORMATION: oligo

<400> SEQUENCE: 36
ggtggtaatg tagtcagctg gtgaattaga tgg                                33

<210> SEQ ID NO 37
<211> LENGTH: 33
<212> TYPE: DNA
<213> ORGANISM: artificial
<220> FEATURE:
<223> OTHER INFORMATION: oligo

<400> SEQUENCE: 37
ccatctaatt caccagctgc ctacattacc acc                                33

<210> SEQ ID NO 38
<211> LENGTH: 33
<212> TYPE: DNA
<213> ORGANISM: artificial
<220> FEATURE:
<223> OTHER INFORMATION: oligo

<400> SEQUENCE: 38
ggtggtaatg taggcagctg gtgaattaga tgg                                33

<210> SEQ ID NO 39
<211> LENGTH: 32
<212> TYPE: DNA
<213> ORGANISM: artificial

```
<220> FEATURE:
<223> OTHER INFORMATION: oligo

<400> SEQUENCE: 39
cttcgtattg atggaggccg gcacgggcgc ag                                    32

<210> SEQ ID NO 40
<211> LENGTH: 32
<212> TYPE: DNA
<213> ORGANISM: artificial
<220> FEATURE:
<223> OTHER INFORMATION: oligo

<400> SEQUENCE: 40
gaagcataac tacctccggc cgtgcccgcg tc                                    32

<210> SEQ ID NO 41
<211> LENGTH: 17
<212> TYPE: DNA
<213> ORGANISM: artificial
<220> FEATURE:
<223> OTHER INFORMATION: oligo

<400> SEQUENCE: 41
cggctctgag ccagatc                                                     17

<210> SEQ ID NO 42
<211> LENGTH: 66
<212> TYPE: DNA
<213> ORGANISM: E. coli

<400> SEQUENCE: 42
ctgaccgttt acactacccg cccggacacc tttatgggtt gtacctacct ggcggtagct     60
gcgggt                                                                 66

<210> SEQ ID NO 43
<211> LENGTH: 66
<212> TYPE: DNA
<213> ORGANISM: T. thermophilus

<400> SEQUENCE: 43
atccccgtct tcaccacccg ccccgacacc ctcttcggag ccaccttcct cgtgctcgcc     60
ccggag                                                                 66

<210> SEQ ID NO 44
<211> LENGTH: 66
<212> TYPE: DNA
<213> ORGANISM: B. subtilis

<400> SEQUENCE: 44
tttacagtgt ttaacaacaag accagatacg ctgtttggcg ctacatacac tgtccttgcc    60
ccggaa                                                                 66

<210> SEQ ID NO 45
<211> LENGTH: 66
<212> TYPE: DNA
<213> ORGANISM: S. cerevisiae

<400> SEQUENCE: 45
ttgattgtct ttaacaacaag accggaaact cttttttgctg tacagtatgt tgctctcgca   60
ttagac                                                                 66
```

<210> SEQ ID NO 46
<211> LENGTH: 66
<212> TYPE: DNA
<213> ORGANISM: E. coli

<400> SEQUENCE: 46
ctggtggtcg cgactacccg tccggaaacc ctgctgggcg atactggcgt agccgttaac    60
ccggaa                                                              66

<210> SEQ ID NO 47
<211> LENGTH: 66
<212> TYPE: DNA
<213> ORGANISM: B. subtilis

<400> SEQUENCE: 47
attgaaattg cgacgacacg tcctgaaaca atgctcggtg atacagctgt tgccgttcac    60
cctgaa                                                              66

<210> SEQ ID NO 48
<211> LENGTH: 113
<212> TYPE: DNA
<213> ORGANISM: B. stearothermophilus

<400> SEQUENCE: 48
attgaaatgg cgaaattgcc gctttacggt gacgacgaag cggcgaaaaa gacgacgcgc    60
tccgtgttgg cgtatgtgct cgacaacacg atgcgcctgc ttcacccgtt tat          113

<210> SEQ ID NO 49
<211> LENGTH: 66
<212> TYPE: DNA
<213> ORGANISM: E. coli

<400> SEQUENCE: 49
ctggtgatct ggaccactac gccgtggact ctgcctgcga accgcgcaat ctctattgca    60
cctgat                                                              66

<210> SEQ ID NO 50
<211> LENGTH: 66
<212> TYPE: DNA
<213> ORGANISM: T. thermophilus

<400> SEQUENCE: 50
ctcctcatct ggaccaccac cccctggacc ctgcccggga acgtggccgc agcagtccac    60
ccggag                                                              66

<210> SEQ ID NO 51
<211> LENGTH: 62
<212> TYPE: DNA
<213> ORGANISM: S. aureus

<400> SEQUENCE: 51
tttattatct ggacaacaac gccatggaca attccatcaa atgttgcgat taccgttcat    60
cc                                                                  62

<210> SEQ ID NO 52
<211> LENGTH: 78
<212> TYPE: DNA
<213> ORGANISM: S. cerevisiae

```
<400> SEQUENCE: 52
aagggtactg gtgtcgtcac gtgtgtacca tctaattcac cagatgacta cattaccacc    60
aaggacttgt tgcacaaa                                                  78

<210> SEQ ID NO 53
<211> LENGTH: 78
<212> TYPE: DNA
<213> ORGANISM: C. elegans

<400> SEQUENCE: 53
aagggaactg gtgttgttac aagtgtacca tcagactctc cagatgattt tgcagctttg    60
tcggatctca agaagaag                                                  78

<210> SEQ ID NO 54
<211> LENGTH: 78
<212> TYPE: DNA
<213> ORGANISM: N. crissa

<400> SEQUENCE: 54
aagggtaccg gtgtcgtcac ctccgttccc tccgactctc ccgacgactg cgccatgatg    60
accgagctcg ccaagaag                                                  78

<210> SEQ ID NO 55
<211> LENGTH: 78
<212> TYPE: DNA
<213> ORGANISM: H. sapiens

<400> SEQUENCE: 55
aaaggcactg gtgtggttac aagtgttcct tccgactccc ctgatgatat tgctgccctc    60
agagacttga agaaaaag                                                  78

<210> SEQ ID NO 56
<211> LENGTH: 72
<212> TYPE: DNA
<213> ORGANISM: E. coli

<400> SEQUENCE: 56
tacggcacgg gcgcagtaat ggcggttccg gggcacgacc aacgcgacta cgagtttgcc    60
tctaaatacg gc                                                        72

<210> SEQ ID NO 57
<211> LENGTH: 72
<212> TYPE: DNA
<213> ORGANISM: T. thermophilus

<400> SEQUENCE: 57
tacggcaccg gggccatcat ggccgtccct gcccacgacc agagggacta cgagttcgcc    60
aggaagttcg gc                                                        72

<210> SEQ ID NO 58
<211> LENGTH: 72
<212> TYPE: DNA
<213> ORGANISM: B. subtilis

<400> SEQUENCE: 58
```

```
tacggaacag gtgctgtcat ggcagttcca ggacacgatg agcgtgattt tgaattcgcc    60
aaaacattcg gc                                                       72

<210> SEQ ID NO 59
<211> LENGTH: 84
<212> TYPE: DNA
<213> ORGANISM: S. cerevisiae

<400> SEQUENCE: 59
tatggttcag cacctagtgc agtaatgggt tgtccaggac acgataaccg agattttgag    60
ttttggcaaa caaattgtcc tggt                                          84

<210> SEQ ID NO 60
<211> LENGTH: 72
<212> TYPE: DNA
<213> ORGANISM: E. coli

<400> SEQUENCE: 60
aaaggcaccg gctgcgtgaa atcactccg gcgcacgact ttaacgacta tgaagtgggt    60
aaacgtcacg cg                                                       72

<210> SEQ ID NO 61
<211> LENGTH: 72
<212> TYPE: DNA
<213> ORGANISM: B. subtilis

<400> SEQUENCE: 61
tttggttcag gtgccgtgaa aattacgcct gctcatgatc cgaacgactt cgagcttggc    60
aaccgccaca at                                                       72

<210> SEQ ID NO 62
<211> LENGTH: 72
<212> TYPE: DNA
<213> ORGANISM: B. stearothermophilus

<400> SEQUENCE: 62
ttcggctctg gggcggtcaa aattacgccg gcgcacgacc cgaacgactt tgaaatcggc    60
aatcgccaca ac                                                       72

<210> SEQ ID NO 63
<211> LENGTH: 72
<212> TYPE: DNA
<213> ORGANISM: E. coli

<400> SEQUENCE: 63
gccggtaccg gtgccgttca caccgcgcct ggccacggcc cggacgacta tgtgatcggt    60
cagaaatacg gc                                                       72

<210> SEQ ID NO 64
<211> LENGTH: 72
<212> TYPE: DNA
<213> ORGANISM: T. thermophilus

<400> SEQUENCE: 64
gacgggacgg gcatcgtcca ccaggccccc gccttcggcg ccgaggacct ggagacggcg    60
agggtctacg gg                                                       72

<210> SEQ ID NO 65
<211> LENGTH: 72
```

```
<212> TYPE: DNA
<213> ORGANISM: S. aureus

<400> SEQUENCE: 65
gaaggaactg gtattgttca tatagcacca gctcatgggg aagatgacta ccaattggtt    60
ttagagcgtg at                                                        72
```

METHOD AND COMPOSITION FOR LEUCYL-TRNA SYNTHETASES AND DERIVATIVES THEREOF THAT ACTIVATE AND AMINOACYLATE NON-LEUCINE AMINO ACID TO TRNA ADAPTOR MOLECULES

CROSS REFERENCE TO RELATED APPLICATIONS

The present application claims priority to U.S. application Ser. No. 60/323,582 filed Sep. 20, 2001. The specification of the prior application is incorporated by reference into this specification.

STATEMENT REGARDING FEDERALLY SPONSORED RESEARCH OR DEVELOPMENT

The present application was supported in part by the National Institutes of Health grant number GM63789. The government may have certain rights in the invention.

REFERENCE TO A "SEQUENTIAL LISTING," A TABLE, OR A COMPUTER PROGRAM LISTING APPENDIX SUBMITTED ON A COMPACT DISC

A nucleotide and/or amino acid sequence listing is incorporated by reference of the material on computer readable form that includes 1 (one) diskette (file name: 123029-1016 SEQUENCE LISTING.ST25.txt; size: 9 kB) created on Sep. 20, 2002.

BACKGROUND OF THE INVENTION

1. Field of the Invention

The present invention relates to the general field of protein synthesis, and more particularly, to compositions of tRNA synthetases, analogs and derivatives, thereof, and modified tRNAs that deliver non-cognate amino acids and methods for their creation, isolation and use.

2. Description of Related Art

The scientific research community has been trying to develop techniques that will allow the synthesis of custom designed proteins. Custom designed proteins are a target due to their potential applications for use in medicinal, therapeutic, diagnostic, biotechnology, engineering, and spectroscopy. Current technology relies primarily on chemical synthesis. The invention described herein was developed as a method and composition for the enzymatic and ribosome-based synthesis of custom proteins that will overcome the shortfalls of the current background art by using tRNA synthetases, their analogs and derivatives, thereof, to aminoacylate noncognate amino acids to transfer RNAs (tRNAs, their analogs and derivatives, thereof) for incorporation of the non-cognate amino acids into proteins.

The present invention includes, but is not limited to, leucyl-tRNA synthetase wild-type and mutant proteins and certain editing mutants of isoleucyl-tRNA synthetases and valyl-tRNA synthetases that can misaminoacylate their cognate tRNA molecules with noncognate amino acids. It also includes, but is not limited to mutants of leucyl-tRNA synthetase that alter specificity of the activation and aminoacylation of leucine and/or noncognate amino acids. These mutant leucyl-tRNA synthetases are those that increase specificity of leucine and/or those that increase specificity of non-leucine amino acids, increase specificity of leucine while decreasing specificity of non-leucine amino acids, and increase specificity of non-leucine amino acids, while decreasing specificity of leucine.

Presently, non-enzymatic chemical acylation methods are used that covalently link non-standard amino acids to suppressor tRNAs which interact selectively with the amber (UAG) stop codon. These tRNAs and genes containing the amber mutation were incorporated into in vitro translation systems to generate proteins with site-specific incorporation of non-standard amino acids. This non-enzymatic, chemistry-based process has been commercialized by at least one company (Cruachem, Aston, Pa.), but is laborious, costly, and limited to low yields as compared to an enzymatic based approach.

Another approach is the use of an "orthogonal" tRNA, which is not recognized by existing *Escherichia coli* (*E. coli*) aminoacyl-tRNA synthetase (aaRS). The orthogonal tRNA was created based on mutations of tRNA$^{Gln}$. A complementary mutant glutaminyl-tRNA synthetase (GlnRS) was evolved in vitro to specifically aminoacylate the orthogonal tRNA with glutamine. This tRNA synthetase was further proposed for re-engineering of the amino acid binding pocket to activate non-standard amino acids. A mutant tRNA synthetase that aminoacylates non-glutamine amino acids to the orthogonal tRNA would create a twenty-first aaRS-tRNA pair that could be used in vivo for large scale production of proteins that contain site-specifically inserted non-standard amino acids.

A unique tRNA synthetase/tRNA pair has been developed based on the tyrosine system. The mutant tyrosyl-tRNA synthetase (TyrRS) aminoacylates or covalently links non-standard amino acids including O-methyl-L-tyrosine to tRNAs that contain an amber suppressor anticodon. The genes for this tRNA synthetase and tRNA have been used to transform *E. coli*. In vivo expression of these two genes within *E. coli* yield intracellularly synthesized proteins, expressed from genes with amber codons that contain site-specific incorporation of O-methyl-L-tyrosine. This system was also used with aspartic acid tRNA synthetase/tRNA$^{Asp}$ pairs.

Another method has been to evolve ribozymes made of RNA that can aminoacylate or covalently attach amino acids to tRNAs. The ribozymes exhibiting aminoacylation activity were isolated by in vitro selection techniques (also called SELEX: systematic evolution of ligands by exponential enrichment. These ribozymes have been used to attach standard amino acids including glutamine and phenylalanine to tRNA molecules. Standard amino acids that contain modifications such as biotin groups can also be aminoacylated by the selected ribozymes. RNA molecules could be further developed to specifically aminoacylate tRNA molecules with diverse non-standard amino acids and incorporated into in vitro translation systems for protein synthesis. It is possible that they could also be adapted for aminoacylation of non-standard amino acids in vivo.

Some aaRSs have difficulty completely discriminating structurally similar amino acids that compete with the cognate amino acid. It is known that non-standard amino acids can be incorporated into proteins if they are highly similar to a standard amino acid and misactivated for aminoacylation by a native tRNA synthetase. For example, trifluoroleucine is aminoacylated to tRNA$^{Leu}$ by *E. coli* leucyl-tRNA synthetase (LeuRS), wherein media was supplemented with trifluoroleucine in the absence of leucine to support bacterial cell growth. Under these growth conditions, leucine substitutions by trifluoroleucine for total protein reached levels of 92%. In another example, LeuRS mischarges norvaline in vivo and isoleucine and methionine in vitro. Leucyl-tRNA synthetase has evolved a second hydrolytic active site to edit misactivated and mischarged amino acids to ensure that the correct amino acid is aminoacylated to the cognate tRNA.

Non-cognate amino acids that are misactivated or mischarged to tRNA may also be hydrolytically edited by tRNA synthetases that are related to LeuRS. These include isoleucyl-tRNA synthetase (IleRS), valyl-tRNA synthetase (ValRS), a mutant ValRS lacking editing activity, and Archae-based LeuRS. The mutant ValRS aminoacylates cysteine, threonine, and aminobutyrate to tRNA$^{Val}$. In vivo studies showed that when E. coli containing the mutant ValRS was grown on media supplemented with aminobutyrate that 24% of all of the valines within proteins were replaced by aminobutyrate.

It is possible to inactivate the editing mechanism of these tRNA synthetases to stably aminoacylate noncognate amino acids to tRNAs. Aspartic acids in the hydrolytic editing active site of LeuRS, ValRS, and IleRS were proposed to play essential roles in the editing mechanism in E. coli LeuRS. An aspartic acid that is universally conserved between IleRS, ValRS, and LeuRS was proposed to be involved in a salt bridge with the $\alpha$-NH$_4^+$ on the amino acid backbone of the amino acid editing substrate based on structural modeling of ValRS. A second nearby highly conserved aspartic acid that was predicted to be essential to the pre-transfer editing mechanism is in position to form a hydrogen bond with the 2' hydroxyl of the ribose ring based on structural information. A series of mutations of the universally conserved aspartic acid in E. coli IleRS altered or abolished its amino acid editing activity.

Problems Presented by Background Art. Chemical-based synthesis of aminoacylated tRNAs is laborious, costly, and limited to low yields. In contrast, enzymatic-based aminoacylation can be more efficient, economical, and can allow synthesis of high yields of aminoacylated tRNAs. Moreover, enzymes with altered specificity for amino acid substrates could be employed to incorporate non-standard amino acids into proteins using in vivo as well as in vitro methodologies. However, site specific incorporation of these non-standard amino acids aminoacylated to tRNAs in either in vitro or in vivo translation processes would require that the tRNA anticodon is altered to recognize a non-coding codon such as a stop codon.

Enzymatic aminoacylation of non-standard amino acids requires alteration of enzyme specificity to bind and activate noncognate amino acids. Many tRNA synthetases, including GlnRS, AspRS, ValRS, IleRS and TyrRS, require protein-anticodon interactions between the tRNA synthetase and tRNA to facilitate aminoacylation activity. Long distance coupling of amino acid binding/identity/activation and anticodon-protein interactions is thus hindered when the tRNA anticodon is changed, for example to an amber suppressor, to facilitate site specific incorporation of non-standard amino acids.

Limitations in the background art are overcome in the present invention by using LeuRS. LeuRS is one of the few tRNA synthetases that lack any dependence on specific interactions with the tRNA anticodon for substrate recognition and enzyme activity. Thus, the tRNA$^{Leu}$ anticodon can be readily changed to interact with other non leucine-encoding codons, such as stop codons, that have been previously exploited to incorporate alternate amino acids into specific sites within a protein.

High-level in vivo expression of recombinant proteins can be compromised by infidelity of certain tRNA synthetases. For example, overexpression of recombinant hemoglobin in Escherichia coli results in the substitution of norvaline amino acid intermediates for the standard amino acid leucine. Altering leucyl-tRNA synthetase to enhance specificity of leucine and decrease specificity of norvaline would lead to a higher fidelity of site-specific leucine incorporation during recombinant protein synthesis.

SUMMARY OF THE INVENTION

The invention described herein is a method and composition for the enzymatic synthesis (as used herein to include ribosomal-based synthesis) of proteins and other amino-acid containing molecules that will overcome the shortfalls of the prior art by using tRNA synthetases (and analogs and derivatives, thereof) to aminoacylate noncognate amino acids to tRNAs for incorporation of the noncognate amino acids into proteins. This invention includes, but is not limited to, leucyl-tRNA synthetase wild-type and mutant proteins and certain editing mutants of isoleucyl-tRNA synthetases and valyl-tRNA synthetases that can misaminoacylate their cognate tRNA molecules with noncognate amino acids.

In one embodiment, the present invention is a method to generate tRNA molecules that are misaminoacylated with noncognate (unnatural and nonstandard) amino acids, compositions of tRNA synthetases thereof, and methods for their practice.

In another embodiment, the present invention is a method to generate tRNA molecules that are aminoacylated with cognate amino acids with higher specificity than the wild type tRNA synthetases, compositions of tRNA synthetases thereof, and methods for their practice.

In still another embodiment, the present invention is a method of using tRNA synthetases with an inactivated amino acid editing mechanism to aminoacylate tRNAs with noncognate amino acids, compositions of mutant leucyl-tRNA synthetases and the genes expressing these proteins, and compositions of mutant isoleucyl and valyl-tRNA synthetases and the genes expressing these proteins. For example, a conserved aspartic acid residue within its amino acid editing domain called connective polypeptide 1 (CP1 domain) is substituted to inactivate its amino acid editing function. In addition, a mutant leucyl-tRNA synthetases or derivatives thereof that alter specificity of the activation and or aminoacylation of leucine and/or non-leucine amino acids may be used, wherein altering leucyl-tRNA synthetase specificity may include increasing or decreasing leucine amino acid specificity and/or increasing or decreasing non-leucine amino acid specificity.

As used herein, tRNA$^{Leu}$ molecules may be misaminoacylated with non-leucine amino acids, custom proteins or peptides, or other non-leucine amino acid containing molecules by using LeuRS and mutations thereof that covalently link non-leucine amino acids to tRNA substrates or tRNA mimics.

In still another embodiment, the present invention is specific mutations of LeuRS that allow LeuRS to covalently link non-leucine amino acids to tRNA, wherein, mutations may be nucleic acid sequences that encode relevant partial or full-length LeuRS molecules and their protein products, e.g., IleRS and ValRS protein mutants, and Archae-based LeuRS and their protein products, and gene mutants that link non-cognate amino acids to tRNAs. The invention may also be used to aminoacylate standard, non-leucine amino acids, for example, to tRNAs for incorporation at specific sites within a protein. The method and compositions described herein may be incorporated into in vitro and in vivo protein synthesis methods and processes to introduce non-standard amino acids into a protein. Non-standard amino acids would be defined as any amino acid or chemical analog thereof that does not include alanine, cysteine, aspartic acid, asparagine, glycine, phenylalanine, glycine, histidine, isoleucine, leucine, lysine, methionine, glutamic acid, glutamine, proline, arginine, serine, threonine, valine, tryptophan, and/or tyrosine. Examples of non-standard amino acids include, but are not limited to norvaline, norleucine, aminobutyrate, triflouroleucine, and homocysteine as well as amino acids that contain ketones or aldehydes in the side chain of the molecule.

Because aminoacyl-tRNA synthetases are responsible for the fidelity of protein synthesis they are necessary for accurate selection and activation of cognate amino acids for aminoacylation of the correct tRNA. Some tRNA synthetases have evolved an editing active site to enhance fidelity. Through use of the present invention, inactivation of editing active sites allows amino acids other than the cognate amino acid to be aminoacylated to tRNA. Hence, noncognate amino acids (i.e., unnatural or non-standard) of the present invention may be incorporated into custom designed proteins via ribosomal protein synthesis or by other means. For example, a tRNA adaptor molecule linked to a desired amino acid may be introduced to different proteins at one or more specific sites. Applications of the present invention includes the creation of stable and custom designed molecules and/or proteins containing novel amino acids at one or more specific sites for use in medicine, engineering, and biotechnology, as examples. The custom designed proteins may be any molecule that contains non-standard amino acids and/or alternate standard amino acids inserted at specific sites in place of the coded amino acids. Importantly, the present invention may be adapted to customize any molecule for diagnostic, therapeutic, screening, testing, or other biological or nonbiological purpose.

The composition and method of the present invention (e.g., LeuRS as an editing enzyme) may be a unique and powerful tool to aminoacylate non-leucine amino acids to tRNA molecules, a tRNA synthetase that does not require interactions with the tRNA anticodon in many organism. Because it relies on other parts of the RNA molecule for recognition, the anticodon may be altered to a stop codon for site-specific incorporation of novel amino acids due to its inherent propensity to interact effectively with non-leucine amino acids for aminoacylation. While LeuRS has evolved editing mechanisms to hydrolytically destroy its misactivated and misaminoacylated mistakes, mutant LeuRS enzymes of the present invention lack editing activity.

Leucyl-tRNA synthetase activates non-leucine amino acids and incorporates non-leucine amino acids when leucine is not available or present at low levels in vivo. Leucyl-tRNA synthetase mutations (i.e., that alter specificity) or derivatives thereof increase enzyme specificity for leucine and/or decrease specificity for non-leucine amino acids. In yet another embodiment of the present invention, leucyl-tRNA synthetase mutations increase fidelity and, hence, use of the mutant enzyme will increase the accuracy and purity of the synthesized protein. In yet another embodiment of the present invention, leucyl-tRNA synthetase mutations decrease leucine activation and aminoacylation while increasing non-leucine activation and aminoacylation and hence, use of the mutant enzyme will allow incorporation of non-standard and non-leucine amino acids at specific sites within proteins during ribosomal-based protein synthesis. Applications of this include its use for incorporating non-leucine amino acids at specific sites in proteins and/or other molecules.

Moreover, compositions of the present invention, including those resulting from editing mutant LeuRS and other tRNA synthetase, may serve as one or more templates to re-engineer the aminoacylation active site by mutagenesis to misaminoacylate nonstandard and novel amino acids. Custom designed protein products of the present invention include, but are not limited to, uses for medicinal, therapeutic, diagnostic, engineering, biotechnology, and spectroscopy applications.

BRIEF DESCRIPTION OF THE SEVERAL VIEWS OF THE DRAWINGS

For a more complete understanding of the features and advantages of the present invention, reference is now made to the detailed description of the invention along with the accompanying FIGURES in which corresponding numerals in the different FIGURES refer to corresponding parts and in which:

FIG. 2 depicts an example of a primary sequence alignment of the conserved editing region within the CP1 domain of LeuRS, ValRS, and IleRS, residues highlighted in dark gray are completely conserved within LeuRS and with one exception (Arg 249) with ValRS and IleRS and those shaded in medium gray are homologous within LeuRS and in most cases with ValRS and IleRS, such that amino acids highlighted in the lightest gray are homologous, but only to a particular aaRS and arrows identify sites in $E.\ coli$ LeuRS that were mutated via alanine scanning mutagenesis (A) and abbreviations are: Ec, $E.\ coli$; Tt, $T.\ thermophilus$; Bs, $B.\ subtilis$; Scm, $S.\ cerevisiae$ (mitochondrial); Sa, $S.\ aureus$; Bst, $B.\ stearothermophilus$, where numbers at the beginning and end of the amino acid sequences correspond to the amino acid position in the primary sequence of the first and last amino acid respectively and sequence alignments were generated using the Baylor College of Medicine Search Launcher ClustalW 1.8 Global progressive alignment program, each SEQ. ID NO. is: Ec LeuRS (SEQ ID NO.:42). Tt LeuRS (SEQ ID NO.:43), Bs LeuRS (SEQ ID NO.:44), Scm LeuRS (SEQ ID NO.:45). Ec ValRS (SEQ ID NO.:46). Bs ValRS (SEQ ID NO.:47), Bst ValRS (SEQ ID NO.:48), Ec IleRS (SEQ ID NO.:49), Tt IleRS (SEQ ID NO.:50) and Sa IleRS (SEQ ID NO.:51);

FIG. 6(A) depicts a cartoon representation of the LeuRS editing active site, wherein the Thr 252 residue is proposed to comprise a critical structural component of the amino acid binding pocket and Thr 252 inhibits leucine binding by either direct interference or indirectly alters the structure of the amino acid binding pocket (left) so that it is possible that Thr 252 structural barrier impedes leucine binding by clashing with the γ-branched methyl in the leucine side chain and when substituted by alanine, the structural barriers that impeded leucine binding are removed, and leucine is allowed to bind competently (right);

FIG. 6(B) depicts a cartoon representation of the LeuRS editing active site, wherein the Thr 252 residue is proposed to comprise a critical structural component of the amino acid binding pocket and the Thr 252 residue either directly or indirectly blocks leucine, but the straight-chained, non-bulky methionine can slide by the Thr 252 barrier to bind and the β-branched methyl in the isoleucine side chain would reside above the T252 barrier and thus isoleucine is not impeded in binding;

FIG. 12 depicts an example of a primary sequence alignment of a CP1-based conserved region within LeuRS, ValRS, and IleRS, wherein residues highlighted in dark gray are either completely or highly conserved between LeuRS, ValRS, and IleRS and those shaded in medium gray are homologous within LeuRS and in many cases with ValRS such that arrows identify conserved or homologous sites that were mutated including the completely conserved Asp 419 site in yeast cytoplasmic LeuRS that was mutated to an alanine (D419A) and abbreviations are: LeuRS, L; ValRS, V; IleRS, I; cytoplasmic, cyt; mitochondrial, mit; *S. cerevisiae*, Sc; *C. elegans*, Ce; *N. crassa*, Nc; *H. sapiens*, Hs; *E. coli*, Ec; *T. thermophilus*, Tt; *B. subtilis*, Bs; *S. aureus*, Sa; and *B. stearothermophilus*, Bst, where numbers at the beginning of the amino acid sequences correspond to the amino acid position in the primary sequence of the first amino acid respectively and alignments were generated using the Baylor College of Medicine Search Launcher ClustalW 1.8 Global progressive alignment program; each SEQ. ID NO. is: ScL-cyt (SEQ ID NO.:52), CeL-cyt (SEQ ID NO.: 53), NcL-cyt (SEQ ID NO.54), HsL-cyt (SEQ ID NO.:65), EcL (SEQ ID NO.:66), TtL (SEQ ID NO.:67), BsL (SEQ ID NO.68), ScL (SEQ ID NO. :69), EcV (SEQ ID NO.:60), BsV (SEQ ID NO.:61), BstV (SEQ ID NO.:62), EcI (SEQ ID NO.:63), TtI (SEQ ID NO.:64), SaI (SEQ ID NO.:65);

FIG. 50 depicts an example of a primary sequence alignment of a CP1-based conserved region within prokaryotic LeuRSs and ValRS, wherein residues highlighted in black are either completely or highly conserved between LeuRS and ValRS and those shaded in medium gray are homologous within LeuRS and in many cases with ValRS such that arrows identify conserved or homologous sites that were mutated including the highly conserved Asp 342 and the completely conserved Asp 345 site in E. coli LeuRS that was mutated to an alanine (D345A) with abbreviations of: LeuRS, L; ValRS, V; mitochondrial, mit; S. cerevisiae, Sc; E. coli, Ec; T. thermophilus, Tt; B. subtilis, Bs; and G. stearothermophilus, Gs, where numbers at the beginning of the amino acid sequences correspond to the amino acid position in the primary sequence of the first amino acid respectively and alignments were generated using the Baylor College of Medicine Search Launcher ClustalW 1.8 Global progressive alignment program.

DETAILED DESCRIPTION OF THE INVENTION

Although making and using various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention, and do not limit the scope of the invention.

To facilitate the understanding of this invention, a number of terms are defined within. Terms defined and used herein have meanings as commonly understood by a person of ordinary skill in the areas relevant to the present invention. Terms such as "a," "an," and "the" are not intended to refer to only a singular entity, but include the general class of which a specific example is used for illustration. The terminology and examples herein are used to describe specific embodiments of the invention, but their usage does not limit the invention, except as outlined in the claims.

Misaminoacylation of tRNA by mutant synthetases or derivatives thereof can be used to enzymatically aminoacylate tRNAs with nonstandard, unusual or novel amino acids for incorporation into custom designed proteins during ribosomal-based protein synthesis. LeuRS and also IleRS and ValRS are organized modularly into three domains (Cusack et al., 2000, Martinis and Schimmel, 1996). An N-terminal conserved catalytic core is responsible for ATP-dependent activation of amino acids and subsequent aminoacylation to tRNA molecules. A less or unconserved C-terminal domain is typically responsible for interactions with non-acceptor stem parts of the tRNA molecule such as the anticodon in tRNA synthetases that are closely related to LeuRS. In the case of most LeuRS proteins, the C-terminal domain as well as any other part of the LeuRS protein does not interact with the anticodon (Asahara et al., 1993; Dietrich et al., 1990). The primary sequence of the conserved catalytic core that folds into a Rossmann nucleotide binding fold is split by a protein insertion called connective polypeptide 1 (CP1) (Starzyk et al., 1987). The CP1 protein insert folds into a discrete domain and contains the amino acid editing active site (Chen et al., 2000; Hendrickson et al., 2000; Lin et al., 1996; Mursinna et al., 2001; Nureki et al., 1998; Nureki et al., 1999).

Figure 1:
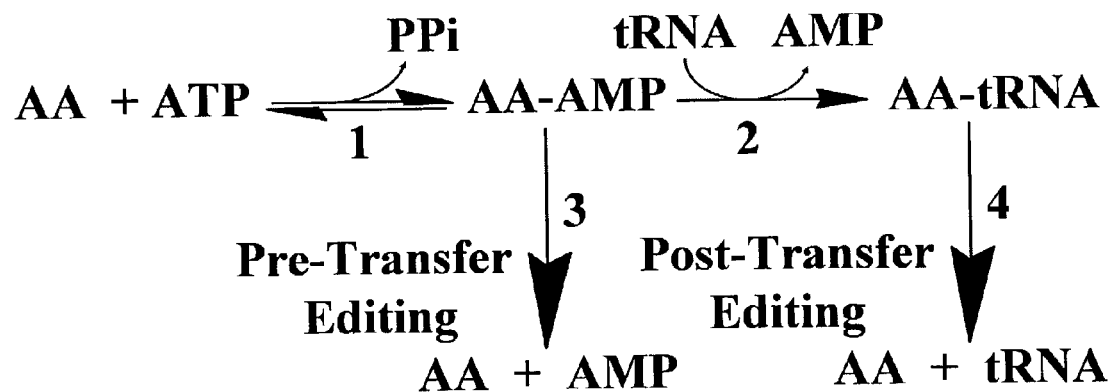
FIG. 1 is a reaction scheme for Class 1 aminoacyl-tRNA synthetases that possess a CP1-based editing mechanism, wherein individual reactions are: 1) amino acid activation via ATP, 2) aminoacylation of the tRNA, 3) pre-transfer editing of the aminoacyl-adenylate, 4) post-transfer editing of the mischarged tRNA.

To enhance fidelity, the aaRSs rely on a "double sieve" mechanism for amino acid selection and discrimination (Fersht, 1977). The first sieve encompasses the aminoacylation active site that binds cognate amino acids but cannot adequately filter out all closely related amino acids. The second sieve is an editing active site that targets those noncognate amino acids that are misactivated or mischarged but, importantly, bars the correctly charged cognate amino acid from hydrolysis. LeuRS, ValRS, and IleRS enzymes edit by homologous CP1 domains (Chen et al., 2000; Chen et al., 2001; Lin et al., 1996; Mursinna et al., 2001; Mursinna and Martinis, 2002). An editing active site hydrolytically cleaves the misactivated aminoacyl-adenylate (called "pre-transfer editing") or the mischarged tRNA (called "post-transfer editing") as shown in the reaction in FIG. 1 (Baldwin and Berg, 1966; Fersht, 1977; Norris and Berg, 1964; Englisch et al., 1986; Schimmel and Schmidt, 1995). It has been unclear whether the editing active sites for pre- and post-transfer editing are separate, overlap, or partially overlap.

Separate amino acid binding pockets for pre- and post-transfer editing substrates have been postulated based on modeling and comparative analysis of the homologous ValRS and IleRS co-crystal structures (Fukai et al., 2000; Nureki et al., 1998). The two sites are distinct but proximal to each other and rely on a distinct set of amino acids to confer amino acid specificity. The prediction was based on the location of the terminal adenosine of the complexed tRNA$^{Val}$ and modeling of threonyl-adenylate and threonine in the editing site. Threonine, but not valine, could be fit into two distinct pockets.

Leucyl-tRNA synthetase (LeuRS) misactivates a diverse group of standard amino acids and non-standard metabolic amino acid intermediates (Apostol et al., 1997; Englisch et al., 1986; Lincecum Jr. and Martinis, 2000; Martinis and Fox, 1997). Because of the shape and the larger size of leucine, specific recognition by LeuRS may be more complex than simply distinguishing isosteric substrates that differ by a single methyl group by size exclusion. Its hydrolytic editing activity targets either misactivated aminoacyl-adenylate or mischarged aminoacyl-tRNA$^{Leu}$ (Chen et al., 2000; Chen et al., 2001; Englisch et al., 1986; Mursinna et al., 2001; Mursinna and Martinis, 2002). Previous work has suggested that LeuRS from different organisms may preferentially rely on either pre- or post-transfer editing mechanisms (Englisch et al., 1986) rather than a combination as found with IleRS (Baldwin and Berg, 1966; Norris and Berg, 1964). In particular, it was proposed that *S. cerevisiae* cytoplasmic LeuRS used primarily pre-transfer editing although tRNA was shown to stimulate the reaction. In contrast, *E. coli* LeuRS exclusively utilized a post-transfer editing mechanism to prevent the release of mischarged tRNA$^{Leu}$.

As used herein leucyl tRNA synthetase includes any variation of the enzyme, including any derivative, natural enzyme, synthetic analog, engineered enzyme, mimetic, single mutant, multiple mutant, mutant with deletions, chimeric molecule, versions that are cognate to other amino acids, and combinations thereof and from any eukaryotic, bacterial, and archaebacterial organism. The chimeric molecules may also include different isoacceptors or non-leucine tRNAs as well as a linker molecule that may be a protein, peptide, antibody, etc.

Figure 3:
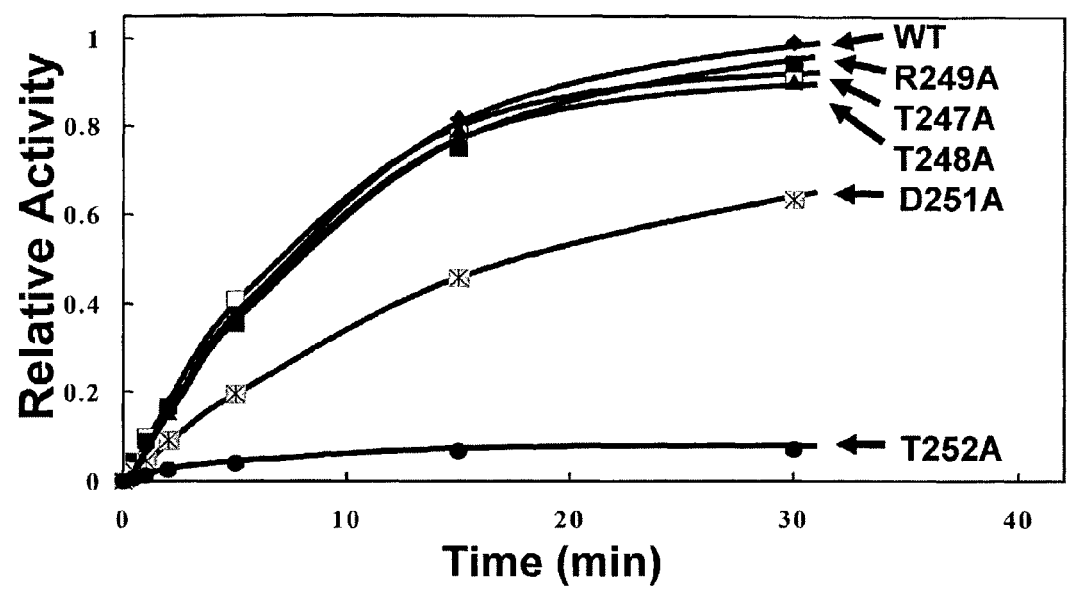
FIG. 3 is a graph representing aminoacylation of tRNA$^{Leu}$ with leucine, wherein each reaction was repeated at least three times and normalized relative to the wild-type enzyme's activity and symbols represent aminoacylation activity by wild-type and mutant LeuRSs are: wild-type (WT), closed diamond; R249A, closed square; T247A, open square; T248A, closed triangle; D251A, shaded asterisk; T252A, closed circle, such that activities for different preparations of D251A LeuRS mutant varied, but were consistently decreased by up to 70% compared to wild-type LeuRS.
Figure 4:
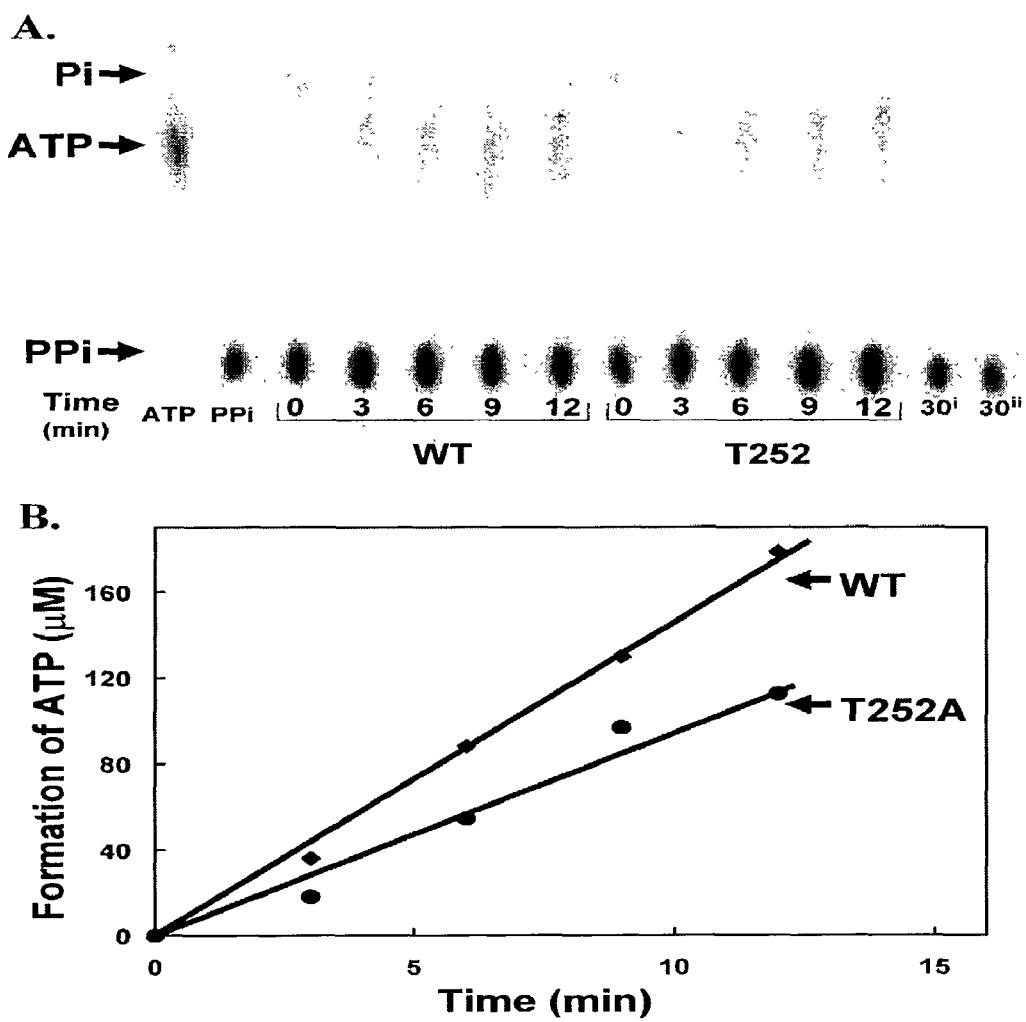
FIG. 4(A) depicts a phosphorimage of leucine-dependent PP$_i$ exchange activity for wild-type and T252A LeuRS, wherein aliquots of 2 µl of the PPi exchange assay mixture were quenched directly on the TLC plate at specific time points as indicated and ATP was chromatographically separated from PP, [and background phosphate (P$_i$)] and analyzed by phosphorimaging, so that the two lanes labeled 30$^i$ and 30$^{ii}$ are 30 minute control reactions in which amino acid was omitted from the reaction mixture (30$^i$, wild-type; 30$^{ii}$, T252A)
FIG. 4(B) is a graph of phosphorimaged data from FIG. 4(A), wherein the phosphorimaged data was converted quantitatively to determine ATP formation and symbols are: wild-type (WT) LeuRS, closed diamond; T252A LeuRS, closed circle.
Figure 5:
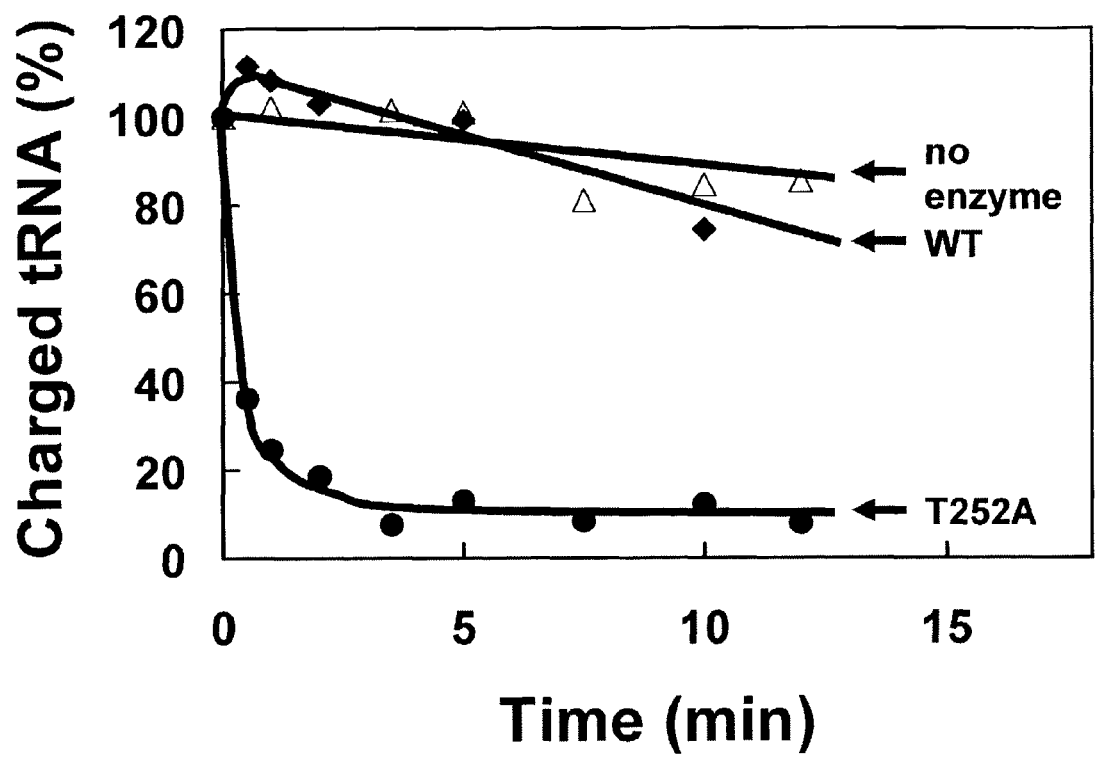
FIG. 5 is a graph of deacylation of Leu-tRNA$^{Leu}$ by wild-type and T252A LeuRS and symbols are: wild-type (WT) LeuRS, closed diamond; T252A LeuRS, closed circle; no enzyme control, open triangle.
Figure 7:
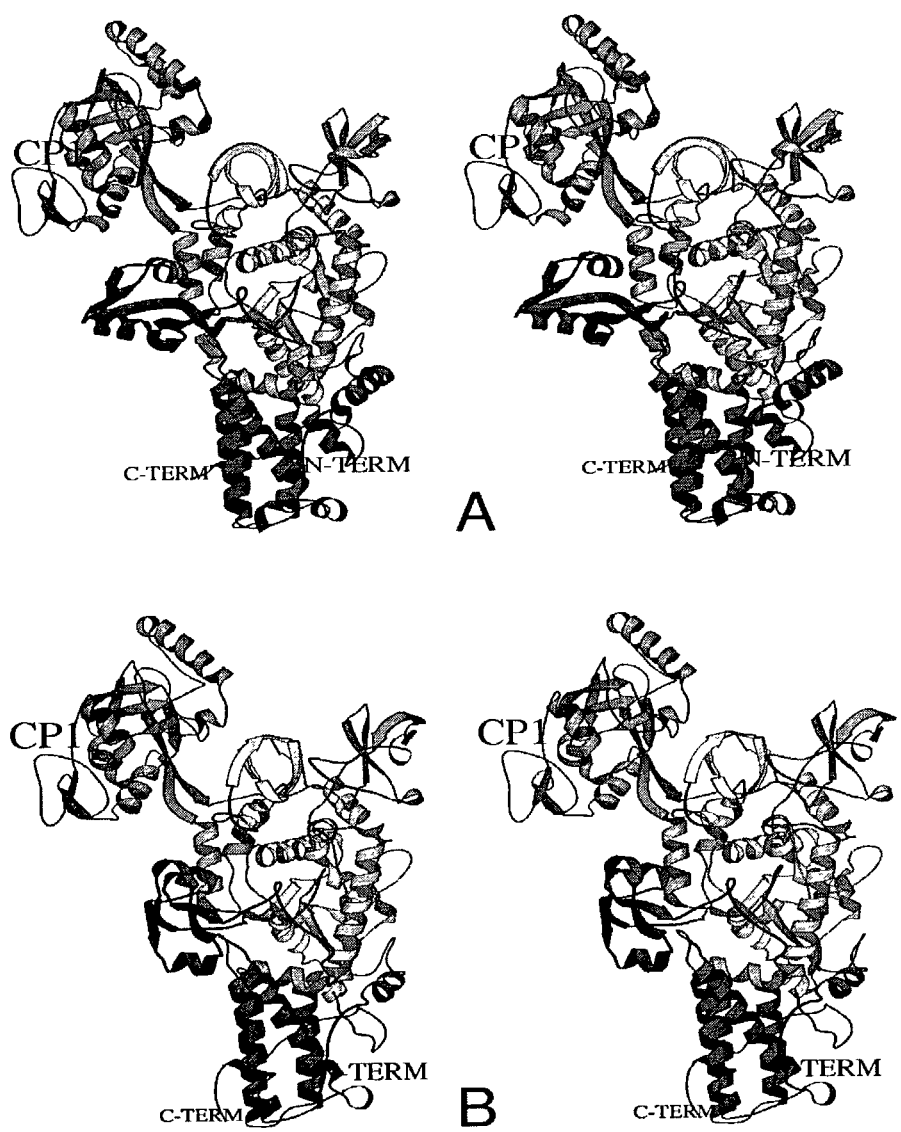
FIG. 7(A) depicts a stereo ribbon diagram of the X-ray structure of *Thermus thermophilus* LeuRS as reported by Cusack et al. (Cusack et al., 2000)
FIG. 7(B) depicts a stereo ribbon diagram of the homology modeling structure of *E. coli* LeuRS, wherein the backbone atom root mean squared deviation (RMSD) for the overall structure between FIGS. 7A and 7B is 1.19 Angstroms and for the CP1 domain is 0.60 Angstroms.
Figure 8:
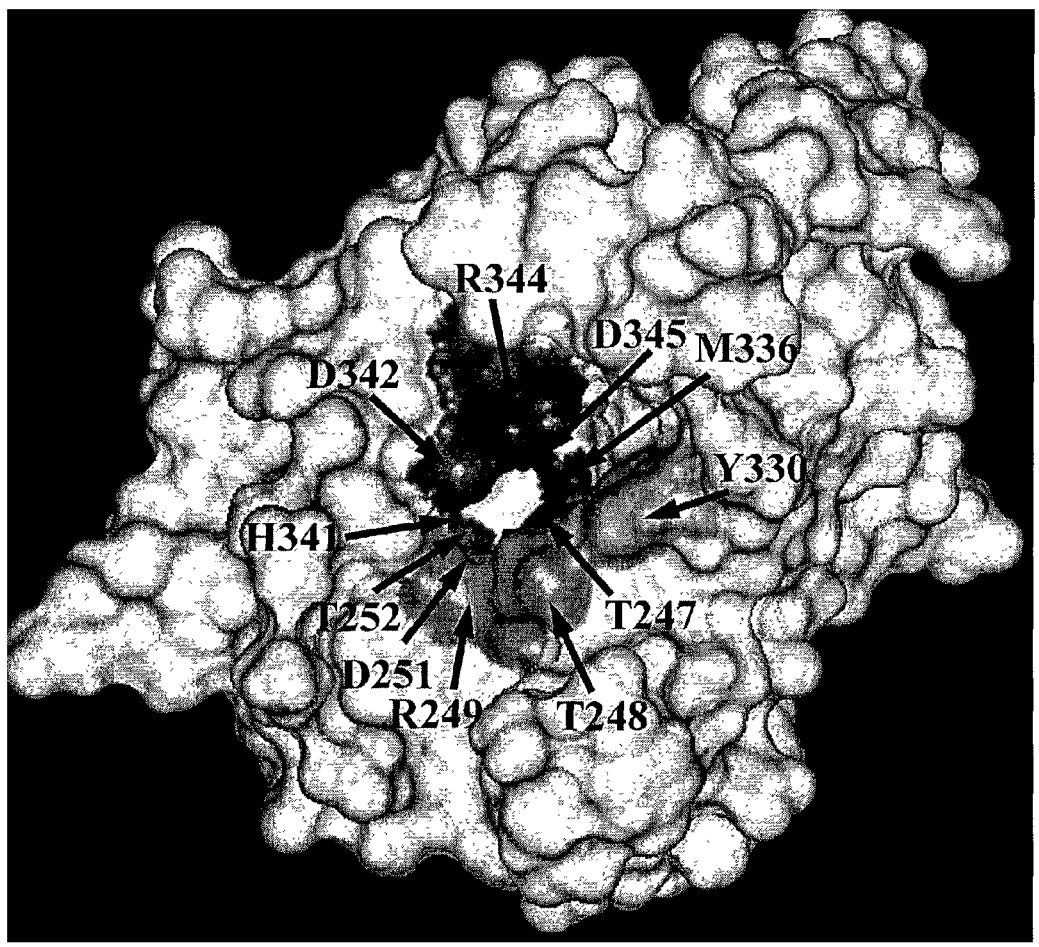
FIG. 8 depicts a molecular surface of the minimized homology model of *E. coli* LeuRS's CP1 domain, wherein the residues creating and near the proposed amino acid binding pocket of the editing active site are labeled.
Figure 9:
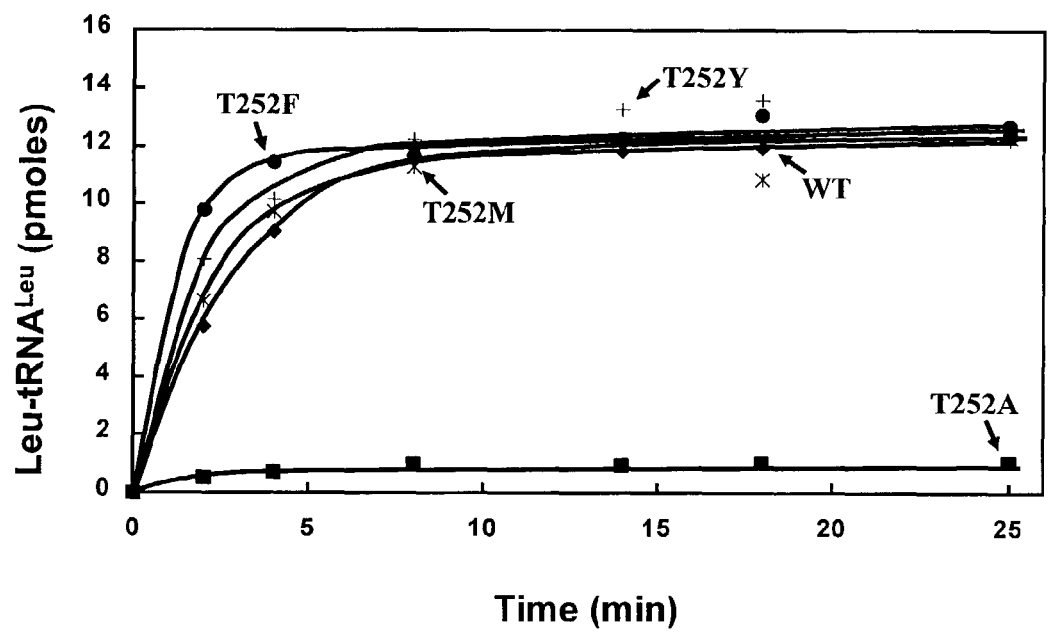
FIG. 9 is a graph of aminoacylation of tRNA$^{Leu}$ with leucine by LeuRS mutants that contain substitutions by amino acids with larger side chains at the conserved Thr 252 residue, wherein each reaction was done in triplicate and symbols representing aminoacylation activity by wild-type and mutant LeuRSs are: wild-type (WT), closed diamond; T252A, closed square; T252F, closed circle; T252M, asterisk sign, and T252Y, plus sign.
Figure 10:
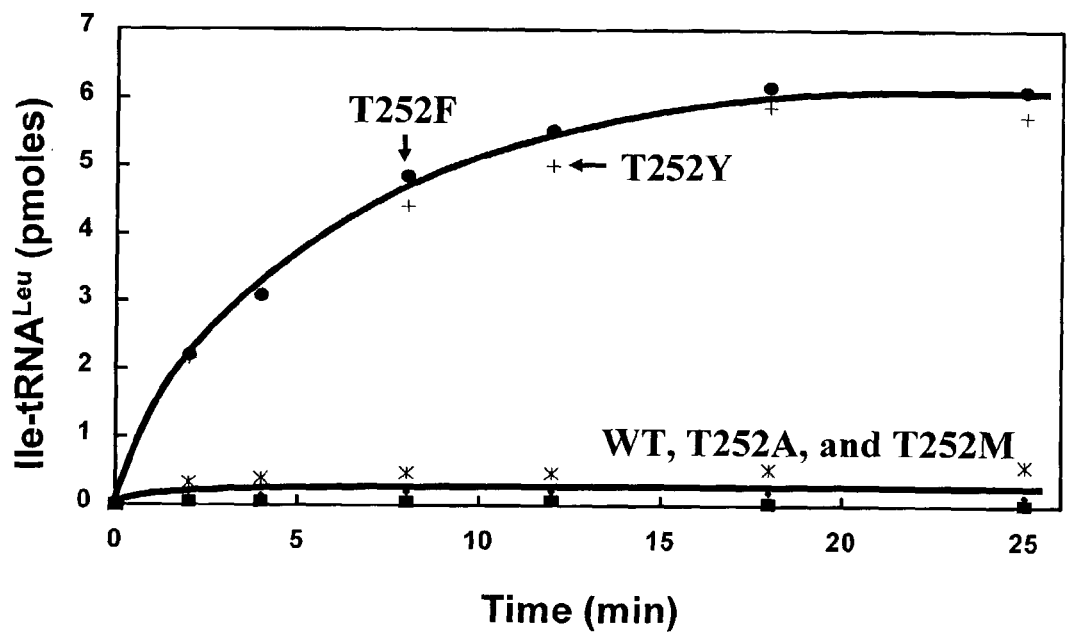
FIG. 10 is a graph of isoleucylation of tRNA$^{Leu}$ by LeuRS mutants that contain substitutions by amino acids with larger side chains at the conserved Thr 252 residue and symbols representing isoleucylation activity by wild-type and mutant LeuRSs are: wild-type (WT), closed square; T252A, closed diamond; T252M, asterisk sign; T252F, closed circle; and T252Y, plus sign.

In one embodiment of the present invention, the inventors use alanine-scanning mutagenesis of *E. coli* LeuRS to identify a conserved threonine residue (Thr 252) in a CP1-based threonine-rich region (FIG. 2) that is critical to amino acid substrate discrimination within the amino acid editing active site (Mursinna et al., 2001). Substitution via site-directed mutagenesis of the gene encoding *E. coli* LeuRS changed the Thr 252 residue to an alanine (T252A) resulting in uncoupled amino acid specificity and facilitated editing of the correctly aminoacylated leucine-tRNA$^{Leu}$ molecule (FIGS. 3, 4 and 5). The full homology modeled and minimized structure for *E. coli* LeuRS (Lee and Briggs, 2002) is shown in FIG. 7B along with that of the X-ray structure for *T. thermophilus* (FIG. 7A; Cusack et al., 2000) Subsequent computational homology modeling of *E. coli* LeuRS followed by docking studies suggested that the Thr 252 is located near the bottom of a depression on the protein surface that could act as an amino acid binding pocket (FIGS. 6 and 8). Two bulky amino acids, phenylalanine (T252F) and tyrosine (T252Y), were substituted subsequently for Thr 252 by site-directed mutagenesis to block the amino acid binding pocket and abolish amino acid editing activity (Mursinna and Martinis, 2002). The mutant enzymes aminoacylated leucine similar to the wild-type LeuRS (FIG. 9). While wild-type LeuRS edits isoleucine-tRNA$^{Leu}$, these two composition inventions of mutant LeuRS (T252F and T252Y) stably misaminoacylate the non-cognate isoleucine amino acid to tRNA$^{Leu}$ (FIG. 10).

Figure 13:
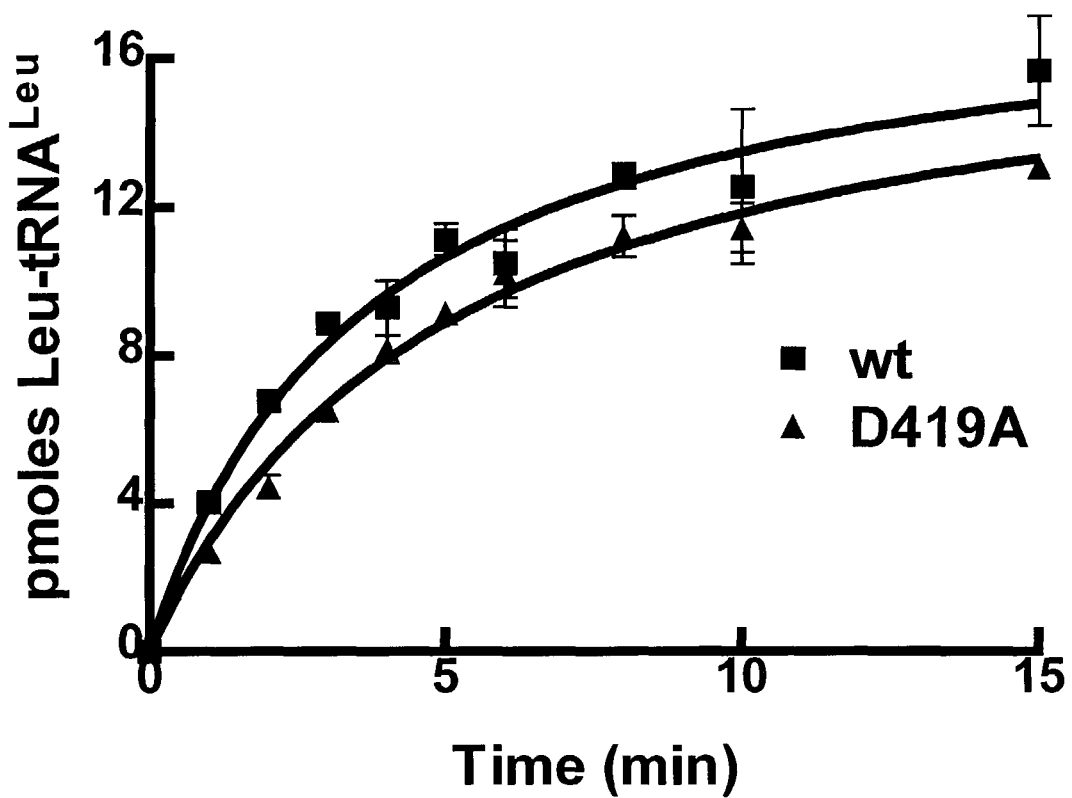
FIG. 13 is a graph of aminoacylation of tRNA$^{Leu}$ with leucine by yeast cytoplasmic wild-type and D419A mutant LeuRSs, wherein each reaction was done in triplicate, error bars are indicated and symbols representing aminoacylation activity by wild-type and D419A mutant LeuRSs are: wild-type (wt), closed square; D419A, closed triangle.
Figure 18:
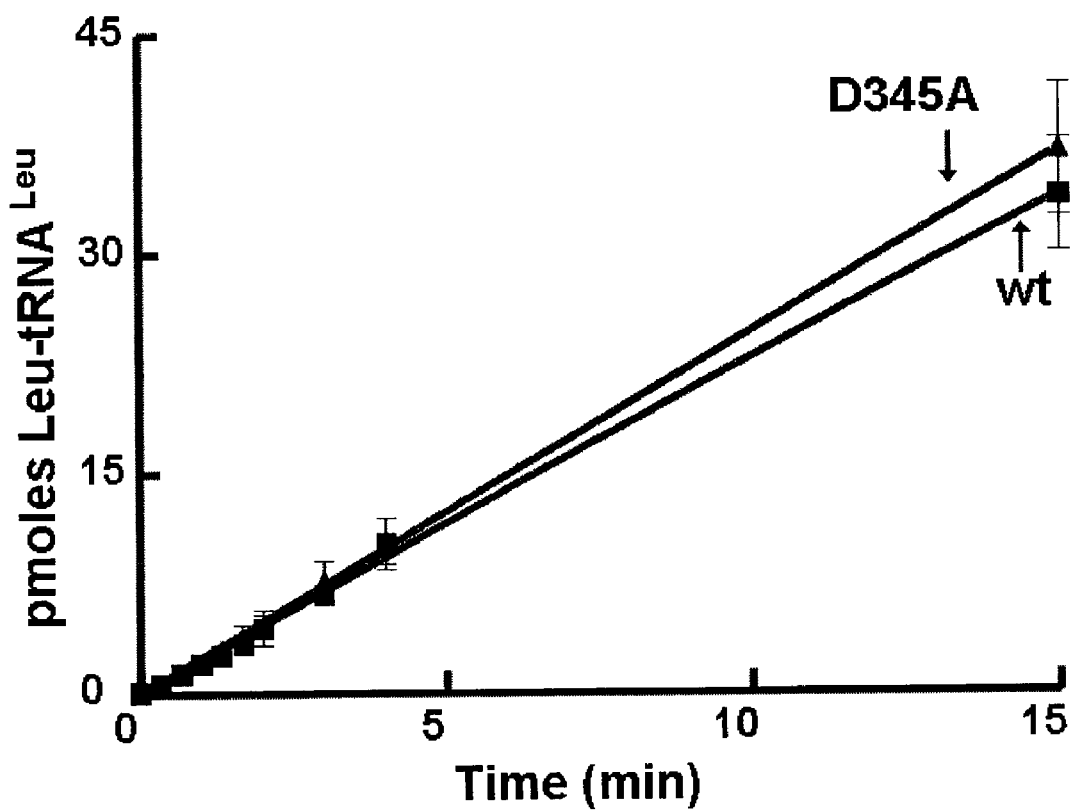
FIG. 18 is a graph of aminoacylation of tRNA$^{Leu}$ with leucine by *E. coli* wild-type LeuRS and a CP1-based mutant LeuRS, wherein symbols representing aminoacylation activity by wild-type and mutant are: wild-type (wt), solid square; D345A, solid triangle.

Primary sequence alignments of LeuRS, IleRS, and ValRS enzymes from prokaryotic and also eukaryotic cytoplasmic and mitochondrial origins identified a completely conserved aspartic acid within the CP1 domain that is also found in IleRS and ValRS (FIG. 12). In one embodiment of the present invention, this aspartic acid was changed to an alanine in *E. coli* (ecD345A) and *S. cerevisiae* cytoplasmic LeuRSs (ycD419A). The mutant and wild-type enzymes from *S. cerevisiae* and *E. coli* were isolated by affinity chromatography via an N-terminal six-histidine tag. Each of the purified mutant enzymes aminoacylated tRNA$^{Leu}$ with leucine at a significant, but slightly reduced activity compared to the wild-type enzymes (FIGS. 13 and 18).

Figure 14:
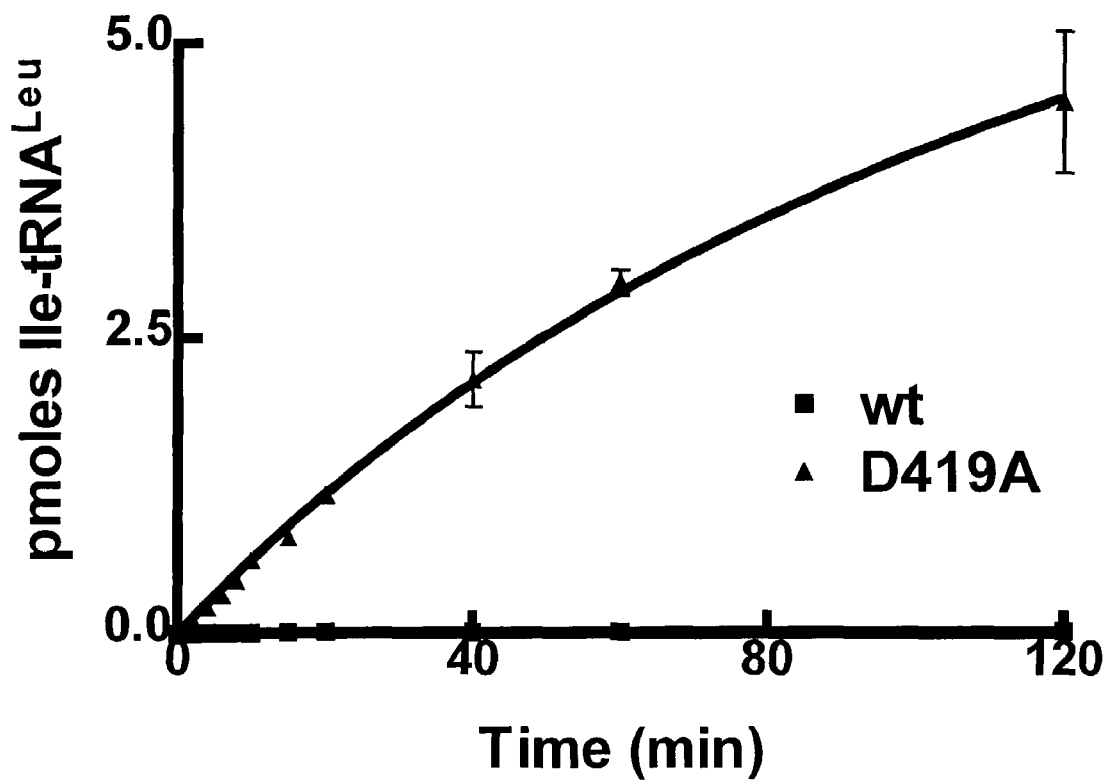
FIG. 14 is a graph of isoleucylation of tRNA$^{Leu}$ by yeast cytoplasmic wild-type and D419A mutant LeuRSs, wherein closed squares and triangles represent isoleucylation activity by wild-type and mutant LeuRSs respectively and error bars are indicated.
Figure 15:
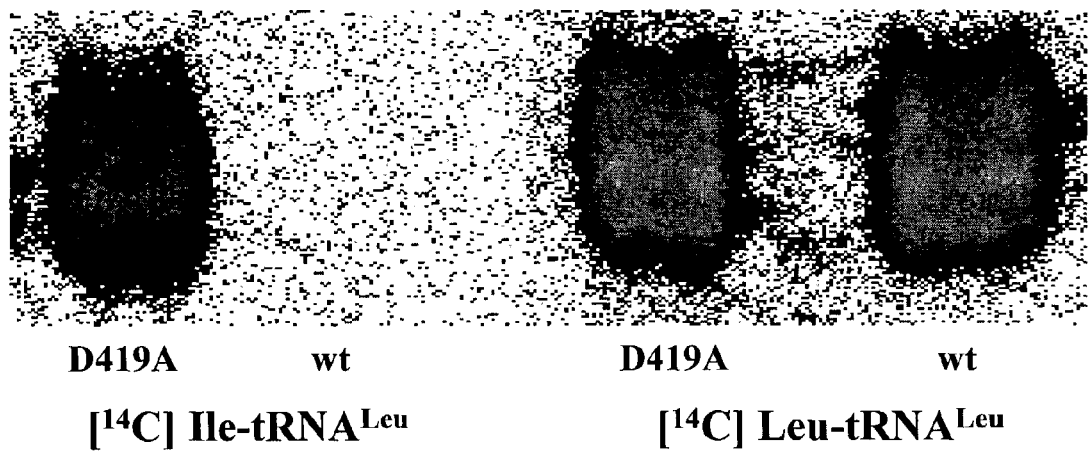
FIG. 15 is an acid gel phosphorimage of leucylated and isoleucylated tRNA$^{Leu}$ by yeast cytoplasmic wild-type and D419A mutant LeuRSs, wherein acid gel electrophoresis was used to isolate [$^{14}$C]-leucine-tRNA$^{Leu}$ and [$^{14}$C]-isoleucine-tRNA$^{Leu}$ such that leucylated tRNA$^{Leu}$ is demonstrated on right and misacylated Ile-tRNA$^{Leu}$ is demonstrated on left.
Figure 19:
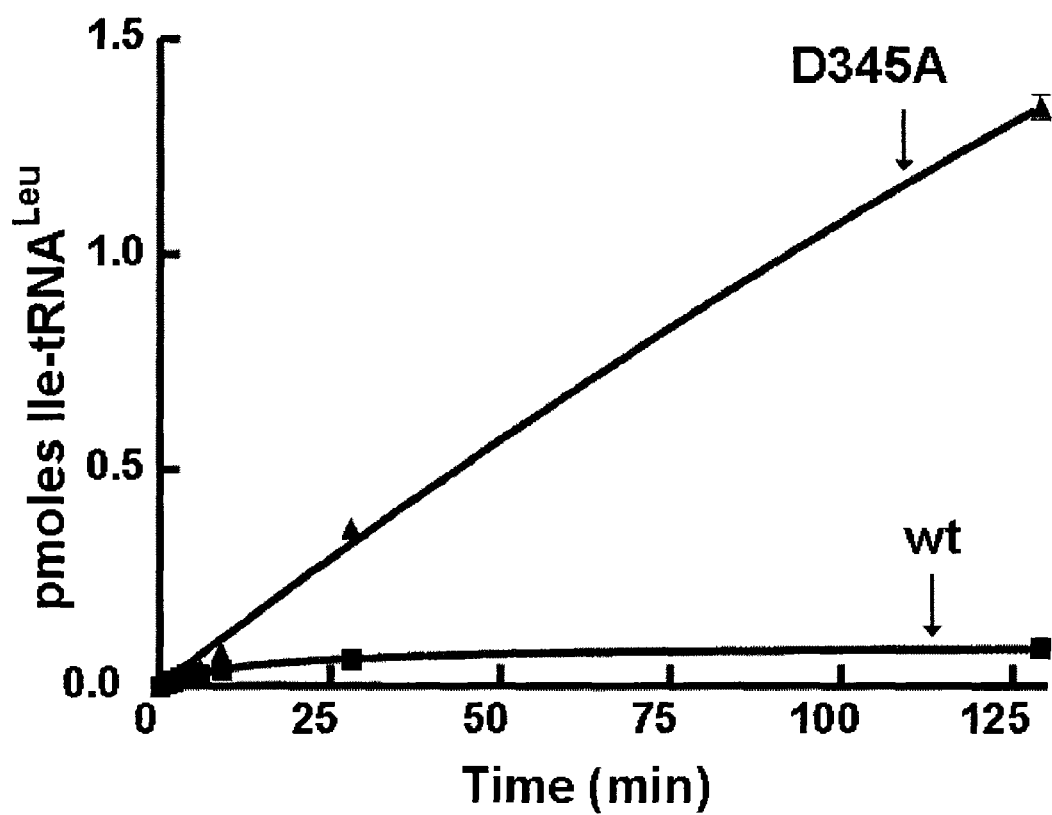
FIG. 19 is a graph of misaminoacylation of tRNA$^{Leu}$ with isoleucine by *E. coli* wild-type LeuRS and a CP1-based mutant LeuRS, wherein symbols representing aminoacylation activity by wild-type and mutant are: wild-type (wt), solid square; D345A, solid triangle.

The CP1-based aspartic acid mutant LeuRSs were tested for isoleucylation activity by isolating tRNA linked to [$^3$H]-isoleucine via trichloroacetic acid precipitation followed by washing. While neither the wild-type *S. cerevisiae* cytoplasmic and *E. coli* LeuRSs yielded mischarged tRNA$^{Leu}$, both the composition invention ycD419A and ecD345A LeuRSs stably generated isoleucine misaminoacylated to tRNA$^{Leu}$ (Ile-tRNA$^{Leu}$) (FIGS. 14 and 19). Correctly charged and mischarged tRNA were separated by acid gel electrophoresis (Varshney et al, 1991). FIG. 15 shows that ycWT and ycD419A yielded similar levels of correctly charged tRNA$^{Leu}$. Consistent with the isoleucine-mischarging activity based on TCA precipitation of tRNA (FIG. 14), the acid gel in FIG. 15 shows that the mutant ycD419A enzyme stably produced tRNA$^{Leu}$ linked to isoleucine. The wild-type enzyme failed to yield a detectable band representing the mischarged Ile-tRNA$^{Leu}$. The production levels of Ile-tRNA$^{Leu}$ compared to Leu-tRNA$^{Leu}$ are decreased as would be expected since LeuRS misactivates isoleucine less efficiently than leucine. Incorporation of methionine into the aminoacylation assay with the mutants ycD419A (FIG. 16) and ecD345A (FIG. 20) followed by either gel analysis or TCA-precipitation recovery of the tRNA showed that both mutants formed Met-tRNA$^{Leu}$. As found with the isoleucine mischarging activity, the level of methionylation activity was significantly lower than that of Leu-tRNA$^{Leu}$ production which would correspond to a relative decrease in activation. The combined mischarging phenotypes of methionine and isoleucine by both *S. cerevisiae* cytoplasmic and *E. coli* LeuRSs support that the conserved aspartic acid plays a critical role in the amino acid editing active site.

Figure 21:
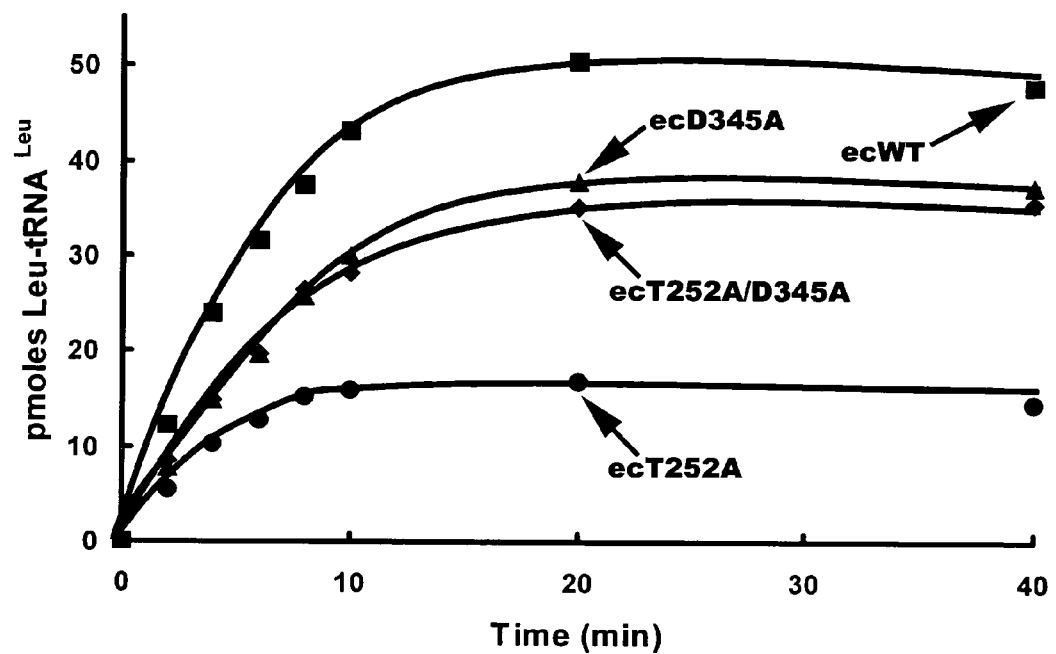
FIG. 21 depicts a leucylation assay of *E. coli* crude tRNA$^{Leu}$ by wild-type (WT) and mutant *E. coli* LeuRSs, wherein wherein symbols represent aminoacylation activity of *E. coli* crude tRNA$^{Leu}$ with ecWT LeuRS (solid square), ecD345A LeuRS (solid triangle), ecT252A LeuRS (solid circle), and ecT252A/D345A LeuRS (solid diamond)
Figure 22:
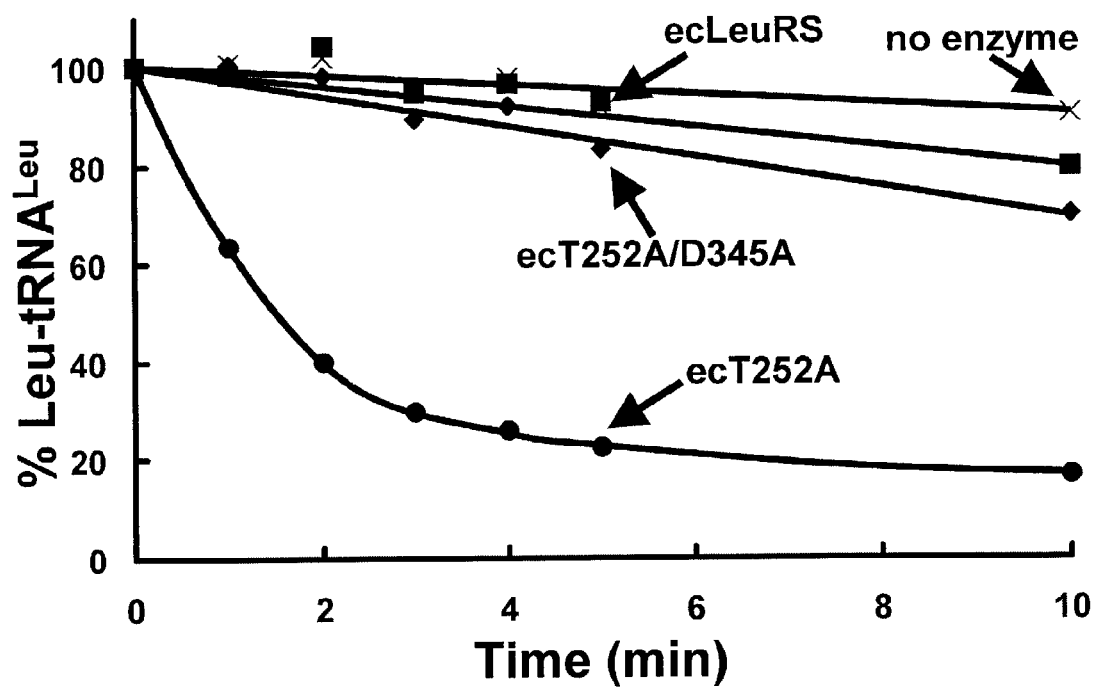
FIG. 22 depicts deacylation of correctly aminoacylated Leu-tRNA$^{Leu}$ by wild-type and mutant *E. coli* LeuRSs, wherein symbols are: ecLeuRS (solid square), ecT252A LeuRS (solid circle), ecT252A/D345A LeuRS (solid diamond), and a control reaction that lacks enzyme (x)
Figure 23:
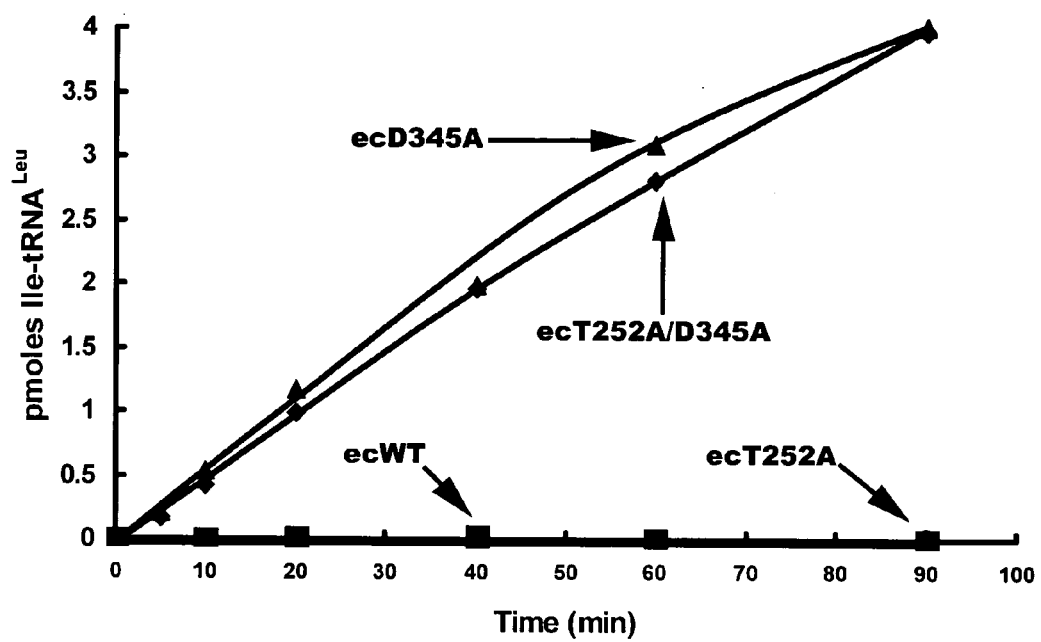
FIG. 23 depicts an isoleucylation assay of *E. coli* crude tRNA by wild-type and mutant *E. coli* LeuRSs, wherein the symbols are ecWT LeuRS (solid square), ecD345A LeuRS (solid triangle), ecT252A LeuRS (solid circle), and ecT252A/D345A LeuRS (solid diamond)

The *E. coli* leucyl-tRNA synthetase Thr 252 residue was shown to be a fine discriminant for molecular recognition that blocks leucine from binding to the editing active site (Mursinna et al., 2001). Since *E. coli* LeuRS T252A mutation recognizes an additional substrate (Leu-tRNA$^{Leu}$), it provided a unique opportunity to test the effects of the conserved aspartic acid in post-transfer editing of an alternate substrate. The *E. coli* T252A mutant LeuRS was combined with the ecD345A mutation (ecT252A/D345A) to further analyze the latter's effect on catalysis and the overall editing reaction. While the ecT252A mutation decreases apparent leucylation of tRNA$^{Leu}$, ecT252A/D345A restores activity to the level of the ecD345A LeuRS mutant that is also similar to wild-type enzyme (FIG. 21). The *E. coli* mutants as well as the wild-type enzymes were tested for their ability to hydrolyze correctly charged Leu-tRNA$^{Leu}$ (FIG. 22). As would be expected, the ecD345A single mutation failed to edit Leu-tRNA$^{Leu}$. As FIG. 22 illustrates, ecD345A restores leucylation activity of ecT252A mutant by preventing the hydrolysis of Leu-tRNA$^{Leu}$. The ecD345A mutation was also efficient in disrupting binding in the altered editing pocket of the ecT252A modification to allow mischarging of isoleucine to tRNA$^{Leu}$ (FIG. 23). These combined results support that the universally conserved aspartic acid plays a key role in the overall editing reaction.

Figure 24:
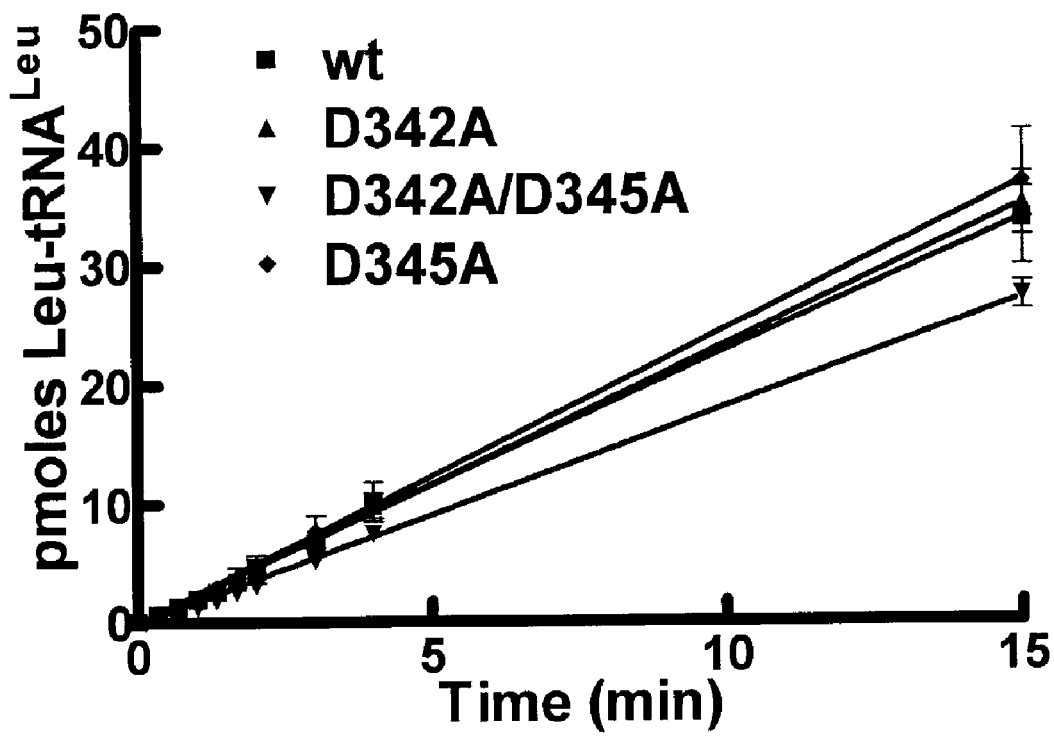
FIG. 24 depicts the leucylation of *E. coli* crude tRNA with leucine by wild-type and mutant *E. coli* LeuRSs, wherein each reaction was repeated 3 times and averaged and the symbols used are: wild-type LeuRS (solid square), D342A LeuRS (solid triangle), D345A LeuRS (solid diamond), and D342A/D345A LeuRS (inverted solid triangle)
Figure 25:
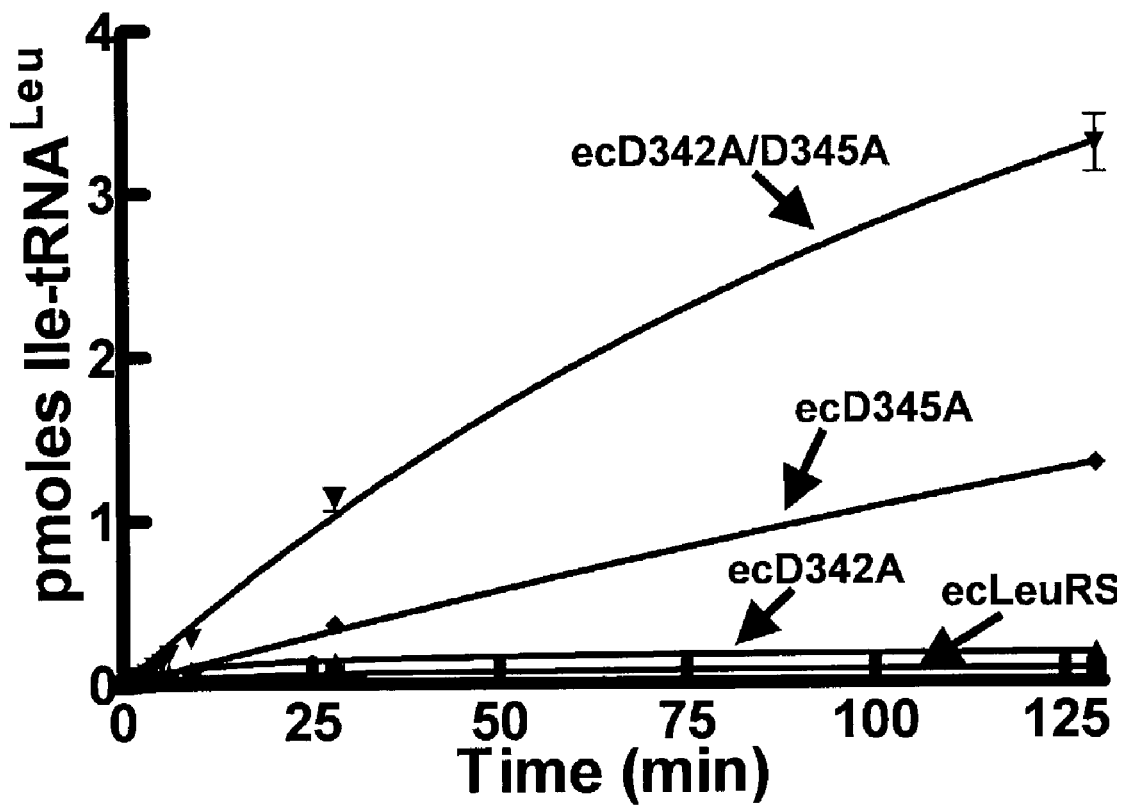
FIG. 25 depicts an example of mischarging activity of wild-type and editing-defective *E. coli* LeuRS mutants with isoleucine, wherein the misaminoacylation reaction was repeated 3 times and averaged and the symbols represent wild-type ecLeuRS (solid square), ecD342A LeuRS (solid triangle), ecD345A LeuRS (solid diamond), and ecD342A/D345A LeuRS (inverted solid triangle)
Figure 26:
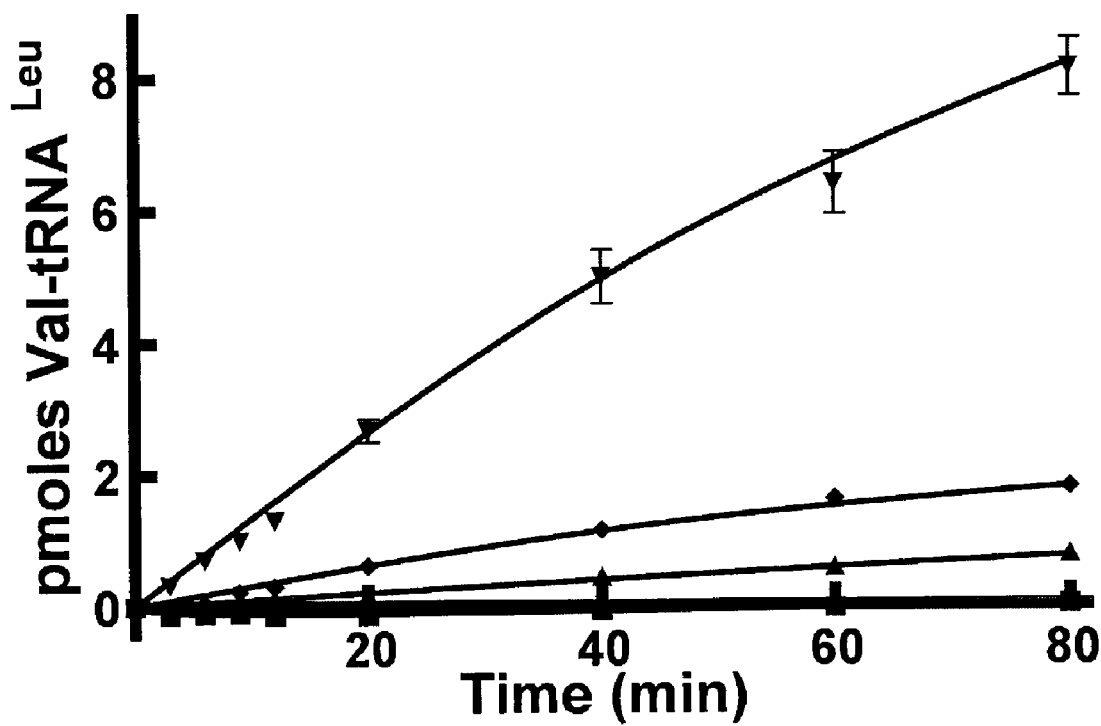
FIG. 26 depicts an example of mischarging activity of wild-type and editing-defective *E. coli* LeuRS mutants with valine, wherein misaminoacylation was an average of three repeat experiments and symbols represent wild-type LeuRS (solid square), D342A LeuRS (solid triangle), D345A LeuRS (solid diamond), and D342A1D345A LeuRS (inverted solid triangle)
Figure 27:
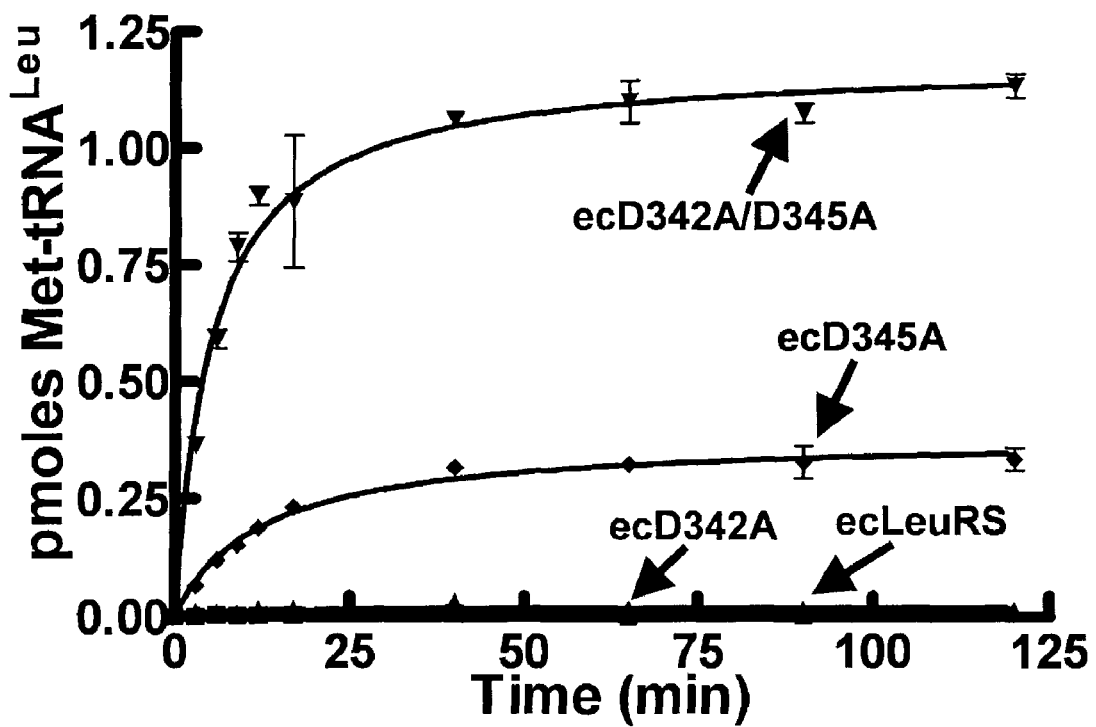
FIG. 27 depicts an example of mischarging activity of wild-type and editing-defective *E. coli* LeuRS mutants with methionine, wherein misaminoacylation was an average of 3 repeat experiments and symbols represent wild-type ecLeuRS (solid square), ecD342A LeuRS (solid triangle), ecD345A LeuRS (solid diamond), and ecD342A/D345A LeuRS (inverted solid triangle)
Figure 28:
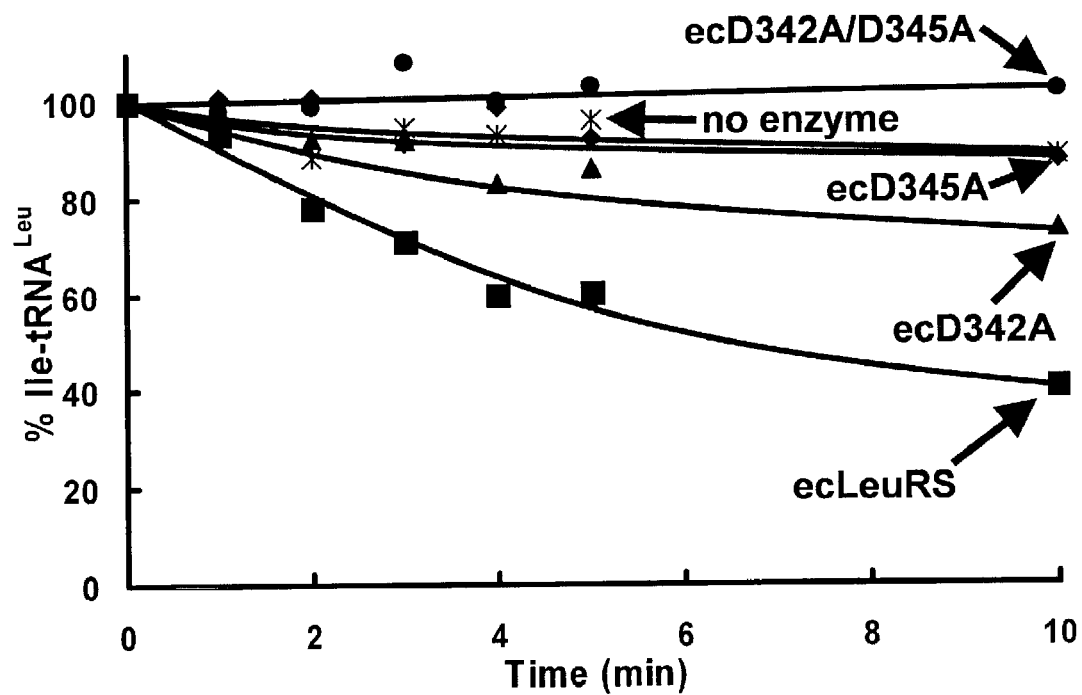
FIG. 28 depicts hydrolytic post-transfer editing of mischarged Ile-tRNA$^{Leu}$ by *E. coli* LeuRS, wherein symbols represent editing activity are: wild-type ecLeuRS (solid square), ecD342A LeuRS (solid triangle), ecD345A LeuRS (solid diamond), ecD342A/D345A LeuRS (solid circle), and no enzyme control (asterisk)
Figure 51:
FIG. 51 depicts an overlay of the homology modeled E. coli LeuRS CP1 domain and the crystal structure of T. thermophilus ValRS CP1 domain, wherein the E. coli LeuRS ribbon diagram (gray, green if in color) overlayed with the T. thermophilus ValRS (light gray, yellow if in color) shows the acceptor stem of the tRNA (black, blue if in color) entering the amino acid editing active site is in close proximity to the highly conserved aspartic acid at position 342 in E. coli LeuRS and the absolutely conserved aspartic acid at position 345 in E. coli LeuRS. The diagram also demonstrated the conserved amino acids are conserved structurally.

Sequence alignments of prokaryotic and eukaryotic mitochondrial LeuRSs along with the highly homologous ValRSs identified a highly conserved aspartic acid (D342 in E. coli LeuRS) in ValRS and prokaryotic and mitochondrial LeuRSs that is nearby the universally conserved aspartic acid (FIG. 50). Both aspartic acids overlap in the tertiary structure of T. thermophilus LeuRS (Cusack et al., 2000) and ValRS (Fukai et al., 2000) (FIG. 51). In one embodiment of the present invention, alanine was substituted at the aspartic acid site in E. coli LeuRS (D342A). A double mutation to substitute each of the two conserved aspartic acids (D342A/D345A) was also created. The E. coli wild-type, D342A, D345A, and D342A/D345A mutants were purified to homogeneity via affinity chromatography using an N-terminal six-histidine tag. The leucylation activity for each of the single mutants was comparable to the wild-type LeuRS. The double mutant retained significant aminoacylation activity although it was slightly decreased (FIG. 24). The composite invention D342A/D345A double mutant LeuRS was able to produce significant quantities of misaminoacylated isoleucyl-tRNA$^{Leu}$, valyl-tRNA$^{Leu}$, and methionyl-tRNA$^{Leu}$ (FIG. 25-27). Hydrolytic editing activity assays demonstrated that the D342AID345A double mutant LeuRS editing activity was abolished (FIG. 28).

In one embodiment of the present invention, a triple mutation was also created that combined the D342A, D345A, and T252Y mutations in E. coli LeuRS (T252Y/D342A/D345A). The composite invention lacked amino acid editing activity. Combining multiple editing-defective mutations would decrease the possibility of reversion mutations due to natural mutagenesis when the composite invention is used in vivo.

Figure 34:
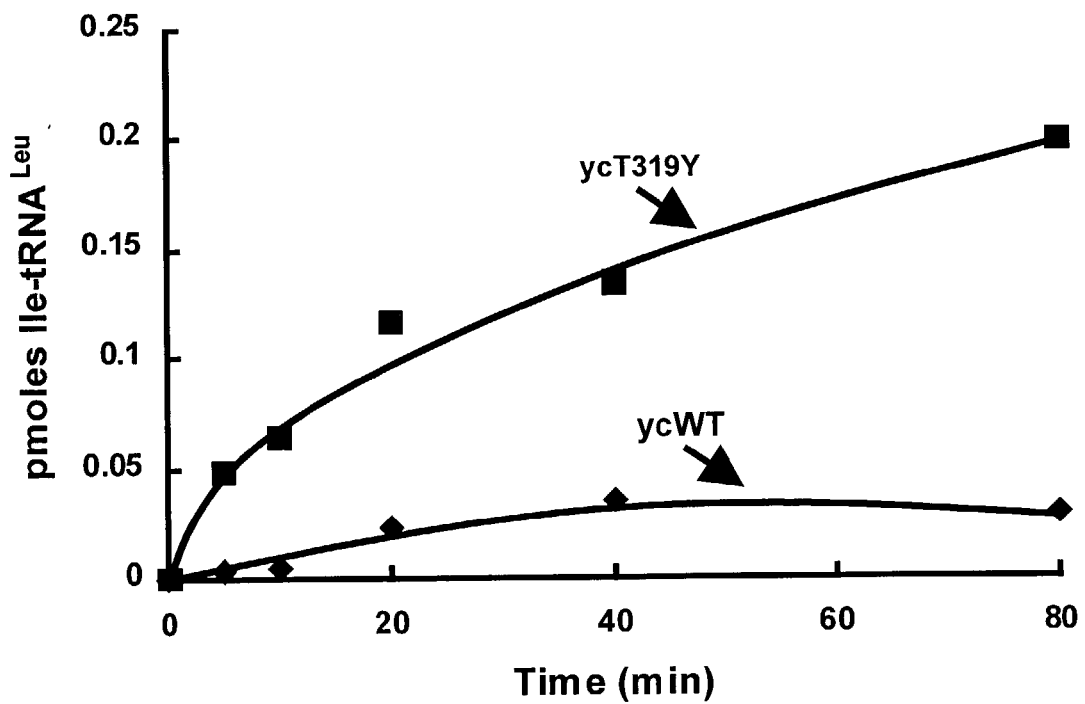
FIG. 34 is a graph of misaminoacylation of tRNA$^{Leu}$ with isoleucine by yeast cytoplasmic wild-type LeuRS and a CP1-based mutant LeuRS, wherein symbols represent aminoacylation activity by wild-type and mutant LeuRS as follows: wild-type (ycWT), closed diamond; ycT319Y, closed square.
Figure 38:
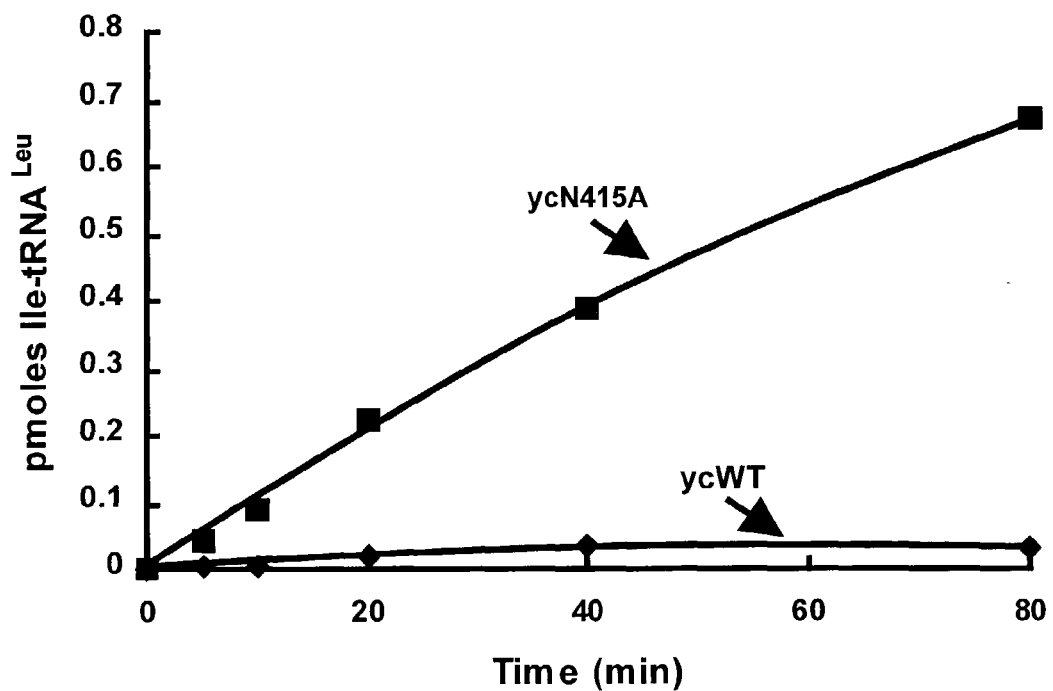
FIG. 38 is a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycN415A, closed square.
Figure 44:
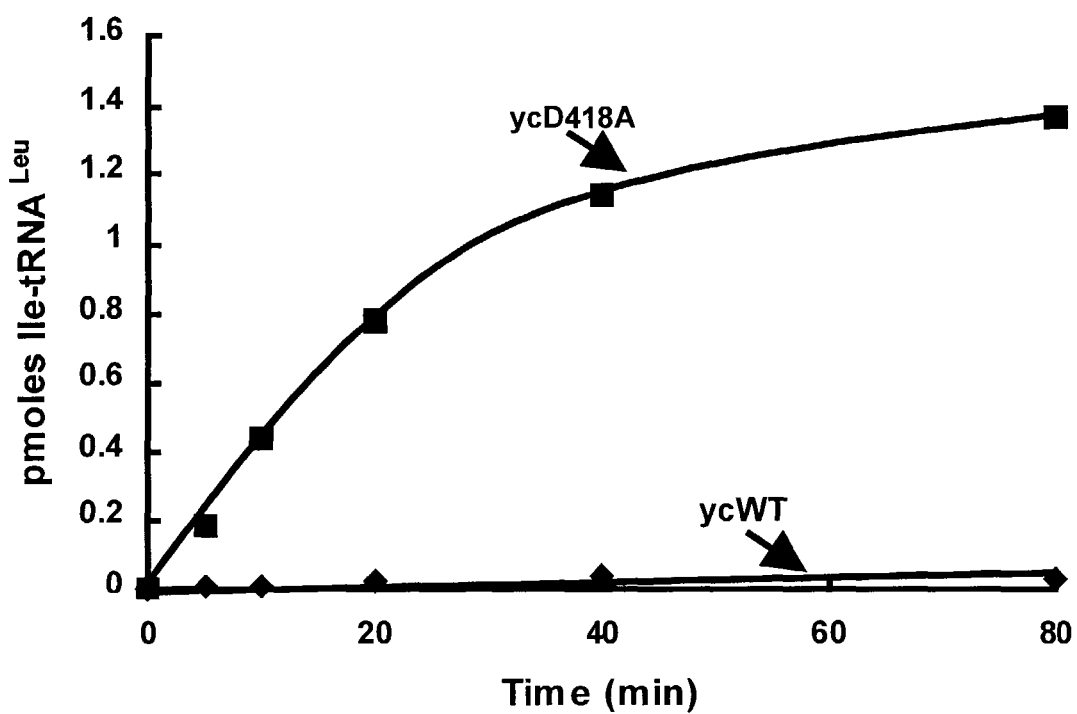
FIG. 44 s a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycD418A, closed square.

In several embodiments of the present invention, editing-defective mutations in S. cerevisiae LeuRS were created and included substitution of an aspartic acid at position 418 by an alanine (D418A), substitution of an asparagine at position 415 by an alanine (N415A), and substitution of a threonine at position 319 by a tyrosine (T319Y). Each of the composite single mutant inventions in S. cerevisiae LeuRS, which included the T319Y, N415A, and D418A mutants exhibited decreased amino acid editing activities (FIGS. 34, 38, and 44). The D419A mutation was combined with each of these single mutations in S. cerevisiae LeuRS, and also substitution of a serine at position 416 by an alanine (S416A), to create the double mutants D418A/D419A, S416A/D419A, N415A/D419A, and T319Y/D419A LeuRSs. Each of the composite inventions T319Y/D419A mutant LeuRS, N415A/D419A mutant LeuRS, S416A/D419A mutant LeuRS, and D418A/D419A mutant LeuRS had significantly diminished editing activities FIGS. (36, 40, 42, and 46). Combining multiple editing-defective mutations in these composite inventions would decrease the possibility of reversion mutations due to natural mutagenesis when the composite invention is used in vivo.

Figure 32:
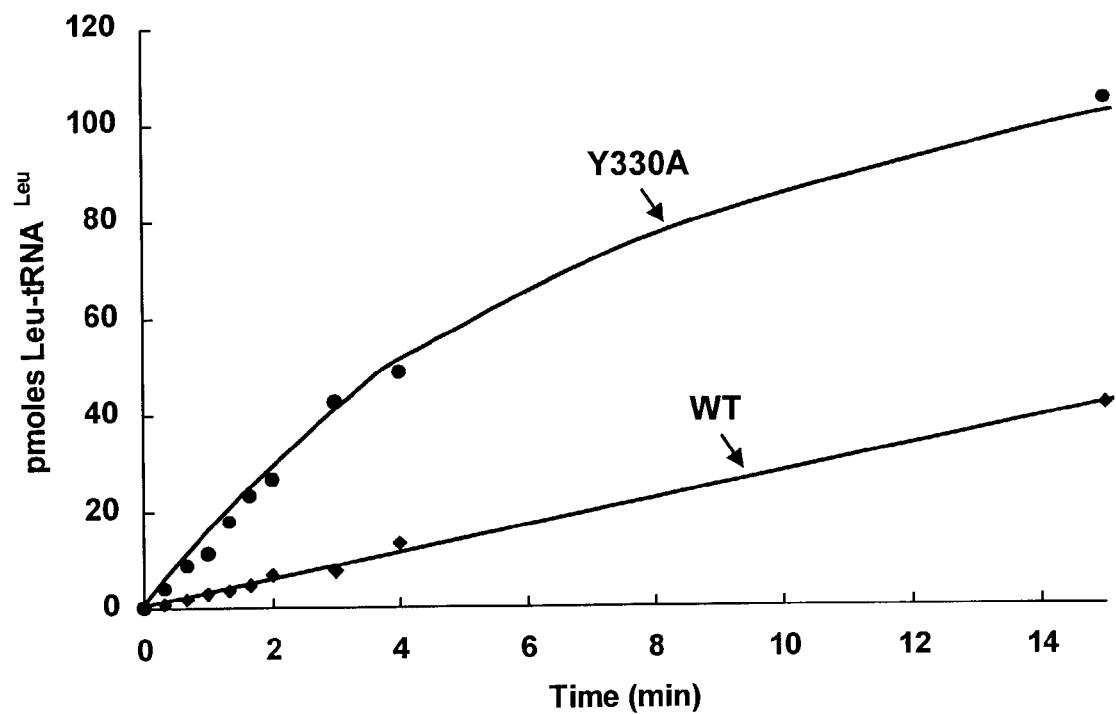
FIG. 32 is a graph of aminoacylation of tRNA$^{Leu}$ with leucine by *E. coli* wild-type LeuRS and a CP1-based mutant LeuRS, wherein symbols representing aminoacylation by wild-type and mutant LeuRS are: wild-type (WT), closed diamond; Y330A, closed circle.

High expression of recombinant proteins has shown that norvaline is substituted for leucine during protein synthesis (Apostol et al., 1987). Identification of a more specific leucyl-tRNA synthetase, which could discriminate more efficiently leucine from noncognate amino acids, would enable more accurate expression of pure recombinant proteins in E. coli. In one embodiment of the present invention, Tyr 330 of E. coli LeuRS was substituted by an alanine (Y330A). The composite invention mutant Y330A E. coli LeuRS enzyme was shown to aminoacylate leucine to tRNA$^{Leu}$ at higher levels relative to wild type (FIG. 32). A triple mutation that combined the Y330A, D342A, and D345A mutations in E. coli LeuRS (Y330A/D342A/D345A) was created. The composite invention E. coli LeuRS Y330A/D342A/D345A mutant was determined to yield significantly higher levels of misaminoacylated isoleucine-tRNA$^{Leu}$ compared to any of the E. coli mutants generated that exhibited amino acid editing defects. Combining multiple editing-defective mutations would decrease the possibility of reversion mutations due to natural mutagenesis when the composite invention is used in vivo.

Figure 29:
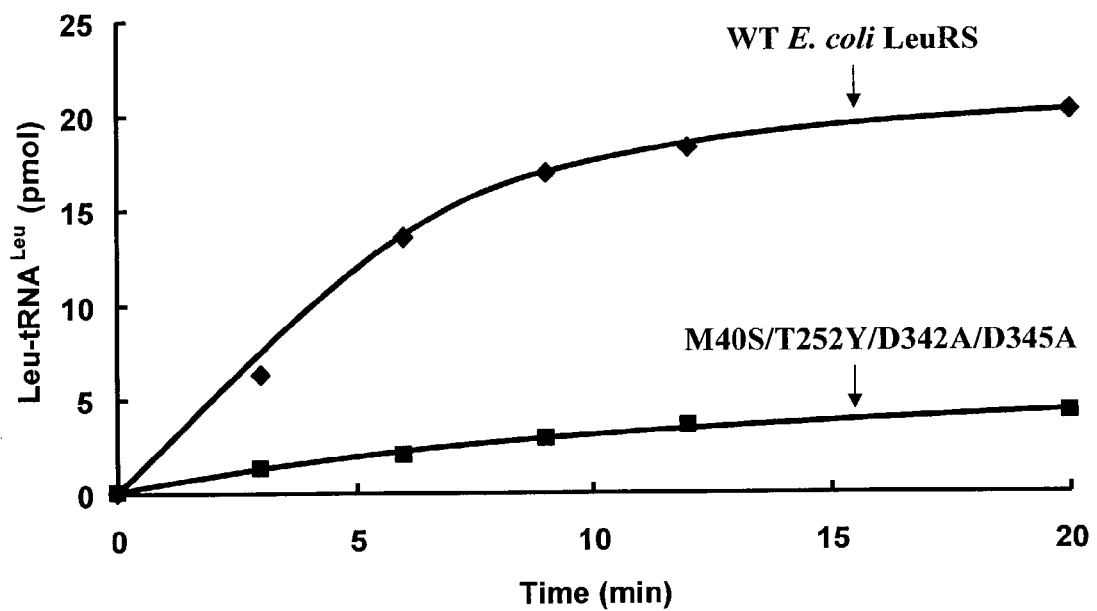
FIG. 29 is a graph of aminoacylation of tRNA$^{Leu}$ with leucine by wild-type and an aminoacylation active site mutant LeuRS that also has an inactivated amino acid editing activity. The symbols representing aminoacylation activity by wild-type and mutant LeuRS are: wild-type (WT) *E. coli* LeuRS, closed diamond; M40S/T252Y/D342A/D345A LeuRS, closed square.
Figure 30:
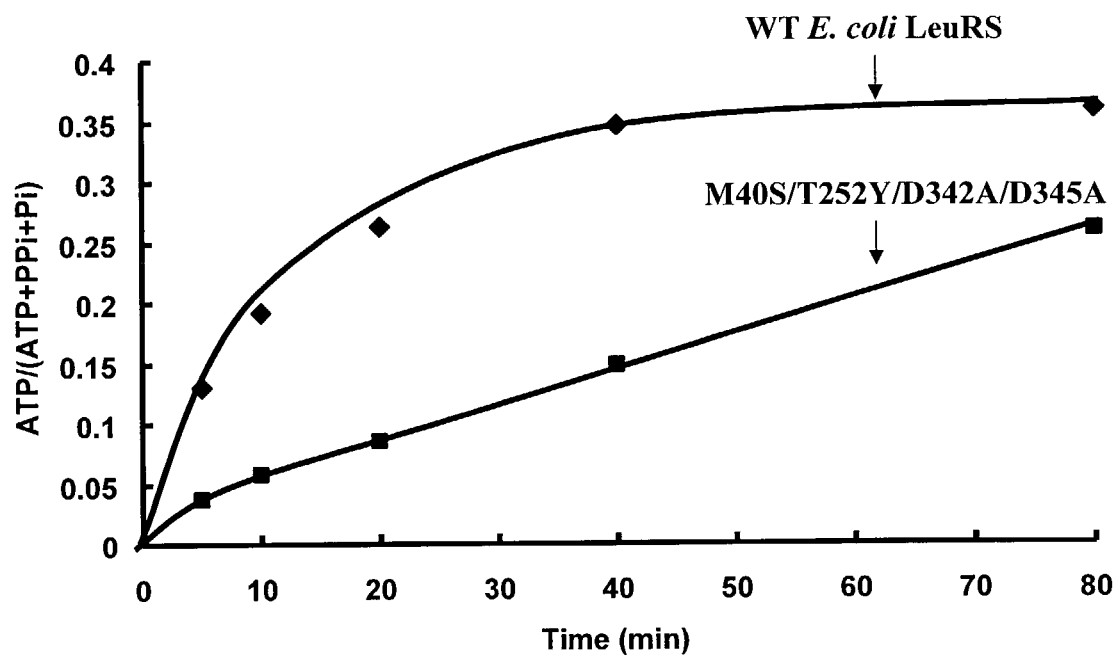
FIG. 30 is a leucine-dependent PP$_i$ exchange activity for wild-type and an aminoacylation active site mutant LeuRS that also has an inactivated amino acid editing activity, wherein aliquots of 2 μl of the reaction mixture were quenched directly on the TLC plate at specific time points as indicated. ATP was chromatographically separated from PP$_i$ (and background phosphate (P$_i$)) and analyzed by phosphorimaging. The data was converted quantitatively to determine ATP formation. The symbols are: wild-type (WT) *E. coli* LeuRS, closed diamond; M40S/T252Y/D342A/D345A LeuRS, closed square.
Figure 31:
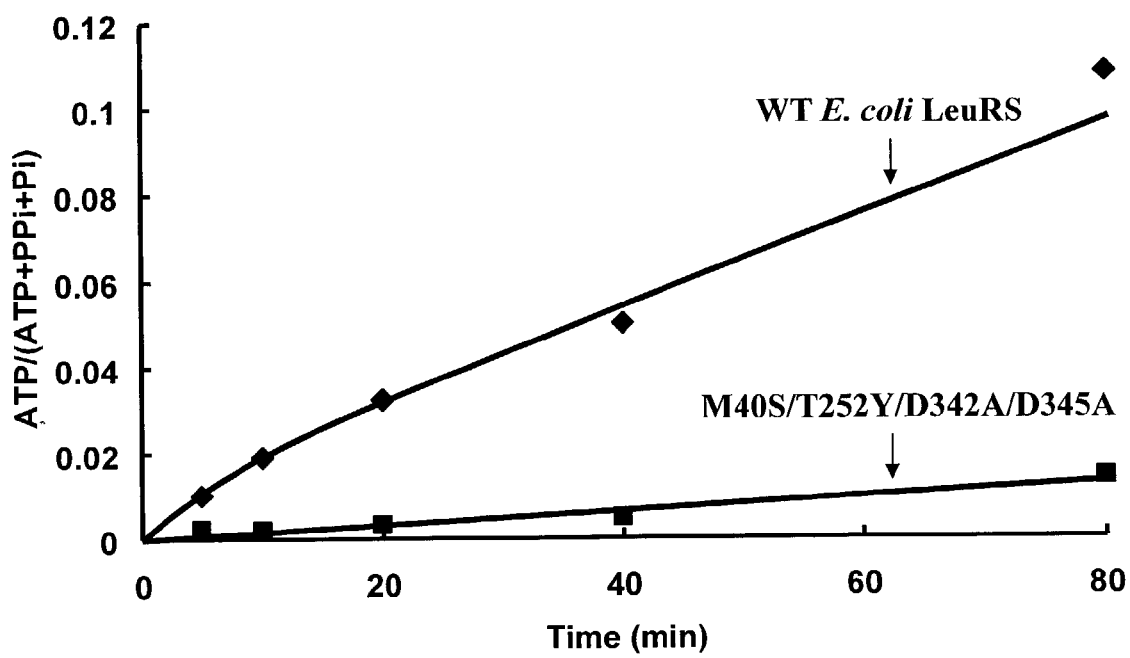
FIG. 31 depicts norvaline-dependent PP$_i$ exchange activity for wild-type and an aminoacylation active site mutant LeuRS that also has an inactivated amino acid editing activity, wherein aliquots of 2 μl of the reaction mixture were quenched directly on the TLC plate at specific time points as indicated. ATP was chromatographically separated from PP$_i$ (and background phosphate (P$_i$)) and analyzed by phosphorimaging. The data was converted quantitatively to determine ATP formation. The symbols are: wild-type (WT) *E. coli* LeuRS, closed diamond; M40S/T252Y/D342A/D345A LeuRS, closed square.

The T. thermophilus LeuRS crystal structure (Cusack et al., 2000) and the E. coli LeuRS homology model (Lee and Briggs, 2002) were used to identify active site residues that were in close proximity to the leucine side chain in the aminoacylation active site. In one embodiment of the present invention, the methionine residue at position 40 was substituted by a serine in E. coli LeuRS (M40S). The mutation was combined with multiple other mutations (T252Y/D342A/D345A) in the CP1 domain of E. coli LeuRS that resulted in an editing defect. Aminoacylation of leucine to tRNA$^{Leu}$ was decreased relative to the wild type enzyme (FIG. 29). Amino acid-dependent pyrophosphate exchange activity showed that leucine discrimination relative to norvaline discrimination was increased by the composite invention mutant M40S E. coli LeuRS (FIGS. 30 and 31). TABLE 1 illustrates some of the various mutations obtained from E. coli and S. cerevisiae (cytoplasmic and mitochondrial) as further described below, from E. coli and S. cerevisiae (cytoplasmic and mitochondrial) as further described below, while TABLE 2 illustrates the wild-type enzyme mutations.

TABLE 1

List of some identified mutations.

| | Plasmid Name | Presence | Nucl., Prot. | Phenotype |
|---|---|---|---|---|
| S. cerevisiae (cytoplasmic) Mutations | | | | |
| ycT319Y-2 | pHAPPY1-1-1-8 | Y | NP | Low mischarging |
| ycT319Y/D419A-1 | pHAPPY1-1-1-9 | Y | NP | High mischarging |
| ycN415A-1 | pHAPPY1-1-1-55 | Y | NP | Low mischarging |
| ycN415A/D419A-5 | pHAPPY1-1-1-59 | Y | NP | High mischarging |
| ycS416A/D419-1 | pHAPPY1-1-1-57 | Y | NP | High mischarging |
| ycD418A-1 | pHAPPY1-1-1-56 | Y | NP | Moderate mischarging |
| ycD418A/D419-1 | pHAPPY1-1-1-58 | Y | NP | High mischarging |
| ycD419A-3/1 | p32-AMW1 | Y | NP | High mischarging |
| S. cerevisiae (mitochondrial) Mutations | | | | |
| ymD357A-1 | pHAPPY3-1-1-48 | Y | NP | Moderate mischarging |
| E. coli Mutations | | | | |
| ecT248A | pMURe5 | N | NP | Low mischarging |
| ecT248A/T252V | pMURed13 | N | NP | Low mischarging |
| ecT252A | pMURe10 | Y | NP | Edits cognate leucine |
| ecT252F | pMURe21 | Y | NP | Moderate mischarging |
| ecT252Y | pMURe22 | Y | NP | Moderate mischarging |

TABLE 1-continued

List of some identified mutations.

| Mutations | Plasmid Name | Presence | Nucl., Prot. | Phenotype |
|---|---|---|---|---|
| ecT252Y/D345A | pHAPPY2-1-1-22 | | NP | Moderate mischarging |
| ecT252Y/D342A/D345A-1 | pHAPPY2-1-1-23 | | NP | High mischarging |
| ecT252Y/Y330A/D342A/D345A-3 | pHAPPY2-1-1-24 | | NP | High mischarging |
| ecD342A | pMURe15 | Y | NP | Low mischarging |
| ecD345A | pHAPPY2-1-1-28 | Y | NP | Moderate Mischarging |
| ecD342A/D345A | pHAPPY2-1-1-29 | Y | NP | High mischarging |
| ecT252A/D345A | pHAPPY2-1-1-19 | Y | NP | Moderate mischarging |
| ecY330A | pMURe13 | Y | NP | Increased leucylation |
| ecY330A/D342A/D345A | pMurset1 | Y | NP | High mischarging |
| ecM40S/T252Y/D342A/D345A-2 | pHAPPY2-1-1/3-46 | Y | NP | Altered amino acid specificity |
| ecT252A/D342A/D345A | pHAPPY2-1-1-20 | N | NP | High mischarging |
| ecT252A/D342A | | N | NP | Low mischarging |
| ecR344A | pMURe18 | | | Low mischarging |
| ecR249T | pYUXIN-1-1 | | | Low mischarging |
| ecD251W | pYUXIN-1-2 | | | Low mischarging |
| ecR249T/D251W | pYUXIN-1-3 | | | Low mischarging |

Abbreviations: Presence = example is present; Y = yes; N = no; NP = nucleic acid or protein.

TABLE 2

Wild-type genes.

| Mutations | Plasmid Name | Presence | Nucl., Prot. | Phenotype |
|---|---|---|---|---|
| *S. cerevisiae* (cytoplasmic) | | | | |
| ycLRS | p32y1-2-3 | N | NP | Wild-type |
| *S. cerevisiae* (mitochondrial) | | | | |
| ymLRS | pYM3174 | N | NP | Wild-type |
| *E. coli* | | | | |
| ecLRS | P15ec3-1 | N | NP | Wild-type |

Abbreviations: Presence = example is present; Y = yes; N = no; NP = nucleic acid or protein.

The *E. coli* LeuRS T252Y Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using the polymerase chain reaction (PCR), the single or multiple mutant leuS gene is then generated using PCR primers that contain the desired T252Y mutation.

Plasmids harboring the LeuRS T252Y mutation are used to transform protein expression strains for recombinant protein production. The LeuRS T252Y mutant is then purified using immobilized metal affinity chromatography and identified by sodium dodecyl sulfate-polyacrylamide gel electrophoresis (SDS-PAGE).

Leucylation activities of tRNA$^{Leu}$ by the LeuRS T252Y mutant are quantitated by scintillation counting (FIG. 9). Its enzymatic activities are compared to wild-type LeuRS enzymatic activities. In the case of the *E. coli* LeuRS T252Y mutant, this editing mutant leucylates tRNA$^{Leu}$ at a similar efficiency to the wild-type protein.

Isoleucylation of tRNA$^{Leu}$ by LeuRS T252Y is quantitated by scintillation counting and is compared to results obtained from experiments performed in parallel using the wild-type LeuRS (FIG. 10). In the case of the *E. coli* LeuRS T252Y mutant protein, the editing mutant aminoacylates tRNA$^{Leu}$ with isoleucine yielding isoleucine-tRNA$^{Leu}$ in contrast to the wild-type protein that exhibits no detectable levels of isoleucylation activity.

Figure 11:
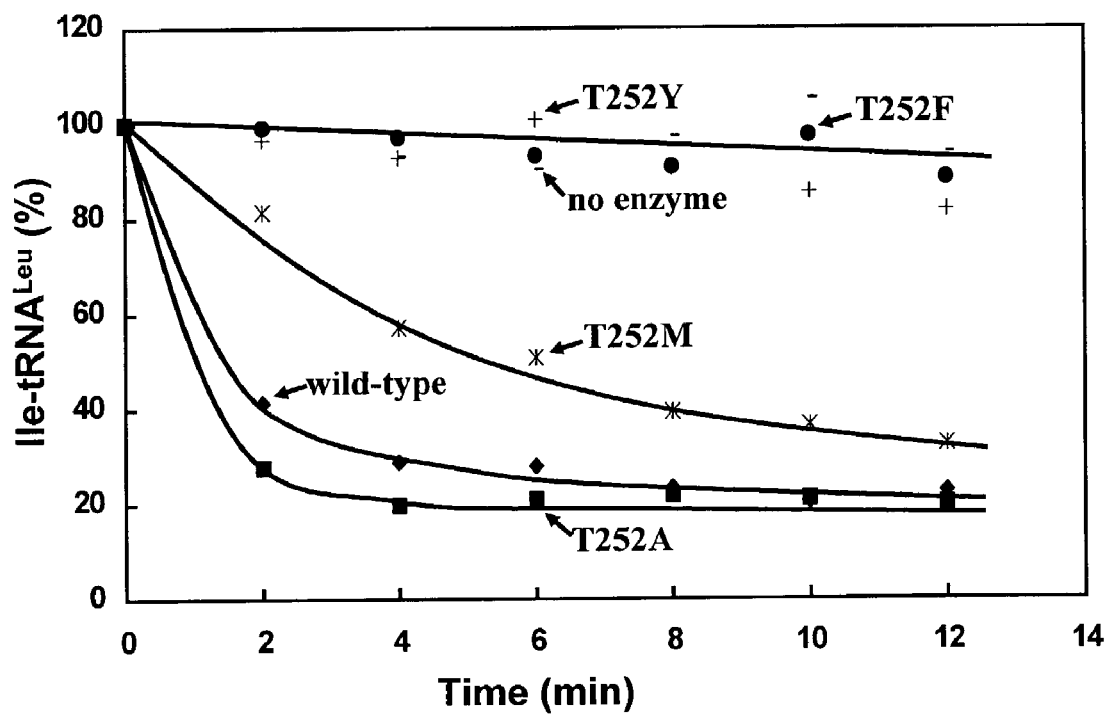
FIG. 11 is a graph of deacylation of isoleucine-tRNA$^{Leu}$ by wild-type and mutant LeuRSs that contain substitutions by amino acids with larger side chains at the conserved Thr 252 residue and symbols are: wild-type LeuRS, closed diamond; T252A LeuRS, closed square; no enzyme control, dash sign; T252M LeuRS, asterisk; T252Y, plus sign; T252F, closed circle.

The hydrolytic editing activity of the LeuRS T252Y mutant is quantitated by scintillation counting and compared with results obtained from experiments performed in parallel using both the wild-type LeuRS and the LeuRS T252A mutant (FIG. 11). In the case of the *E. coli* LeuRS proteins and mutants thereof, both the wild-type and T252A LeuRSs deacylated the mischarged tRNA. In contrast, the LeuRS T252Y mutant did not hydrolyze the misacylated tRNA.

The *E. coli* LeuRS T252F Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using PCR, the single or multiple mutant leuS gene is then generated using PCR primers that contain the desired T252F mutation (Mursinna and Martinis, 2002).

Plasmids harboring the LeuRS T252F mutation are used to transform protein expression strains for recombinant protein production. The LeuRS T252F mutant is then purified using immobilized metal affinity chromatography and identified by sodium dodecyl sulfate-polyacrylamide gel electrophoresis (SDS-PAGE).

Leucylation activities of tRNA$^{Leu}$ by the LeuRS T252F mutant is quantitated by scintillation counting (FIG. 9). Its enzymatic activities are compared to wild-type LeuRS enzymatic activities. In the case of the *E. coli* LeuRS T252F mutant, this editing mutant leucylates tRNA$^{Leu}$ at a similar efficiency to the wild-type protein.

Isoleucylation of tRNA$^{Leu}$ by LeuRS T252F is quantitated by scintillation counting and then is compared to results obtained from experiments performed in parallel using the wild-type LeuRS (FIG. 10). In the case of the *E. coli* LeuRS T252F mutant protein, the editing mutant aminoacylates tRNA$^{Leu}$ with isoleucine yielding isoleucine-tRNA$^{Leu}$ in contrast to the wild-type protein that exhibits no detectable levels of isoleucylation activity.

The hydrolytic editing activity of the LeuRS T252F mutant is quantitated by scintillation counting and is compared with results obtained from experiments performed in parallel using both the wild-type LeuRS and the LeuRS T252A mutant (FIG. 11). In the case of the *E. coli* LeuRS proteins and mutants thereof, both the wild-type and T252A LeuRSs deacylate the mischarged tRNA. In contrast, the LeuRS T252F mutant does not hydrolyze the misacylated tRNA.

The S. cerevisiae Cytoplasmic LeuRS D419A Mutation

Plasmids harboring the wild-type CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired D419A mutation (FIG. 12).

Plasmids harboring the LeuRS D419A mutation are used to transform protein expression strains for recombinant protein production. The LeuRS D419A mutant is then purified using immobilized metal affinity chromatography and identified by sodium dodecyl sulfate-polyacrylamide gel electrophoresis (SDS-PAGE).

Leucylation activities of tRNA$^{Leu}$ by the LeuRS D419A mutant is quantitated by scintillation counting (FIG. 13). Its enzymatic activities are compared to wild-type LeuRS enzymatic activities. In the case of the S. cerevisiae LeuRS D419A mutant, this editing mutant leucylates tRNA$^{Leu}$ at a similar efficiency to the wild-type protein.

Figure 16:
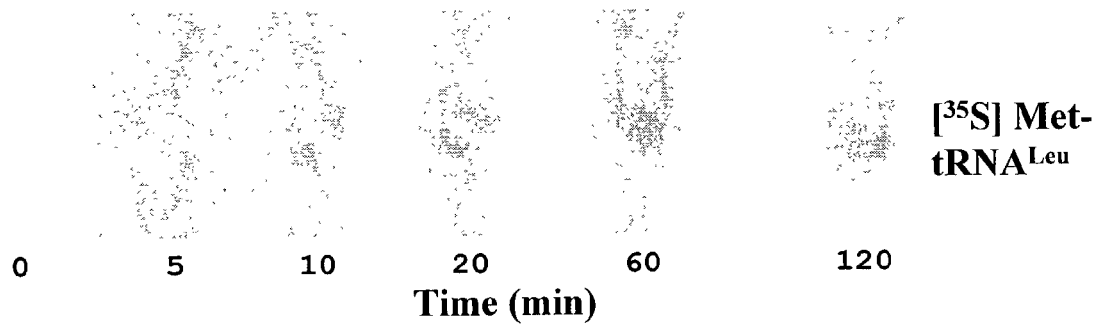
FIG. 16 depicts an acid gel phosphorimage of methionylated tRNA$^{Leu}$ by yeast cytoplasmic D419A mutant LeuRS, wherein acid gel electrophoresis was used to isolate [$^{35}$S]-methionine-tRNA$^{Leu}$ that was misaminoacylated by the mutant D419A LeuRS and aliquots were quenched and loaded directly on the acid gel at indicated time points.

Isoleucylation of tRNA$^{Leu}$ by LeuRS D419A is quantitated by scintillation counting (FIG. 14) and also acid gel electrophoresis (FIG. 15) and then compared to results obtained from experiments performed in parallel using the wild-type LeuRS. In the case of the S. cerevisiae LeuRS D419A mutant protein, the editing mutant aminoacylates tRNA$^{Leu}$ with isoleucine yielding isoleucine-tRNA$^{Leu}$ in contrast to the wild-type protein that exhibits no isoleucylation activity. Acid gel electrophoresis is also used to detect misaminoacylation of methionine by the yeast cytoplasmic D419A mutant LeuRS (FIG. 16).

Figure 17:
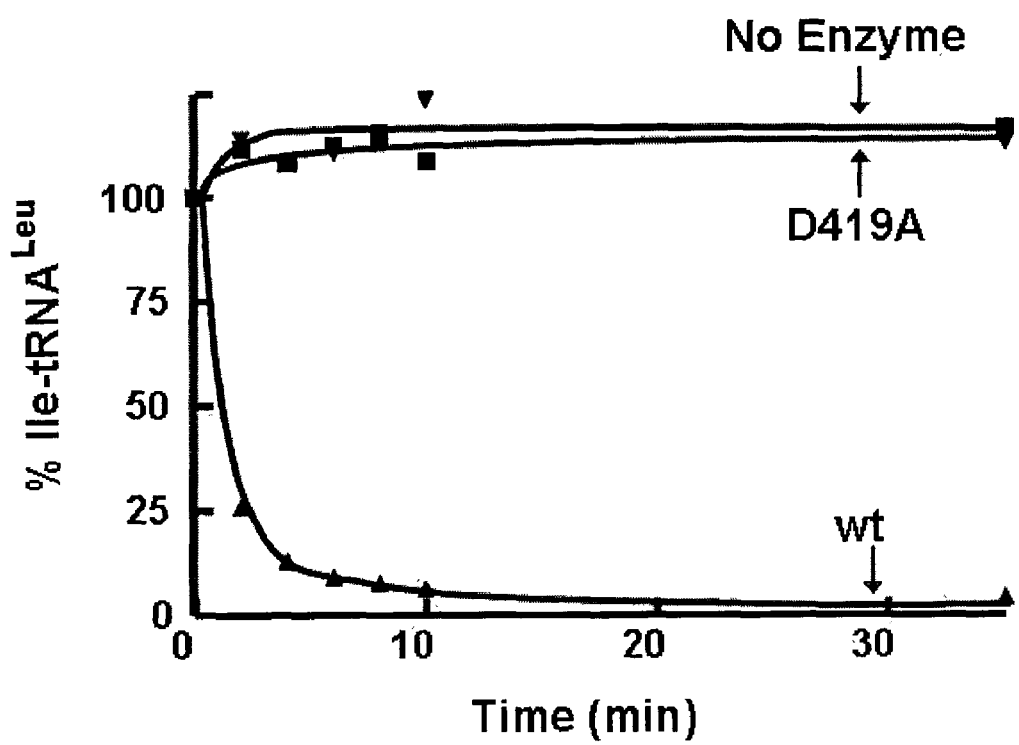
FIG. 17 is a graph of deacylation of isoleucine-tRNA$^{Leu}$ by *S. cerevisiae* wild-type and D419A mutant LeuRSs, wherein symbols are: wild-type (wt) LeuRS, closed triangle; D419A LeuRS, inverted closed triangle; no enzyme control, closed square.

The hydrolytic editing activity of the LeuRS D419A mutant is quantitated by scintillation counting and is compared with results obtained from experiments performed in parallel using the wild-type yeast cytoplasmic LeuRS (FIG. 17). The yeast cytoplasmic wild-type enzyme deacylates the mischarged tRNA. In contrast, the LeuRS D419A mutant does not hydrolyze the misacylated tRNA.

The E. coli D342A and D345A Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using PCR, the single or multiple mutant leuS genes are then generated using PCR primers that contain the desired D342A and/or D345A mutations.

Plasmids harboring the LeuRS with the desired D342A and/or D345A mutations are used to transform protein expression strains for recombinant protein production. The LeuRS D342A, D345A, and D342A/D345A mutants are then purified using immobilized metal affinity chromatography and identified by sodium dodecyl sulfate-polyacrylamide gel electrophoresis (SDS-PAGE).

Replacement of the single aspartic acid at position 342 or 345 in E. coli LeuRS with alanine reduces hydrolytic cleavage of mischarged Ile-tRNA$^{Leu}$ (FIG. 28). Combining the D342A and D345A mutations appears to completely abolish editing and results in significant increases in the misaminoacylation activity of isoleucine, valine, and methionine yielding isoleucine-tRNA$^{Leu}$, valine-tRNA$^{Leu}$, and methionine-tRNA$^{Leu}$ respectively in contrast to the wild-type protein that exhibits no isoleucylation, valylation, and methionylation activities (FIGS. 25-27). This combined mutation suggest that when the universally conserved aspartic acid is replaced with alanine, it still maintains some low undetectable level of hydrolysis. Mutation of just the single aspartic acid at position 342 yielded a decrease in the post-transfer editing. However, this single mutation did not allow for considerable misaminoacylation of isoleucine or valine and no detectable misaminoacylation of methionine (FIGS. 25-27). Using multiple mutations that decrease or abolish amino acid editing activity will reduce the possibility of restoring the mutant LeuRS editing activity via natural mutagenesis when used in vivo within an organism or cell line.

The E. coli D342A and D345A and T252Y Mutation

Plasmids harboring mutant leuS gene from a prokaryotic organism are used to create LeuRS fusion proteins that contain N-terminal six-histidine tags (Martinis and Fox, 1997, Mursinna et al., 2001). Using PCR, the multiple mutant leuS genes are then generated using PCR primers that contain the desired D342A and/or D345A mutations.

Plasmids harboring the LeuRS with the desired D342A and D345A and T252Y mutations are used to transform protein expression strains for recombinant protein production. The LeuRS T252Y/D342A/D345A mutants are then purified using immobilized metal affinity chromatography and identified by sodium dodecyl sulfate-polyacrylamide gel electrophoresis (SDS-PAGE). Combining the T252Y, D342A and D345A mutations appears to completely abolish editing (FIG. 49) and results in significant increases in the misaminoacylation activity of isoleucine yielding isoleucine-tRNA$^{Leu}$ in contrast to the wild-type protein that exhibits no isoleucylation, valylation, and methionylation activities. Using multiple mutations that decrease or abolish amino acid editing activity will reduce the possibility of restoring the mutant LeuRS editing activity via natural mutagenesis when used in vivo within an organism or cell line.

The E. coli LeuRS Y330A Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using PCR, the single or multiple mutant leuS gene is then generated using PCR primers that contain the desired Y330A mutation (Mursinna and Martinis, 2002).

Plasmids harboring the LeuRS Y330A mutation are used to transform protein expression strains for recombinant protein production. The LeuRS Y330A mutant is then purified using immobilized metal affinity chromatography and identified by sodium dodecyl sulfate-polyacrylamide gel electrophoresis (SDS-PAGE).

Leucylation activities of tRNA$^{Leu}$ by the LeuRS Y330A mutant is quantitated by scintillation counting (FIG. 32). Its enzymatic activities are compared to wild-type LeuRS enzymatic activities. In the case of the E. coli LeuRS Y330A mutant, this mutant leucylates tRNA$^{Leu}$ at a higher efficiency to the wild-type protein.

The E. coli Y330/D342A/D345A LeuRS Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using PCR, the single or multiple mutant leuS genes are then generated using PCR primers that contain the desired Y330/D342A/D345A triple mutations.

Figure 47:
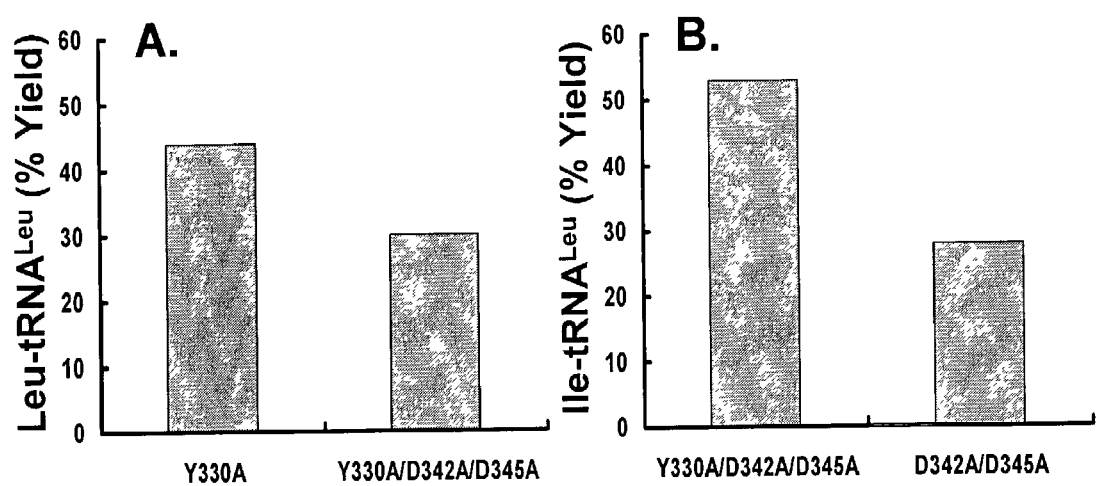
FIG. 47(A) depicts a bar graph demonstrating the efficiency of leucylation by Y330A and Y330A/D342A/D345A mutant LeuRSs.
FIG. 47(B) depicts a bar graph demonstrating the efficiency of isoleucylation by D342A/D345A and Y330A/D342A/D345A mutant LeuRSs

Plasmids harboring the LeuRS with the desired Y330/D342A/D345A mutations are used to transform protein expression strains for recombinant protein production. The LeuRS Y330/D342A/D345A mutants are then purified using immobilized metal affinity chromatography and identified by sodium dodecyl sulfate-polyacrylamide gel electrophoresis (SDS-PAGE). In the case of the *E. coli* LeuRS Y330/D342A/D345A mutant protein, the editing mutant aminoacylates tRNA$^{Leu}$ with isoleucine yielding isoleucine-tRNA$^{Leu}$ in contrast to the wild-type protein that exhibits no isoleucylation activity (FIG. 47B). It also generates significantly higher yields of isoleucine-tRNA$^{Leu}$ compared to the *E. coli* LeuRS D342A/D345A double mutant. Using multiple mutations that decrease or abolish amino acid editing activity will reduce the possibility of restoring the mutant LeuRS editing activity via natural mutagenesis when used in vivo within an organism or cell line.

The *E. coli* LeuRS M40S Mutation

Plasmids harboring the wild-type or mutant leuS gene from a prokaryotic organism are used to create LeuRS fusion proteins that contain N-terminal six-histidine tags (Martinis and Fox, 1997, Mursinna et al., 2001). Using PCR, the single or multiple mutant leuS gene is then generated using PCR primers that contain the desired M40S mutation (Mursinna and Martinis, 2002).

Plasmids harboring the LeuRS M40S mutation are used to transform protein expression strains for recombinant protein production. The LeuRS M40S mutant is then purified using immobilized metal affinity chromatography and identified by sodium dodecyl sulfate-polyacrylamide gel electrophoresis (SDS-PAGE).

Leucine aminoacylation activity for the M40S mutant *E. coli* LeuRS that also contained the editing defect mutations (T252Y/D342A/D345A) was decreased relative to the wild type enzyme (FIG. 29). Amino acid-dependent pyrophosphate exchange activity by the LeuRS M40S mutant is quantitated by TLC separation followed by phosphorimaging (FIGS. 30 and 31). Its enzymatic activities are compared to wild-type LeuRS enzymatic activities. In the case of the *E. coli* LeuRS M40S mutant, norvaline activation is decreased relative to leucine activation.

The *S. cerevisiae* Cytoplasmic LeuRS T319Y Mutation

Plasmids harboring the wild-type CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired T319Y mutation.

Plasmids harboring the LeuRS T319Y mutation are used to transform protein expression strains for recombinant protein production. The LeuRS T319Y mutant is then purified using immobilized metal affinity chromatography and identified by sodium dodecyl sulfate-polyacrylamide gel electrophoresis (SDS-PAGE).

Figure 33:
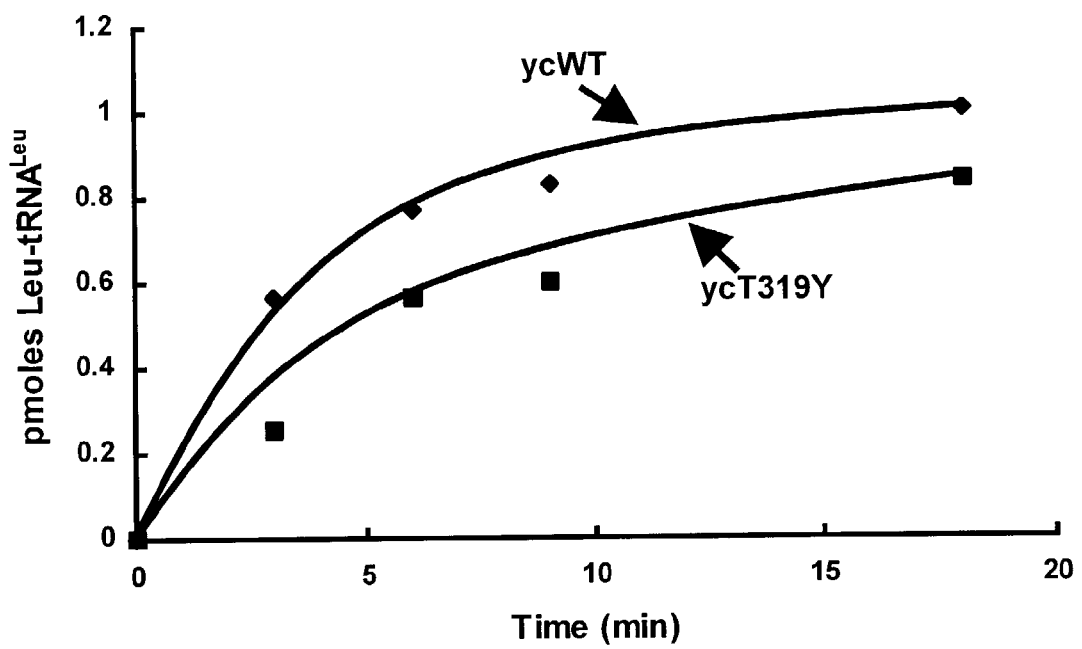
FIG. 33 is a graph of aminoacylation of tRNA$^{Leu}$ with leucine by yeast cytoplasmic wild-type LeuRS and a CP1-based mutant LeuRS, wherein symbols representing aminoacylation by wild-type and mutant are: wild-type (ycWT), closed diamond; ycT319Y, closed square.

Leucylation activities of tRNA$^{Leu}$ by the LeuRS T319Y mutant is quantitated by scintillation counting (FIG. 33). Its enzymatic activities are compared to wild-type LeuRS enzymatic activities. In the case of the *S. cerevisiae* LeuRS T319Y mutant, this editing mutant leucylates tRNA$^{Leu}$ at a similar efficiency to the wild-type protein. Isoleucylation of tRNA$^{Leu}$ by LeuRS T319Y is quantitated by scintillation counting (FIG. 34) and then is compared to results obtained from experiments performed in parallel using the wild-type LeuRS. In the case of the *S. cerevisiae* LeuRS T319Y mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS T319Y/D419A Mutation

Plasmids harboring the wild-type or mutant CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired T319Y and D419A mutations.

Plasmids harboring the LeuRS T319Y/D419A mutations are used to transform protein expression strains for recombinant protein production. The LeuRS T319Y/D419A mutant is then purified using immobilized metal affinity chromatography and identified by sodium dodecyl sulfate-polyacrylamide gel electrophoresis (SDS-PAGE).

Figure 35:
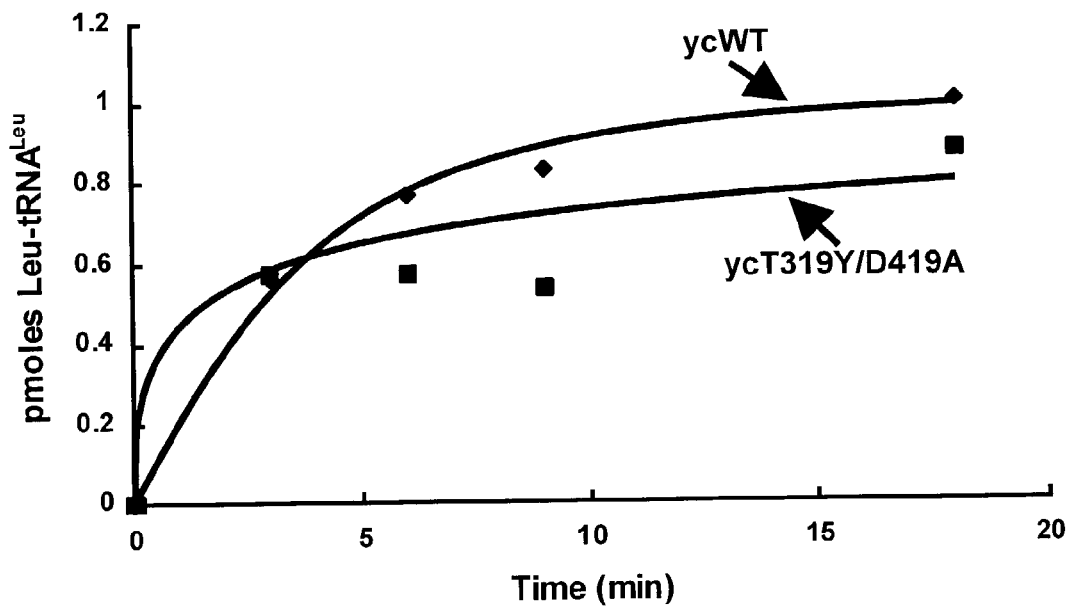
FIG. 35 is a graph of aminoacylation of tRNA$^{Leu}$ with leucine by yeast cytoplasmic wild-type LeuRS and a CP1-based mutant LeuRS, wherein symbols representing aminoacylation activity by wild-type and mutant LeuRS are: wild-type (ycWT), closed diamond; ycT319Y/D419A, closed square.

Leucylation activities of tRNA$^{Leu}$ by the LeuRS T319Y/D419A mutant is quantitated by scintillation counting (FIG. 35). Its enzymatic activities are compared to wild-type LeuRS enzymatic activities. In the case of the *S. cerevisiae* LeuRS T319Y/D419A mutant, this editing mutant leucylates tRNA$^{Leu}$ at a slightly lower efficiency compared to the wild-type protein. Isoleucylation of tRNA$^{Leu}$ by LeuRS T319Y/D419A is quantitated by scintillation counting (FIG. 36) and then is compared to results obtained from experiments performed in parallel using the wild-type LeuRS. In the case of the *S. cerevisiae* LeuRS T319Y/D419A mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS N415A Mutation

Plasmids harboring the wild-type CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired N415A mutation.

Plasmids harboring the LeuRS N415A mutation are used to transform protein expression strains for recombinant protein production. The LeuRS N415A mutant is then purified using immobilized metal affinity chromatography and identified by sodium dodecyl sulfate-polyacrylamide gel electrophoresis (SDS-PAGE).

Figure 37:
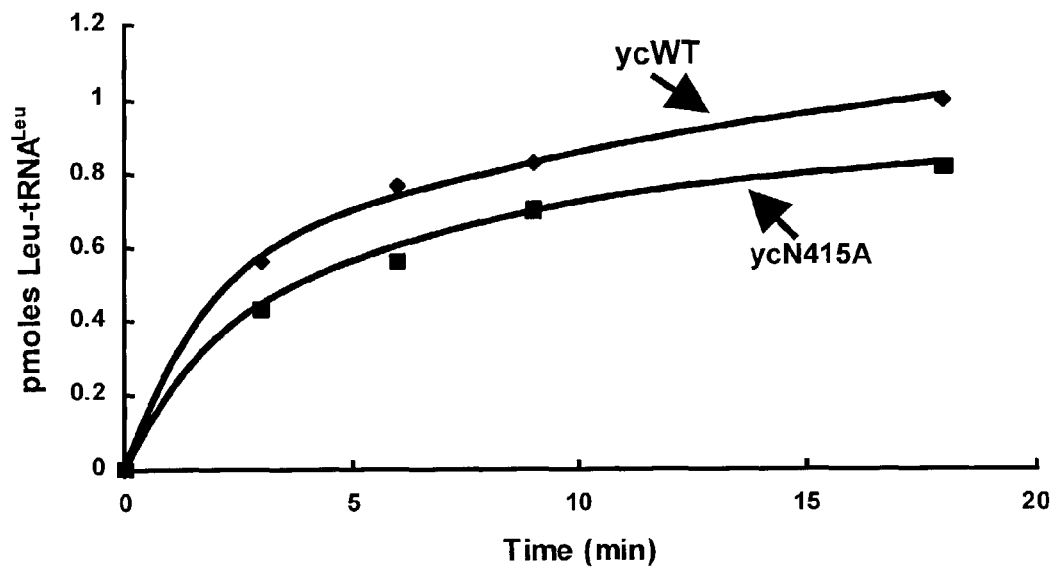
FIG. 37 is graph of aminoacylation of tRNA$^{Leu}$ with leucine by yeast cytoplasmic wild-type LeuRS and a CP1-based mutant LeuRS, wherein symbols representing aminoacylation by wild-type and mutant LeuRS are: wild-type (ycWT), closed diamond; ycN415A, closed square.

Leucylation activities of tRNA$^{Leu}$ by the LeuRS N415A mutant is quantitated by scintillation counting (FIG. 37). Its enzymatic activities are compared to wild-type LeuRS enzymatic activities. In the case of the *S. cerevisiae* LeuRS N415A mutant, this editing mutant leucylates tRNA$^{Leu}$ at a slightly lower efficiency compared to the wild-type protein. Isoleucylation of tRNA$^{Leu}$ by LeuRS N415A is quantitated by scintillation counting (FIG. 38) and then is compared to results obtained from experiments performed in parallel using the wild-type LeuRS. In the case of the *S. cerevisiae* LeuRS N415A mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS N415A/D419A Mutation

Plasmids harboring the wild-type or mutant CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired N415A and D419A mutations.

Plasmids harboring the LeuRS N415A/D419A mutations are used to transform protein expression strains for recombinant protein production. The LeuRS N415A/D419A mutant is then purified using immobilized metal affinity chromatography and identified by sodium dodecyl sulfate polyacrylamide gel electrophoresis (SDS-PAGE).

Figure 39:
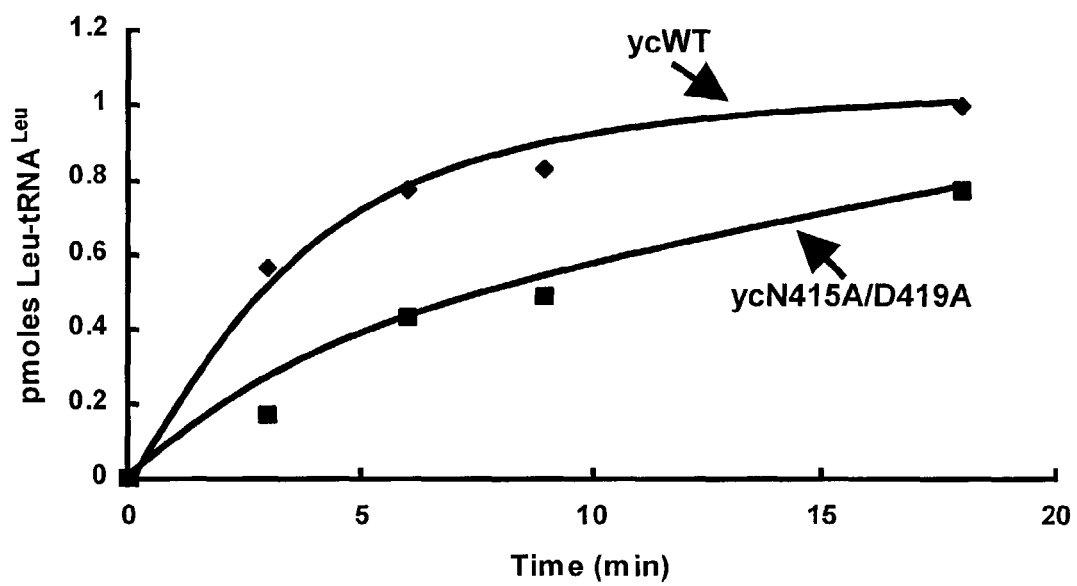
FIG. 39 is a graph of aminoacylation of tRNA$^{Leu}$ with leucine by yeast cytoplasmic wild-type LeuRS and a CP1-based mutant LeuRS, wherein symbols representing aminoacylation activity by wild-type and mutant LeuRS are: wild-type (ycWT), closed diamond; ycN415A/D419A, closed square.

Leucylation activities of tRNA$^{Leu}$ by the LeuRS N415A/D419A mutant is quantitated by scintillation counting (FIG. 39). Its enzymatic activities are compared to wild-type LeuRS enzymatic activities. In the case of the *S. cerevisiae* LeuRS N415A/D419A mutant, this editing mutant leucylates tRNA$^{Leu}$ at a slightly lower efficiency compared to the wild-type protein. Isoleucylation of tRNA$^{Leu}$ by LeuRS N415A/D419A is quantitated by scintillation counting (FIG. 40) and then is compared to results obtained from experiments performed in parallel using the wild-type LeuRS. In the case of the *S. cerevisiae* LeuRS N415A/D419A mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS S416A/D419A Mutation

Plasmids harboring the wild-type or mutant CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired S416A and D419A mutations.

Plasmids harboring the LeuRS S416A/D419A mutations are used to transform protein expression strains for recombinant protein production. The LeuRS S416A/D419A mutant is then purified using immobilized metal affinity chromatography and identified by sodium dodecyl sulfate-polyacrylamide gel electrophoresis (SDS-PAGE).

Figure 41:
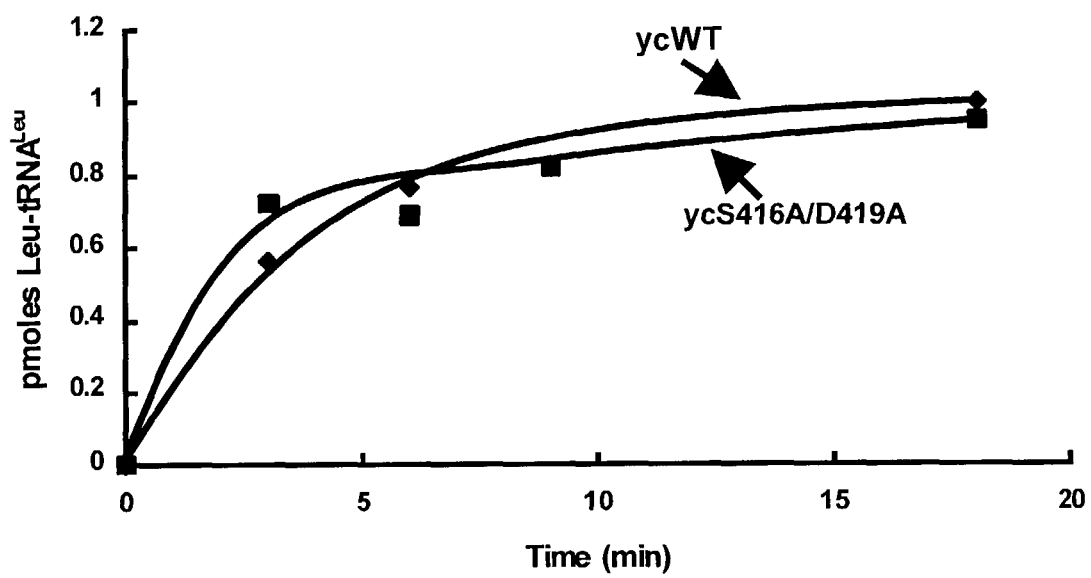
FIG. 41 is a graph of aminoacylation of tRNA$^{Leu}$ with leucine by yeast cytoplasmic wild-type LeuRS and a CP1-based mutant LeuRS, wherein symbols representing aminoacylation activity by wild-type and mutant LeuRS are: wild-type (ycWT), closed diamond; ycS416A/D419A, closed square.

Leucylation activities of tRNA$^{Leu}$ by the LeuRS S416A/D419A mutant is quantitated by scintillation counting (FIG. 41). Its enzymatic activities are compared to wild-type LeuRS enzymatic activities. In the case of the *S. cerevisiae* LeuRS S416A/D419A mutant, this editing mutant leucylates tRNA$^{Leu}$ at a similar efficiency compared to the wild-type protein. Isoleucylation of tRNA$^{Leu}$ by LeuRS S416A/D419A is quantitated by scintillation counting (FIG. 42) and then is compared to results obtained from experiments performed in parallel using the wild-type LeuRS. In the case of the *S. cerevisiae* LeuRS S416A/D419A mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS D418A Mutation

Plasmids harboring the wild-type CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired D418A mutation.

Plasmids harboring the LeuRS D418A mutation are used to transform protein expression strains for recombinant protein production. The LeuRS D418A mutant is then purified using immobilized metal affinity chromatography and identified by sodium dodecyl sulfate-polyacrylamide gel electrophoresis (SDS-PAGE).

Figure 43:
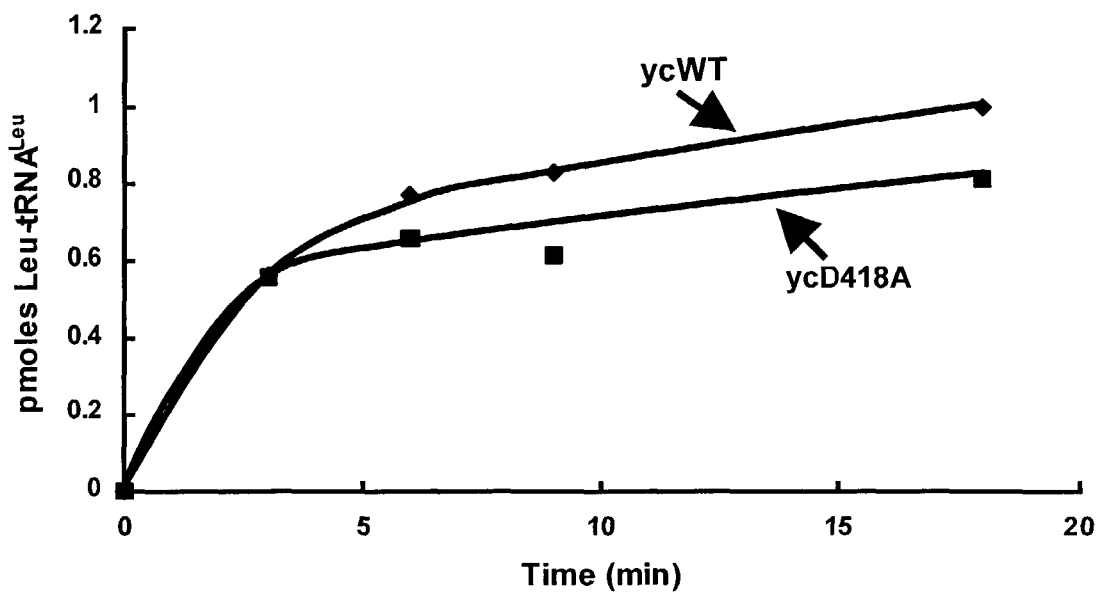
FIG. 43 is a graph of aminoacylation of tRNA$^{Leu}$ with leucine by yeast cytoplasmic wild-type LeuRS and a CP1-based mutant LeuRS, wherein symbols representing aminoacylation activity by wild-type and mutant LeuRS are: wild-type (ycWT), closed diamond; ycD418A, closed square.

Leucylation activities of tRNA$^{Leu}$ by the LeuRS D418A mutant is quantitated by scintillation counting (FIG. 43). Its enzymatic activities are compared to wild-type LeuRS enzymatic activities. In the case of the *S. cerevisiae* LeuRS D418A mutant, this editing mutant leucylates tRNA$^{Leu}$ at a similar efficiency compared to the wild-type protein. Isoleucylation of tRNA$^{Leu}$ by LeuRS D418A is quantitated by scintillation counting (FIG. 44) and then is compared to results obtained from experiments performed in parallel using the wild-type LeuRS. In the case of the *S. cerevisiae* LeuRS D418A mutant protein, the editing mutant aminoacylates tRNA$^{Leu}$ with isoleucine yielding isoleucine-tRNA$^{Leu}$ in contrast to the wild-type protein that exhibits no isoleucylation activity.

The *S. cerevisiae* Cytoplasmic LeuRS D418A/D419A Mutation

Plasmids harboring the wild-type or mutant CDC60 gene from a eukaryotic organism are used to create LeuRS fusion proteins that contain N-terminal six-histidine tags (Lincecum and Martinis, 2000). Using PCR, the mutant CDC60 gene is then generated using PCR primers that contain the desired D418A and D419A mutations.

Figure 45:
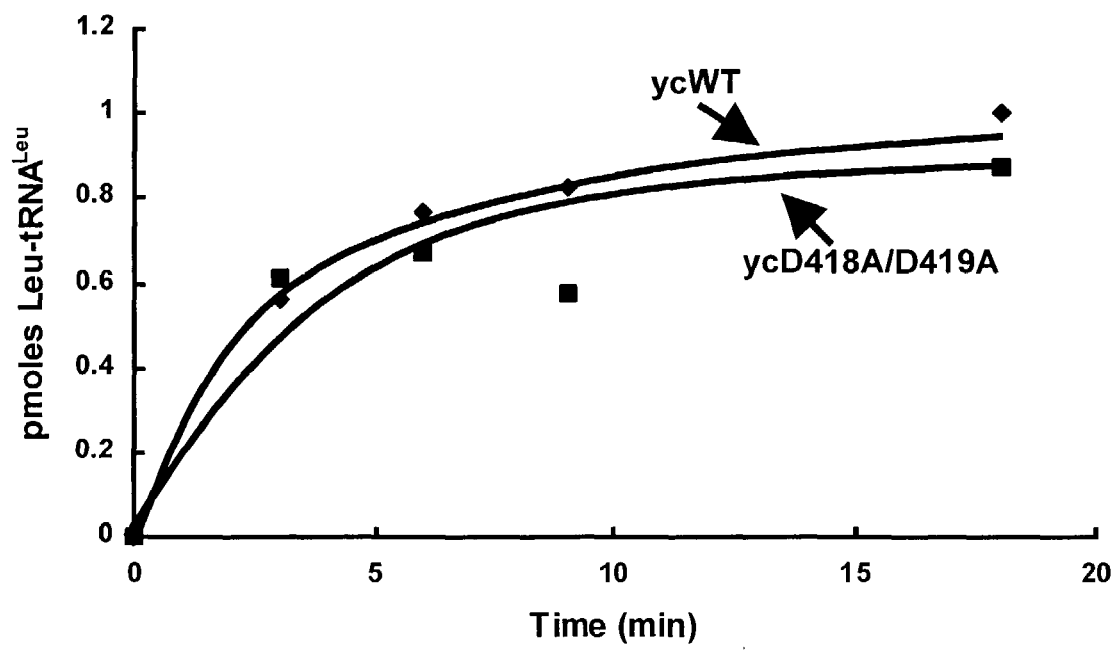
FIG. 45 is a graph of aminoacylation of tRNA$^{Leu}$ with leucine by yeast cytoplasmic wild-type LeuRS and a CP1-based mutant LeuRS, wherein symbols representing aminoacylation activity by wild-type and mutant LeuRS are: wild-type (ycWT), closed diamond; ycD418A/D419A, closed square.

Plasmids harboring the LeuRS D418A/D419A mutations are used to transform protein expression strains for recombinant protein production. The LeuRS D418A/D419A mutant is then purified using immobilized metal affinity chromatography and identified by sodium dodecyl sulfate-polyacrylamide gel electrophoresis (SDS-PAGE). Leucylation activities of tRNA$^{Leu}$ by the LeuRS D418A/D419A mutant is quantitated by scintillation counting (FIG. 45). Its enzymatic activities are compared to wild-type LeuRS enzymatic activities. In the case of the *S. cerevisiae* LeuRS D418A/D419A mutant, this editing mutant leucylates tRNA$^{Leu}$ at a similar efficiency compared to the wild-type protein. Isoleucylation of tRNA$^{Leu}$ by LeuRS D418A/D419A is quantitated by scintillation counting (FIG. 46) and then is compared to results obtained from experiments performed in parallel using the wild-type LeuRS. In the case of the *S. cerevisiae* LeuRS D418A/D419A mutant protein, the editing mutant aminoacylates tRNA$^{Leu}$ with isoleucine yielding isoleucine-tRNA$^{Leu}$ in contrast to the wild-type protein that exhibits no isoleucylation activity.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

EXAMPLES

The following examples illustrate various embodiments of the present invention.

Example 1

Homology Models of Leucyl-tRNA Synthetases

Based on the X-ray crystal structure of *Thermus thermophilus* LeuRS (Cusack et al., 2000) and its coordinates, minimized homology models for *E. coli* (Lee and Briggs, 2002) and yeast LeuRSs have already been developed to aid designing mutants to inactivate the amino acid editing mechanism and also subsequent rational design of the LeuRS editing and aminoacylation active sites. Compared to other closely related editing tRNA synthetases such as IleRS and ValRS, the amino acid binding pocket for leucine in the aminoacylation active site would have a larger volume and thus would be expected to accommodate a greater diversity of noncognate amino acids. Target remodeling of the leucine binding pocket via iterative computational and mutagenesis experiments is planned and in progress to adapt the active site for productive binding to specific noncognate amino acids that facilitate efficient and stable aminoacylation to tRNA molecules.

Example 2

T252A: Prokaryotic LeuRS Mutation

In one embodiment, leucyl-tRNA synthetase mutants described herein are made for prokaryotic organisms including, but not limited to *E. coli* LeuRS T252A.

In the present example the *E. coli* LeuRS T252A mutation was introduced via the polymerase chain reaction (PCR) into the plasmid p15EC3-1 harboring the wild-type *E. coli* leuS gene to create plasmid pMURe10. Expression of this gene from either plasmid yields an *E. coli* LeuRS fusion protein that contains an N-terminal six-histidine tag. The mutant leuS gene was amplified using 100 ng p15EC3-1 and 225 pmoles each of a forward and reverse primer [5'-CTACCCGCCCG-GACGCCTTTATGGGTTGTACC-3' (SEQ ID NO.:1) and 5'-GATGGGCGGGCCTGCGGAAATACCCAACATGG-3' (SEQ ID NO.:2), respectively] that encoded the gene mutation. The PCR reaction mixture also contained 10 pmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 16 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pMURe10) was isolated using Wizard miniprep kits (Promega; Madison, Wis.). Sequencing of pMURe10 was performed by Lone Star Labs (Houston, Tex.) using a primer (5'-CCGAAGGCGTGGAGATC-3') (SEQ ID NO.:3) that annealed upstream of the mutated DNA region.

Plasmid pMURe10 harboring *E. coli* LeuRS T252A was used to transform *E. coli* strain BL21(DE3)pLysS (Invitrogen Corporation; Carlsbad, Calif.). A 500 ml LB culture that included 100 µg/ml ampicillin was grown at 37° C. to an $A_{600}$ of near 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the *E. coli* LeuRS T252A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The *E. coli* LeuRS T252A mutant containing a six-histidine tag was eluted with 20 mM $Na_2HPO_4$ (pH 8.0), 10 mM Tris (pH 8.0), 100 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 100 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of $tRNA^{Leu}$ by the *E. coli* LeuRS T252A mutant was measured in a reaction containing 60 mM Tris, pH 7.5, 10 mM $MgCl_2$, 1 mM dithiothreitol (DTT), 4 mM ATP, 4 µM $tRNA^{Leu}$, 25.4 µM [$^3H$]-leucine (150 µCi/ml) and 15 nM enzyme. The reaction was initiated by the addition of ATP. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 60001C (Beckman Instruments, Inc.; Fullerton, Calif.). Results were compared with those obtained from experiments performed in parallel using the wild-type *E. coli* LeuRS. The T252A LeuRS did not leucylate appriciatable amounts of $tRNA^{Leu}$ (FIG. 3).

Activation of leucine by the *E. coli* T252A mutant was measured in a pyrophosphate exchange assay. The reaction contained 50 mM N-2-Hydroxyethylpiperazine-N'-2-ethane-sulfonic acid (HEPES), pH 8.0, 1 mM ATP, 10 mM $MgCl_2$, 1 mM DTT, and 1 mM [$^{32}P$]-pyrophosphate (53.3 µCi/ml), 50 nM enzyme, and 250 µM leucine. The reaction was initiated with the addition of leucine. TLC cellulose PEI plates (Scientific Adsorbents Inc.) were pre-run in water for 2 hours. 2 µL aliquots of the reaction were removed at 0, 3, 6, 9, and 12 minutes and placed on the pre-run TLC plates to quench the reaction. The TLC plates were placed in a 75 mM $KH_2PO_4$, pH 3.5, 4 M urea running buffer, and allowed to run for 3 hours. The TLC plates were dried, wrapped in saran wrap, and placed onto a phosphoimager screen in a Fujifilm BAS 2040 cassette. The phosphorimager screen was imaged in the Fujix BAS-1000 phosphorimager and the amount of radiolabel present in the spots on the plates quantified using the quantitation mode of the ImageGuage V3.0 software program. The E. coli LeuRS T252A mutant activates leucine at a slightly lower efficiency than the wild-type LeuRS protein (FIGS. 4A and B).

The hydrolytic editing activity of E. coli LeuRS T252A was measured using a reaction mixture consisting of 60 mM Tris, pH 7.0, 10 mM $MgCl_2$, and aminoacylated [$^3$H]-leucine-tRNA$^{Leu}$ (50 µCi/ml). The reaction was initiated by the addition of 100 nM enzyme. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The pads were dried and added to 3 ml of ScintiSafe Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using both the wild-type E. coli LeuRS. FIG. 5 demonstrates that LeuRS T252A edits the cognate charged Leu-tRNA$^{Leu}$.

Example 3

T252F—Prokaryotic LeuRS Mutation

In another embodiment, leucyl-tRNA synthetase mutants described herein are made for prokaryotic organisms including, but not limited to E. coli LeuRS T252F.

In the present example the E. coli LeuRS T252F mutation was introduced via the polymerase chain reaction (PCR) into the plasmid p15EC3-1 harboring the wild-type E. coli leuS gene to create plasmid pMURe2 1. Expression of this gene from either plasmid yields an E. coli LeuRS fusion protein that contains an N-terminal six-histidine tag. The mutant leuS gene was amplified using 100 ng p15EC3-1 and 225 pmoles each of a forward and reverse primer [5'-CCC GCC CGG ACT TCT TTA TGG GTT GTA CC-3' (SEQ ID NO. 4) and 5'-GGT ACA ACC CAT AAA GAA GTC CGG GCG GG-3' (SEQ ID NO. 5), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 16 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA for pMURe21 was isolated using Wizard miniprep kits (Promega; Madison, Wis.). Sequencing of pMURe21 was performed by Lone Star Labs (Houston, Tex.) using a primer (5'-CCGAAGGCGTGGAGATC-3')(SEQ ID NO.:6) that annealed upstream of the mutated DNA region.

Plasmid pMURe21 harboring E. coli LeuRS T252F was used to transform E. coli strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS T252F mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS T252F mutant containing a six-histidine tag was eluted with 20 mM $Na_2HPO_4$ (pH 8.0), 10 mM Tris (pH 8.0), 100 mM NaCl, 100 mM imidazole and 10% glycerol. The elution fraction was concentrated and dialyzed into its final storage buffer of 20 mM $Na_2HPO_4$ (pH 8.0), 10 mM Tris (pH 7.0), 100 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of tRNA$^{Leu}$ by the E. coli LeuRS T252F mutant was measured in a reaction containing 60 mM Tris, pH 7.5, 10 mM $MgCl_2$, 1 mM dithiothreitol (DTT), 4 mM ATP, 4 µM tRNA$^{Leu}$, 25.4 µM [$^3$H]-leucine (150 µCi/ml) and 15 nM enzyme. The reaction was initiated by the addition of ATP. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS T252F mutant leucylates tRNA$^{Leu}$ at a similar efficiency as the wild-type protein (FIG. 9).

Isoleucylation of tRNA$^{Leu}$ by E. coli LeuRS T252F was measured in a reaction containing 60 mM Tris, pH 7.5, 10 mM $MgCl_2$, 1 mM dithiothreitol (DTT), 4 mM ATP, 7 µM in vitro transcribed tRNA$^{Leu}$, 22 µM [$^3$H]-isoleucine (180 µCi/ml) and 1 µM enzyme. The reaction was initiated by the addition of ATP and quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS T252F protein aminoacylated tRNA$^{Leu}$ with isoleucine yielding isoleucine-tRNA$^{Leu}$ in contrast to the wild-type protein (FIG. 10).

A 15.4 µl aliquot of 100 µM concentration (or 1540 pmoles) of tRNA$^{Leu}$ was aminoacylated with [$^3$H]-isoleucine in an isoleucylation reaction as described above using E. coli LeuRS T252F for 30 min at 37° C. The pH of the reaction was adjusted to 5.0 using acetic acid (0.1% v/v) and the aminoacylated isoleucyl-tRNA$^{Leu}$ was immediately extracted using phenol/chloroform/isoamyl alcohol (25:24:1) (pH 5.1) (Fisher Scientific; Fair Lawn, N.J.). The aminoacylated isoleucyl-tRNA$^{Leu}$ was concentrated by ethanol precipitation, and resuspended in 50 mM KH$_2$PO$_4$ (pH 5.0) at a concentration of 50 µM. The aminoacylated isoleucyl-tRNA$^{Leu}$ was stored at −20° C.

The hydrolytic editing activity of *E. coli* LeuRS T252F was measured using a reaction mixture consisting of 60 mM Tris, pH 7.0, 10 mM MgCl$_2$, and aminoacylated [$^3$H]-isoleucyl-tRNA$^{Leu}$ (50 µCi/ml). The reaction was initiated by the addition of 100 nM enzyme. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The pads were dried and added to 3 ml of ScintiSafe Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those experiments performed in parallel using both the wild-type *E. coli* LeuRS and the *E. coli* LeuRS T252A mutant. Both the wild-type and T252A LeuRSs deacylated the mischarged tRNA. However, *E. coli* LeuRS T252F did not hydrolyze the misacylated tRNA (FIG. 11).

Example 4

T252Y—Prokaryotic LeuRS Mutation

In yet another embodiment, leucyl-tRNA synthetase mutants described herein are made for prokaryotic organisms including, but not limited to *E. coli* LeuRS T252Y.

In the present example the *E. coli* LeuRS T252Y mutation was introduced via the polymerase chain reaction (PCR) into the plasmid p 15EC3-1 harboring the wild-type *E. coli* leuS gene to create plasmid pMURe22. Expression of this gene from either plasmid yields an *E. coli* LeuRS fusion protein that contains an N-terminal six-histidine tag. The mutant leuS gene was amplified using 100 ng p15EC3-1 and 225 pmoles each of a forward and reverse primer [5'-CCC GCC CGG ACT ACT TTA TGG GTT GTA CC-3' (SEQ ID NO.:7) and 5'-GGT ACA ACC CAT AAA GTA GTC CGG GCG GG-3' (SEQ ID NO.:8), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM (NH4)$_2$SO$_4$, 2 mM MgSO$_4$, 0.1% Triton X-100 and 100 µg/ml bovine serum albumen (BSA). The PCR reaction was thermocycled 16 times. Each cycle was as follows: denaturation (95° C., 1 min), annealing (60° C., 30 sec) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA for pMURe22 was isolated using Wizard miniprep kits (Promega; Madison, Wis.). Sequencing of pMURe22 was performed by Lone Star Labs (Houston, Tex.) using a primer (5'-CCGAAGGCGTGGAGATC-3')(SEQ ID NO.:6) that annealed upstream of the mutated DNA region.

The plasmid pMURe22 harboring *E. coli* LeuRS T252Y was used to transform *E. coli* strain BL21 pLysS (Invitrogen Corporation; Carlsbad, Calif.). A 500 ml LB culture that included 100 µg/ml ampicillin was grown at 37° C. to an A$_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM Na$_2$HPO$_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the *E. coli* LeuRS T252Y mutant was mixed gently at 4° C. for 30 minutes. The resin was separated from the supernatant in a clinical centrifuge (International Equipment Co.; Needham Heights, Mass.). The resin was washed four times with 10 ml of 20 mM Na$_2$HPO$_4$ (pH 7.0), 10 mM Tris, 500 mM NaCl and 10% glycerol. The *E. coli* LeuRS T252Y mutant containing a six-histidine tag was eluted with 20 mM Na$_2$HPO$_4$ (pH 8.0), 10 mM Tris (pH 8.0), 100 mM NaCl, 100 mM imidazole and 10% glycerol. The elution was concentrated and dialyzed into its final storage buffer of 20 mM Na$_2$HPO$_4$ (pH 8.0), 10 mM Tris (pH 7.0), 100 mM NaCl, <10 mM imidazole and 50% glycerol. The purified 98.5 kDa LeuRS fusion protein was identified by sodium dodecyl sulfate polyacrylamide gel electrophoresis (SDS-PAGE).

Leucylation of tRNA$^{Leu}$ by the *E. coli* LeuRS T252Y mutant was measured in a reaction containing 60 mM Tris, pH 7.5, 10 mM MgCl$_2$, 1 mM dithiothreitol (DTT), 4 mM ATP, 4 µM tRNA$^{Leu}$, 25.4 µM [$^3$H]-leucine (150 µCi/ml) and 15 nM enzyme. The reaction was initiated by the addition of ATP. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The *E. coli* LeuRS T252Y mutant leucylates tRNA$^{Leu}$ at a similar efficiency as the wild-type protein (FIG. 9).

Isoleucylation of tRNA$^{Leu}$ by *E. coli* LeuRS T252Y was measured in a reaction containing 60 mM Tris pH 7.5, 10 mM MgCl$_2$, 1 mM dithiothreitol (DTT), 4 mM ATP, 7 µM in vitro transcribed tRNA$^{Leu}$, 22 µM [$^3$H]-isoleucine (180 µCi/ml) and 1 µM enzyme. The reaction was initiated by the addition of ATP and quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The *E. coli* LeuRS T252Y protein aminoacylated tRNA$^{Leu}$ with isoleucine yielding isoleucine-tRNA$^{Leu}$ in contrast to the wild-type protein (FIG. 10).

A 15.4 µl aliquot of 100 µM concentration (or 1540 pmoles) of tRNA$^{Leu}$ was aminoacylated with [$^3$H]-isoleucine in an isoleucylation reaction as described above using *E. coli* LeuRS T252Y for 30 min at 37° C. The pH of the reaction was adjusted to 5.0 using acetic acid (0.1% v/v) and the aminoacylated isoleucyl-tRNA$^{Leu}$ immediately extracted using phenol/chloroform/isoamyl alcohol (25:24:1) (pH 5.1) (Fisher Scientific; Fair Lawn, N.J.). The aminoacylated isoleucyl-tRNA$^{Leu}$ was concentrated by ethanol precipitation, and resuspended in 50 mM KH$_2$PO$_4$ (pH 5.0) at a concentration of 50 µM. The aminoacylated isoleucyl-tRNA$^{Leu}$ was stored at −20° C.

The hydrolytic editing activity of *E. coli* LeuRS T252Y was measured using a reaction mixture consisting of 60 mM Tris, pH 7.0, 10 mM MgCl$_2$, and aminoacylated [$^3$H]-isoleucyl-tRNA$^{Leu}$ (50 µCi/ml). The reaction was initiated by the addition of 100 nM enzyme. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were the washed with 70% ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those from experiments performed in parallel using both the wild-type *E. coli* LeuRS and the *E. coli* LeuRS T252A mutant. Both the wild-type and T252A LeuRSs deacylated the mischarged tRNA. However, *E. coli* LeuRS T252Y did not hydrolyze the misacylated tRNA (FIG. 11).

Example 5

D419A—Eukaryotic LeuRS Mutation

In still another embodiment, leucyl-tRNA synthetase mutants described herein are made for eukaryotic organisms including, but not limited to *S. cerevisiae* LeuRS D419A.

In the present example primary sequence alignments using ClustalW 1.8 sequence alignment analysis identified an aspartic acid residue in the CP1 editing domain that was completely conserved across LeuRS, IleRS, and ValRS (FIG. 12). This aspartic acid (Asp 419) in yeast cytoplasmic LeuRS was changed to an alanine residue (D419A) by site-directed mutagenesis of the gene encoding yeast cytoplasmic LeuRS. Specifically, the mutant LeuRS gene was amplified via PCR using the template plasmid p32YL-2-3 annealed to oligonucleotides that contain a mismatch at position 1408 in the nucleotide sequence to convert an adenosine to a cysteine. The plasmid template was isolated using the Wizard Miniprep Kit (Promega; Madison, Wis.). The two oligonucleotides were synthesized by Sigma (Woodlands, Tex.) and include a reverse primer (5' GGT TTG TGC AAC AAG TCC TTG GTG GTA ATG TA<u>GGC</u>A TCT GGT GAA TTA GAT GGT ACA CAC GTG 3') (SEQ ID NO.:9) and a forward primer (5' CAC GTG TGT ACC ATC TAA TTC ACC AGA T<u>GCC</u>TA CCA TAC ATC CAA GGA CTT GTT GCA CAA ACC 3') (SEQ ID NO.:10). Each was designed to anneal to the region containing the nucleotides that code for Asp 419. (The underlined nucleotides represent the site of the codon mutation to change Asp 419 to an alanine in the expressed protein.) The final reaction contained 125 ng of each of the forward and reverse primers, 0.1 µg p32YL-2-3, 1X Pfu DNA polymerase buffer (Promega; Madison, Wis.), 200 µM dNTPs (Promega; Madison, Wis.), and 0.06 U/µl Pfu DNA polymerase (Promega; Madison, Wis.). The reaction was carried out by first mixing and heating all of the components, excluding the Pfu DNA polymerase and dNTPs, at 95° C. for 5 minutes. The Pfu DNA polymerase and dNTPs were then added and the reaction was thermocycled 1 time at: denaturation (95° C., 30 sec), annealing (58° C., 30 sec) and extension (68° C., 30 s followed by 16 times at: denaturation (95° C., 30 sec), annealing (58° C., 30 sec) and extension (68° C., 20 min). The PCR products were stored at 4° C. until removal from thermocycler.

The amplified PCR product yielding the mutant yeast cytoplasmic LeuRS gene called p32-AMW1 was analyzed on a 1% agarose gel. The PCR reaction containing plasmid p32-AMW1 was used to transform competent *E. coli* DH5α cells (Invitrogen Corporation; Carlsbad, Calif.) by the heat shock method. Transformed cells were incubated at 37° C. overnight on Luria Broth (LB) agarose plates that contained 100 µg/µl ampicillin. The p32-AMW1 plasmid was then isolated using the Wizard Miniprep Kit (Promega; Madison, Wis.) and the gene insert was sequenced by Lone Star Labs (Houston, Tex.) to verify the correct mutation had been made. Once verified, competent *E. coli* BL21-CodonPlus cells (Stratagene; La Jolla, Calif.) were transformed with the p32-AMW1 plasmid by the heat shock method.

Two 3 ml cultures of LB containing 100 µg/ml ampicillin and 34 µg/ml chloramphenicol were inoculated either with *E. coli* BL21 (-Codon Plus) cells that contain p32YL-2-3 encoding the wild-type yeast cytoplasmic LeuRS and the other with *E. coli* BL21(-Codon Plus) cells which contained p32-AMW1 that encoded the D419A mutant yeast cytoplasmic LeuRS. Both genes were fused to a 5' upstream region that encodes a six-histidine tag. The cultures were then incubated overnight at 37° C. with shaking and used to inoculate two separate 500 ml cultures that contained 100 µg/ml ampicillin and 34 µg/ml chloramphenicol. The 500 ml cultures were incubated at 37° C. with shaking for approximately 3.5 hours. When the optical density (O.D.$_{.600}$) was between 0.6 and 0.9, protein expression was induced in both cultures by the addition of 1 mM IPTG. The cultures were incubated for another 30 minutes at 37° C. with shaking and harvested by centrifugation in a Beckman J2-HS Centrifuge at 10,000×g for 15 minutes. The harvested pellets were stored at −80° C. until purification.

The pellet containing either the wild-type or mutant D419A yeast cytoplasmic LeuRS fused to an N-terminal six histidine tag was resuspended in 2 ml of cold buffer A (20 mM Tris pH 7.4, 100 mM NaCl, 5% glycerol) at 4° C. Phenylmethyl sulfonyl fluoride (PMSF) was then added to the resuspended pellet to a final concentration of 0.1 mM. The cells were lysed by sonication (Vibracell Sonics and Materials) at 50% duty for two periods of 90 seconds each. The cell lysate was cleared by centrifugation at 13,800×g for 15 minutes at 4° C. The supernatant was applied to 2 ml of Talon metal affinity resin that had been pre-equilibrated with buffer A. The resin was incubated with the lysate via gentle shaking at 4° C. for 30 minutes to allow binding of the wild-type or mutant D419A yeast cytoplasmic LeuRS with the fused N-terminal affinity six histidine tag. The resin was then centrifuged at very low speed in a clinical centrifuge (International Equipment Company) to pellet the resin. The supernatant was removed and stored at 4° C. The resin was then washed 3 times with 10 ml of cold buffer A. These washes were quick washes in that the resin was resuspended and then centrifuged immediately in a clinical centrifuge. The resin was then washed three more times with 10 ml of cold buffer A. These washes included a 10 minute incubation period with gentle shaking at 4° C. The wash supernatants were removed by centrifugation. The wild-type and mutant yeast cytoplasmic LeuRS was eluted using six 500 µl aliquots of 100 mM imidazole in buffer A. The resin was resuspended and then incubated at 4° C. for 8-10 minutes. The elution fractions were then collected and stored at 4° C.

All fractions from the affinity batch purification of LeuRS were analyzed by sodium dodecyl sulfate polyacrylamide gel electrophoresis (SDS-PAGE). Elution fractions that contained a band at about 150 kDa molecular weight were combined and concentrated in a YM-50 centricon (Amicon; Bedford, Mass.). The centricons were also used to remove excess imidazole by replacing the original elution buffer with buffer A. The concentrated protein was stored in 50% glycerol at −20° C.

Leucylation of tRNA$^{Leu}$ was carried out at a constant temperature of 35° C. using an MJ Research Peltier Thermal Cyler-200 DNA Engine with 26 nm enzyme. The reaction mixture contained 60 mM Tris, pH 7.5, 10 mM MgCl$_2$, 1 mM DTT, 10 µM leucine, 100 µCi/ml of [$^3$H]-leucine (Amersham Life Science; Piscataway, N.J.), and 5 mg/ml crude yeast tRNA (Sigma; St. Louis, Mo.). The reaction mixture was pre-incubated for 5 minutes with enzyme and initiated by the addition of 4 mM ATP (Amersham Life Science; Piscataway, N.J.). At specific time points, 5 µl of the reaction were removed and transferred to Whatman filter pads that were pre-wetted with 5% TCA. About 10 seconds after transferring the aliquot to the pad, the filter pad was then placed in 5% TCA (chilled on ice). At the end of the reaction time course, the pads in 5% TCA (chilled on ice) were placed on a shaker at 65 rpm. The pads were allowed to wash for 10 minutes and then recovered for subsequent washes in 5% TCA. The pads were washed three times in cold 5% TCA followed by one wash in 70% ethanol, and once in anhydrous ether. The pads were dried for 1 hour and then placed in a 20 ml glass scintillation vial with 3 ml of ScintSafe Econo 1 Cocktail (Fisher Scientific; Pittsburgh, Pa.). The radioactivity was measured using an LS 6000SC scintillation counter. Results showed that wild-type LeuRS and the D419A mutant LeuRS aminoacylated tRNA$^{Leu}$ with leucine at similar rates (FIG. 13).

Isoleucylation of tRNA$^{Leu}$ was carried out at a constant temperature of 35° C. using an MJ Research Peltier Thermal Cyler-200 DNA Engine with 300 nM wild-type or D419A mutant yeast cytoplasmic yeast LeuRS. The reaction mixture included 60 mM Tris, pH 7.5, 10 mM MgCl$_2$, 1 mM DTT, 20 µM [$^3$H]-isoleucine (250 µCi/ml; Amersham Life Science; Piscataway, N.J.), and 5 mg/ml crude yeast tRNA (Sigma; St. Louis, Mo.). The reaction and washes were carried out as described above. Results showed that the D419A LeuRS mutant could carry out isoleucylation of tRNA$^{Leu}$ whereas the wild-type enzyme did not at detectable levels (FIG. 14).

Misaminoacylated isoleucyl-tRNA$^{Leu}$ was produced enzymatically using the yeast cytoplasmic D419A LeuRS mutant. The reaction conditions were carried out as described above in a 240 µl reaction. The reaction was allowed to proceed for 120 minutes and then stopped by quenching with the addition of acetic acid to a final concentration of 0.15%. The protein was removed by extraction with two equal volumes of phenol: chloroform: isoamyl alcohol (pH 5.2). The aqueous phase was removed and ½ volume of 4.6 M NH$_3$OAc (pH 5.0) was added followed by 0.23 mg/ml glycogen (Sigma; St. Louis, Mo.). The reaction was mixed and 2.5 volumes of 100% cold ethanol were added and incubated at −80° C. for 1 hour. The precipiated isoleucyl-tRNA$^{Leu}$ was recovered by centrifugation at 20,000 g for 30 minutes. The RNA-containing pellet was then washed twice with cold 70% ethanol and dried in a speed vac. Mischarged tRNA was stored at −20° C. Pelleted misaminoacyalated [$^3$H]-isoleucyl-tRNA$^{Leu}$ was resuspended in 50 mM KPi (pH 5.0) yielding approximately a 40 mg/ml stock of total RNA.

A hydrolytic editing reaction mixture included 60 mM Tris, pH 7.5, 10 mM MgCl$_2$, 7.2 mg/ml [$^3$H]-isoleucine-tRNA$^{Leu}$ and either 100 nM wild-type or D419A mutant yeast cytoplasmic LeuRS. The reaction was carried out at room temperature. At specific time points, a 5 µl aliquot of the reaction mixture was spotted on a filter pad pre-wetted with 5% TCA and washed as described above. The results showed that the D419A mutant LeuRS did not hydrolyze isoleucyl-tRNA$^{Leu}$ and that the wild-type LeuRS edited the mischarged tRNA (FIG. 17).

Misaminoacylated tRNA$^{Leu}$ was analyzed by electrophoresis on a denaturing gel under acidic conditions. Reactions were carried out as described above for leucylation and isoleucylation of tRNA$^{Leu}$ with the exception of using [$^{14}$C]-leucine (0.3 Ci/mole) and [$^{14}$C]-isoleucine (0.3 Ci/mole) at a concentration of 40 µM each. Methionylation of tRNA$^{Leu}$ was carried out at 35° C. using an MJ Research Peltier Thermal Cyler-200 DNA Engine with 300 nM enzyme. The reaction mixture included 60 mM Tris, pH 7.5, 10 mM MgCl$_2$, 1 mM DTT, 20 µM [$^{35}$S]-methionine (303 µCi/ml; Amersham Life Sciences; Piscataway, N.J.), and 5 mg/ml crude yeast tRNA (Sigma; St. Louis, Mo.). A 5 µl aliquot of each reaction was stopped at specific time points in 5 µl of quench buffer [100 mM NaOAc (pH 5.0), 8 M Urea, 0.05 M EDTA, 0.05% bromophenol blue, and 0.05% xylene cyanol] on ice. The sample was analyzed via acid gel electrophoresis by loading 5 µl of the quenched reaction onto a 6.5% acrylamide:bis-acrylamide solution [19:1] (Biorad, Hercules, Calif.), 8 M Urea, 25 mM NaOAc (pH 5.0), 0.08% ammonium persulfate, 0.05% N,N,N',N'-tetramethylethylenediamine (Promega, Madison, Wis.). The gel was electrophoresed at 500 V until dye front reached the end of gel. The gel was dried using a Model 583 Gel Dryer (BioRad, Hercules, Calif.) and imaged using a FUJIX BAS 1000 phosphorimager (Fuji, Stamford, Conn.). Results showed detectable bands of leucine-tRNA$^{Leu}$ for wt LeuRS (FIG. 15). No detectable bands were seen for mischarging isoleucine to tRNA$^{Leu}$ by the wild-type LeuRS (FIG. 15). In contrast to the wild-type enzyme, the D419A LeuRS mutant yielded detectable bands for leucyl-, isoleucyl-, and methionyl-tRNA$^{Leu}$ (FIGS. 15 and 16)

Example 6

D342A—Prokaryotic LeuRS Mutation

In yet another embodiment, leucyl-tRNA synthetase mutants described herein are made for prokaryotic organisms including, but not limited to E. coli LeuRS D342A.

In the present example the E. coli LeuRS D342A mutation was introduced via the polymerase chain reaction (PCR) into the plasmid p15ec3-1 harboring the wild-type E. coli leuS gene to create plasmid pMURe15. Expression of this gene from either plasmid yields an E. coli LeuRS fusion protein that contains an N-terminal six-histidine tag. The mutant leuS gene was amplified using 100 ng p15ec3-1 and 225 pmoles each of a forward and reverse primer [5' GGT ACC GGG GCA CGC CCA GCG CGA CTA CG 3' (SEQ ID NO.: 11) and 5' CCA TGG CCC CGT GCG GGT CGC GCT GAT GC 3' (SEQ ID NO.:12), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA (pMURe15) was isolated using Wizard miniprep kits (Promega; Madison, Wis.). Sequencing of pMURe15 was performed by Lone Star Labs (Houston, Tex.) using a primer (5'-CCGAAGGCGTGGAGATC-3') (SEQ ID NO.:6) that annealed upstream of the mutated DNA region.

Plasmid pMURe15 harboring E. coli LeuRS D342A was used to transform E. coli strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS D342A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS D342A mutant containing a six-histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of $tRNA^{Leu}$ by the E. coli LeuRS D342A mutant was measured in a reaction containing 60 mM Tris, pH 7.5, 10 mM $MgCl_2$, 1 mM dithiothreitol (DTT), 4 mM ATP, 4 mg/ml crude E. coli tRNA, 21.5 µM [$^3$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS D342A mutant leucylates $tRNA^{Leu}$ at a similar efficiency as the wild-type protein (FIG. 24).

Isoleucylation of $tRNA^{Leu}$ by E. coli LeuRS D342A was measured in a reaction containing 60 mM Tris pH 7.5, 10 mM $MgCl_2$, 1 mM dithiothreitol (DTT), 4 mM ATP, 4 mg/ml crude $tRNA^{Leu}$, 22 µM [$^3$H]-isoleucine (180 µCi/ml) and 1 µM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS D342A protein aminoacylated very low yields of $tRNA^{Leu}$ with isoleucine in contrast to the wild-type protein (FIG. 25).

Valylation of $tRNA^{Leu}$ by E. coli LeuRS D342A was measured in a reaction containing 60 mM Tris pH 7.5, 10 mM $MgCl_2$, 1 mM dithiothreitol (DTT), 4 mM ATP, 4 mg/ml crude $tRNA^{Leu}$, 22 µM [$^3$H]-valine (200 µCi/ml) and 1 µM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS D342A protein aminoacylated low yields of $tRNA^{Leu}$ with valine in contrast to the wild-type protein (FIG. 26).

A 15.4 µl aliquot of 100 µM concentration (or 1540 pmoles) of $tRNA^{Leu}$ was aminoacylated with [$^3$H]-isoleucine in an isoleucylation reaction as described above using E. coli LeuRS D342A/D345A for 30 min at 37° C. The pH of the reaction was adjusted to 5.0 using acetic acid (0.1% v/v) and the aminoacylated isoleucyl-$tRNA^{Leu}$ immediately extracted using phenol/chloroform/isoamyl alcohol (25:24:1) (pH 5.1) (Fisher Scientific; Fair Lawn, N.J.). The aminoacylated isoleucyl-$tRNA^{Leu}$ was concentrated by ethanol precipitation, and resuspended in 50 mM $KH_2PO_4$ (pH 5.0) at a concentration of 50 µM. The aminoacylated isoleucyl-$tRNA^{Leu}$ was stored at −20° C.

The hydrolytic editing activity of E. coli LeuRS D342A was measured using a reaction mixture consisting of 60 mM Tris, pH 7.0, 10 mM $MgCl_2$, and aminoacylated [$^3$H]-isoleucyl-$tRNA^{Leu}$ (50 µCi/ml). The reaction was initiated by the addition of 100 nM enzyme. The reaction was quenched by placing a 5 µt aliquot on a Whatman 1003323 filter pad pre-soaked in 10% (v/v) trichloroacetic acid (TCA). The pads were slowly shaken on ice in 5% TCA with four changes over a 1 hour time period. The pads were the washed with 70% ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The wild-type LeuRS deacylated the mischarged tRNA. However, *E. coli* LeuRS D342A only deacylated at low levels (FIG. 28).

Example 7

D345A—Prokaryotic LeuRS Mutation

In another embodiment, leucyl-tRNA synthetase mutants described herein are made for prokaryotic organisms including, but not limited to *E. coli* LeuRS D345A.

In the present example the *E. coli* LeuRS D345A mutation was introduced via the polymerase chain reaction (PCR) into the plasmid p15ec3-1 harboring the wild-type *E. coli* leuS gene to create plasmid pHAPPY-1-1-28. Expression of this gene from either plasmid yields an *E. coli* LeuRS fusion protein that contains an N-terminal six-histidine tag. The mutant leuS gene was amplified using 100 ng p15ec3-1 and 225 pmoles each of a forward and reverse primer [5'-GGGCACGACCAGCGCGCCTACGAGTTTGCC 3' (SEQ ID NO.:13) and 5' GGCAAACTCGTAGGCGCGCTG-GTCGTGCCC 3' (SEQ ID NO.:14), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pHAPPY-1-1-28) was isolated using Wizard miniprep kits (Promega; Madison, Wis.). Sequencing of pHAPPY-1-1-28was performed by Lone Star Labs (Houston, Tex.) using a primer (5'-CCGAAGGCGTGGAGATC-3') (SEQ ID NO.:6) that annealed upstream of the mutated DNA region.

Plasmid pHAPPY-1-1-28 harboring *E. coli* LeuRS D345A was used to transform *E. coli* strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the *E. coli* LeuRS D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The *E. coli* LeuRS D345A mutant containing a six-histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of $tRNA^{Leu}$ by the *E. coli* LeuRS D345A mutant was measured in a reaction containing 60 mM Tris, pH 7.5, 10 mM $MgCl_2$, 1 mM dithiothreitol (DTT), 4 mM ATP, 4 mg/ml crude *E. coli* tRNA, 21.5 µM [$^3$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The *E. coli* LeuRS D345A mutant leucylates $tRNA^{Leu}$ at a similar efficiency as the wild-type protein (FIGS. 18, 21, and 24).

Isoleucylation of $tRNA^{Leu}$ by *E. coli* LeuRS D345A was measured in a reaction containing 60 mM Tris pH 7.5, 10 mM $MgCl_2$, 1 mM dithiothreitol (DTT), 4 mM ATP, 4 mg/ml crude $tRNA^{Leu}$, 22 µM [$^3$H]-isoleucine (180 µCi/ml) and 1 µM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The *E. coli* LeuRS D345A protein aminoacylated $tRNA^{Leu}$ with isoleucine in contrast to the wild-type protein (FIG. 19, 23, 25).

Valylation of $tRNA^{Leu}$ by *E. coli* LeuRS D345A was measured in a reaction containing 60 mM Tris pH 7.5, 10 mM $MgCl_2$, 1 mM dithiothreitol (DTT), 4 mM ATP, 4 mg/ml crude $tRNA^{Leu}$, 72 µM [$^3$H]-valine (1250 µCi/ml) and 800 nM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type *E. coli* LeuRS. The *E. coli* LeuRS D345A protein aminoacylated low yields of tRNA$^{Leu}$ with valine in contrast to the wild-type protein (FIG. 26).

Figure 20:
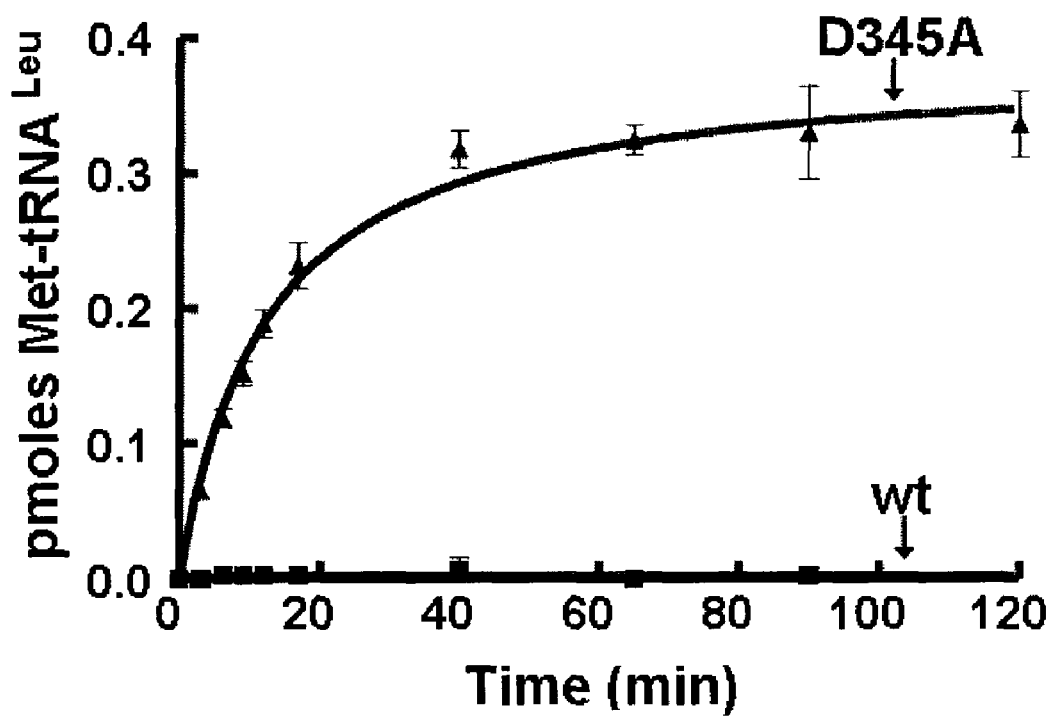
FIG. 20 depicts an *E. coli* LeuRS misaminoacylation assay of tRNA$^{Leu}$ with methionine using *E. coli* crude tRNA, wherein each reaction was repeated and averaged and symbols representing misaminoacylation activity by wild-type and mutant LeuRS are: wild-type (wt), solid square; D345A, solid triangle.

Methionylation of tRNA$^{Leu}$ by E. coli LeuRS D345A was measured in a reaction containing 60 mM Tris pH 7.5, 10 mM MgCl$_2$, 1 mM dithiothreitol (DTT), 4 mM ATP, 4 mg/ml crude tRNA$^{Leu}$, 22 µM [$^{35}$S]-methionine (303 µCi/ml) and 1 µM enzyme. The reaction was initiated by the addition of ATP and quenched by placing a 5 µl aliquot on a Whatman 1003323 filter pad pre-soaked in 5% (v/v) trichloroacetic acid (TCA) with 1 mM methionine. The pads were slowly shaken on ice in 5% TCA with 1 mM methionine with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS D345A protein aminoacylated low yields of tRNA$^{Leu}$ with methionine in contrast to the wild-type protein (FIGS. 20 and 27).

A 15.4 µl aliquot of 100 µM concentration (or 1540 pmoles) of tRNA$^{Leu}$ was aminoacylated with [$^{3}$H]-isoleucine in an isoleucylation reaction as described above using E. coli LeuRS D342A/D345A for 30 min at 37° C. The pH of the reaction was adjusted to 5.0 using acetic acid (0.1% v/v) and the aminoacylated isoleucyl-tRNA$^{Leu}$ immediately extracted using phenol/chloroform/isoamyl alcohol (25:24:1) (pH 5.1) (Fisher Scientific; Fair Lawn, N.J.). The aminoacylated isoleucyl-tRNA$^{Leu}$ was concentrated by ethanol precipitation, and resuspended in 50 mM KH$_2$PO$_4$ (pH 5.0) at a concentration of 50 µM. The aminoacylated isoleucyl-tRNA$^{Leu}$ was stored at −20° C.

The hydrolytic editing activity of E. coli LeuRS D345A was measured using a reaction mixture consisting of 60 mM Tris, pH 7.0, 10 mM MgCl$_2$, and aminoacylated [$^{3}$H]-isoleucyl-tRNA$^{Leu}$ (50 µCi/ml). The reaction was initiated by the addition of 100 nM enzyme. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were the washed with 70% ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The wild-type LeuRS deacylated the mischarged tRNA. However, E. coli LeuRS D345A did not deacylate the mischarged tRNA (FIG. 28).

Example 8

D342A/D345A—Prokaryotic LeuRS Mutation

In yet another embodiment, leucyl-tRNA synthetase mutants described herein are made for prokaryotic organisms including, but not limited to E. coli LeuRS D342A/D345A. In the present example the E. coli LeuRS D342A/D345A mutation was introduced via the polymerase chain reaction (PCR) into the plasmid p15ec3-1 harboring the wild-type E. coli leuS gene to create plasmid pHAPPY-1-1-29. Expression of this gene from either plasmid yields an E. coli LeuRS fusion protein that contains an N-terminal six-histidine tag. The mutant leuS gene was amplified using 100 ng p15ec3-1and 225 pmoles each of a forward and reverse primer [5' GGTAC-CGGGGCACGCCCAGCGCGCCTACGAGTTTGC 3' (SEQ ID NO.:15) and 5' GGCAAACTCGTAG-GCGCGCTGGGCGTGCCCCGGTAC 3' SEQ ID NO.16), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM (NH$_4$)$_2$SO$_4$, 2 mM MgSO$_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C, 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA (pHAPPY-1-1-29) was isolated using Wizard miniprep kits (Promega; Madison, Wis.). Sequencing of pHAPPY-1-1-29 was performed by Lone Star Labs (Houston, Tex.) using a primer (5'-CCGAAG-GCGTGGAGATC-3') (SEQ ID NO.:6) that annealed upstream of the mutated DNA region.

Plasmid pHAPPY-1-1-29 harboring E. coli LeuRS D342A/D345A was used to transform E. coli strain BL21 pLysS (Invitrogen Corporation; Carlsbad, Calif.). A 500 ml LB culture that included 100 µg/ml ampicillin was grown at 37° C. to an A$_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM Na$_2$HPO$_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS D342A/D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM Na$_2$HPO$_4$ (pH 7.0), 10 mM Tris, 500 mM NaCl and 10% glycerol. The E. coli LeuRS D342A/D345A mutant containing a six-histidine tag was eluted with 20 mM Na$_2$HPO$_4$ (pH 8.0), 10 mM Tris (pH 8.0), 300 mM NaCl, 100 mM imidazole and 10% glycerol. The elution fraction was concentrated and dialyzed into its final storage buffer of 20 mM Na$_2$HPO$_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of tRNA$^{Leu}$ by the E. coli LeuRS D342A/D345A mutant was measured in a reaction containing 60 mM Tris, pH 7.5, 10 mM MgCl$_2$, 1 mM dithiothreitol (DTT), 4 mM ATP, 4 mg/ml crude E. coli tRNA, 21.5 µM [$^{3}$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type $E.\ coli$ LeuRS. The $E.\ coli$ LeuRS D342A/D345A mutant leucylates tRNA$^{Leu}$ at a similar efficiency as the wild-type protein (FIG. 24).

Isoleucylation of tRNA$^{Leu}$ by $E.\ coli$ LeuRS D342A/D345A was measured in a reaction containing 60 mM Tris pH 7.5, 10 mM MgCl$_2$, 1 mM dithiothreitol (DTT), 4 mM ATP, 4 mg/ml crude tRNA$^{Leu}$, 22 μM [$^3$H]-isoleucine (180 μCi/mi) and 1 μM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type $E.\ coli$ LeuRS. The $E.\ coli$ LeuRS D342A!D345A protein aminoacylated tRNA$^{Leu}$ with isoleucine at high levels in contrast to the wild-type protein (FIG. 25).

Valylation of tRNA$^{Leu}$ by $E.\ coli$ LeuRS D342A/D345A was measured in a reaction containing 60 mM Tris pH 7.5, 10 mM MgCl$_2$, 1 mM dithiothreitol (DTT), 4 mM ATP, 4 mg/ml crude tRNA$^{Leu}$, 72 μM [$^3$H]-valine (1250 μCi/ml) and 800 nM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type $E.\ coli$ LeuRS. The $E.\ coli$ LeuRS D342A/D345A protein aminoacylated high yields of tRNA$^{Leu}$ with valine in contrast to the wild-type protein (FIG. 26).

Methionylation of tRNA$^{Leu}$ by $E.\ coli$ LeuRS D342A/D345A was measured in a reaction containing 60 mM Tris pH 7.5, 10 mM MgCl$_2$, 1 mM dithiothreitol (DTT), 4 mM ATP, 4 mg/ml crude tRNA$^{Leu}$, 22 μM [$^{35}$S]-methionine (303 μCi/ml) and 1 μM enzyme. The reaction was initiated by the addition of ATP and quenched by placing a 5 μl aliquot on a Whatman 1003323 filter pad pre-soaked in 5% (v/v) trichloroacetic acid (TCA) with 1 mM methionine. The pads were slowly shaken on ice in 5% TCA with 1 mM methionine with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type $E.\ coli$ LeuRS. The $E.\ coli$ LeuRS D342A/D345A protein aminoa-cylated high yields of tRNA$^{Leu}$ with methionine in contrast to the wild-type protein (FIG. 27).

A 15.4 μl aliquot of 100 μM concentration (or 1540 pmoles) of tRNA$^{Leu}$ was aminoacylated with [$^3$H]-isoleucine in an isoleucylation reaction as described above using $E.\ coli$ LeuRS D342A/D345A for 30 min at 37° C. The pH of the reaction was adjusted to 5.0 using acetic acid (0.1% v/v) and the aminoacylated isoleucyl-tRNA$^{Leu}$ immediately extracted using phenol/chloroform/isoamyl alcohol (25:24:1) (pH 5.1) (Fisher Scientific; Fair Lawn, N.J.). The aminoacylated iso-leucyl-tRNA$^{Leu}$ was concentrated by ethanol precipitation, and resuspended in 50 mM KH$_2$PO$_4$ (pH 5.0) at a concentration of 50 μM. The aminoacylated isoleucyl-tRNA$^{Leu}$ was stored at –20° C.

The hydrolytic editing activity of $E.\ coli$ LeuRS D342A/D345A was measured using a reaction mixture consisting of 60 mM Tris, pH 7.0, 10 mM MgCl$_2$, and aminoacylated [$^3$H]-isoleucyl-tRNA$^{Leu}$ (50 μCi/ml). The reaction was initiated by the addition of 100 nM enzyme. The reaction was quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were the washed with 70 % ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type $E.\ coli$ LeuRS. The wild-type LeuRS deacylated the mischarged tRNA. However, $E.\ coli$ LeuRS D342A/D345A did not deacylate the mischarged tRNA (FIG. 28).

Example 9

T252A/D345A—Prokaryotic LeuRS Mutation

In another embodiment, leucyl-tRNA synthetase mutants described herein are made for prokaryotic organisms including, but not limited to $E.\ coli$ LeuRS T252A1D345A.

In the present example the $E.\ coli$ LeuRS T252A/D345A mutation was introduced via the polymerase chain reaction (PCR) into the plasmid pMURe10 harboring the T252A $E.\ coli$ leuS gene to create plasmid pHAPPY2-1-1-19. Expression of this gene from either plasmid yields an $E.\ coli$ LeuRS fusion protein that contains an N-terminal six-histidine tag. The mutant leuS gene was amplified using 100 ng pMURe10 and 225 pmoles each of a forward and reverse primer [5' GGGCACGACCAGCGCGCCTACGAGTTTGCC 3' (SEQ ID NO.:17) and 5' GGCAAACTCGTAGGCGCGCTG-GTCGTGCCC 3' (SEQ ID NO.:18), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 μl of 20 mM tris(hydroxymethyl) aminomethane (Tris), pH 8.8, 10 mM KCl, 10 mM (NH$_4$)$_2$SO$_4$, 2 mM MgSO$_4$, 0.1% Triton X-100 and 100 μg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform $E.\ coli$ strain DH5α (Invitrogen Corporation; Carlsbad, Calif.). Colonies that contained the plasmid were grown and selected on LB media that contained 100 µg/ml ampicillin. The plasmid DNA (pHAPPY2-1-1-19) was isolated using Wizard miniprep kits (Promega; Madison, Wis.). Sequencing of pHAPPY2-1-1-19 was performed by Lone Star Labs (Houston, Tex.) using a primer (5'-CCGAAGGCGTGGAGATC-3') (SEQ ID NO.:6) that annealed upstream of the mutated DNA region.

Plasmid pHAPPY2-1-1-19 harboring E. coli LeuRS T252A/D345A was used to transform E. coli strain BL21 pLysS (Invitrogen Corporation; Carlsbad, Calif.). A 500 ml LB culture that included 100 1µg/ml ampicillin was grown at 37° C. to an $A_{600}$ of approximately 0.6. Protein expression was induced by the addition of 1 mM isopropyl-thiogalacto-pyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS T252A/D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS T252A/D345A mutant containing a six-histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of tRNA$^{Leu}$ by the E. coli LeuRS T252A/D345A mutant was measured in a reaction containing 60 mM Tris, pH 7.5, 10 mM $MgCl_2$, 1 mM dithiothreitol (DTT), 4 mM ATP, 4 mg/ml crude E. coli tRNA, 21.5 µM [$^3$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS T252A/D345A mutant leucylates tRNA$^{Leu}$ at a slightly lower efficiency as the wild-type protein (FIG. 21).

Isoleucylation of tRNA$^{Leu}$ by E. coli LeuRS T252A/D345A was measured in a reaction containing 60 mM Tris pH 7.5, 10 mM $MgCl_2$, 1 mM dithiothreitol (DTT), 4 mM ATP, 4 mg/ml crude tRNA$^{Leu}$, 22 µM [$^3$H]-isoleucine (180 µCi/ml) and 1 µM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS T252A/D345A protein aminoacylated tRNA$^{Leu}$ with isoleucine at high levels in contrast to the wild-type protein (FIG. 23).

A 15.4 µl aliquot of 100 µM concentration (or 1540 pmoles) of tRNA$^{Leu}$ was aminoacylated with [$^3$H]-leucine in a leucylation reaction as described above using the wild-type E. coli LeuRS for 1 hour at 37° C. The pH of the reaction was adjusted to 5.0 using acetic acid (0.1% v/v) and the aminoacylated isoleucyl-tRNA$^{Leu}$ immediately extracted using phenol/chloroform/isoamyl alcohol (25:24:1) (pH 5.1) (Fisher Scientific; Fair Lawn, N.J.). The aminoacylated isoleucyl-tRNA$^{Leu}$ was concentrated by ethanol precipitation, and resuspended in 50 mM $KH_2PO_4$ (pH 5.0) at a concentration of 50 µM. The aminoacylated isoleucyl-tRNA$^{Leu}$ was stored at −20° C.

The hydrolytic editing activity of E. coli LeuRS T252A/D345A was measured using a reaction mixture consisting of 60 mM Tris, pH 7.0, 10 mM $MgCl_2$, and aminoacylated [$^3$H]-leucyl-tRNA$^{Leu}$ (50 µCi/ml). The reaction was initiated by the addition of 100 nM enzyme. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were the washed with 70% ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The wild-type LeuRS as well as the E. coli LeuRS T252A/D345A did not deacylate the Leu-tRNA (FIG. 22).

Example 10

T252Y/D342A/D345A—Prokaryotic LeuRS Mutation

In still another embodiment, leucyl-tRNA synthetase mutants described herein are made for prokaryotic organisms including, but not limited to E. coli LeuRS T252Y/D342A/D345A.

In the present example the E. coli LeuRS T252Y/D342A/D345A mutation was introduced via the polymerase chain reaction (PCR) into the plasmid pHAPPY2-1-1-29 harboring the mutant D342A/D345A E. coli leuS gene to create plasmid pHAPPY2-1-1-23. Expression of this gene from either plasmid yields an E. coli LeuRS fusion protein that contains an N-terminal six-histidine tag. The mutant leuS gene was amplified using 100 ng pHAPPY2-1-1-29 and 225 pmoles each of a forward and reverse primer [5'-CCC GCC CGG ACT ACT TTA TGG GTT GTA CC-3' (SEQ ID NO.:19) and 5'-GGT ACA ACC CAT AAA GTA GTC CGG GCG GG-3' (SEQ ID NO.:8), respectively] that encoded the gene mutation. The PCR reaction mixture also contained 10 pmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min), annealing (60° C., 30 sec) and extension (68° C., 20 min). The PCR products may be stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA for pHAPPY2-1-1-23 was isolated using Wizard miniprep kits (Promega; Madison, Wis.). Sequencing of pHAPPY2-1-1-23 was performed by Lone Star Labs (Houston, Tex.) using a primer (5'-GAAGGCGTGGAGAT-3') (SEQ ID NO.:20) that annealed upstream of the mutated DNA region.

The plasmid pHAPPY2-1-1-23 harboring E. coli LeuRS T252Y/D342A/D345A was used to transform E. coli strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS T252Y/D342A/D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS T252Y/D342A/D345A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Figure 48:
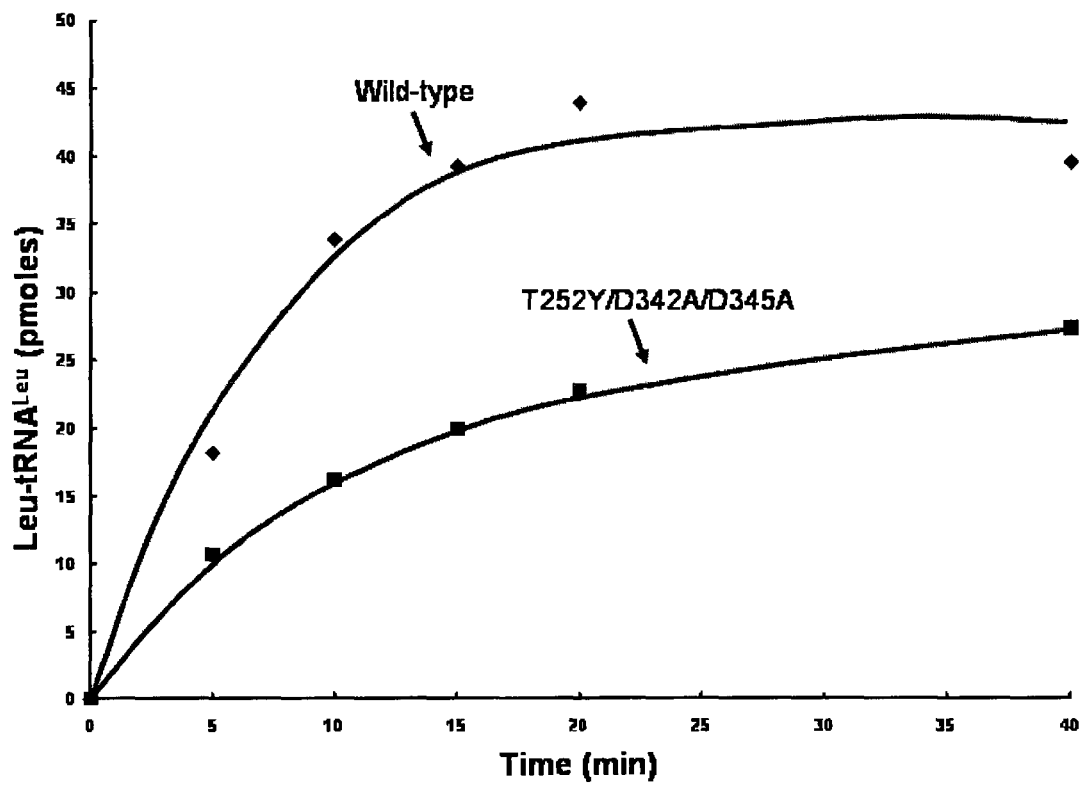
FIG. 48 is a graph of aminoacylation of tRNA$^{Leu}$ with leucine by E. coli wild-type and a CP1-based triple mutant LeuRS, wherein symbols representing aminoacylation activity by wild-type and T252Y/D342A/D345A mutant LeuRSs are: wild-type (wt), solid diamond; T252Y/D342A/D345A, solid square.

Leucylation of tRNA$^{Leu}$ by the E. coli LeuRS T252Y/D342A/D345A mutant was measured in a reaction containing 60 mM Tris, pH 7.5, 10 mM $MgCl_2$, 1 mM dithiothreitol (DTT), 4 mM ATP, 8 mg/ml crude E. coli tRNA, 10.93 µM [$^3$H]-leucine (150 µCi/ml) and 10 nM enzyme. The reaction was initiated by the addition of ATP. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS T252Y/D342A/D345A mutant leucylates tRNA$^{Leu}$ at a lower efficiency than the wild-type protein (FIG. 48).

A 44 µl aliquot of 40 mg/ml crude E. coli tRNA was aminoacylated with [$^3$H]-isoleucine in an isoleucylation reaction containing 60 mM Tris pH 7.5, 10 mM $MgCl_2$, 1 mM dithiothreitol (DTT), 4 mM ATP, 4 mg/ml crude tRNA$^{Leu}$, 22 µM [$^3$H]-isoleucine (180 µCi/ml) and 1 µM enzyme using E. coli LeuRS D342A/D345A for 60 min at 37° C. The pH of the reaction was adjusted to 5.0 using acetic acid (0.1% v/v) and the aminoacylated isoleucyl-tRNA$^{Leu}$ immediately extracted using phenol/chloroform/isoamyl alcohol (25:24:1) (pH 5.1) (Fisher Scientific; Fair Lawn, N.J.). The aminoacylated isoleucyl-tRNA$^{Leu}$ was concentrated by ethanol precipitation, and resuspended in 50 mM $KH_2PO_4$ (pH 5.0) at a concentration of 50 µM. The aminoacylated isoleucyl-tRNA$^{Leu}$ was stored at –20° C.

Figure 49:
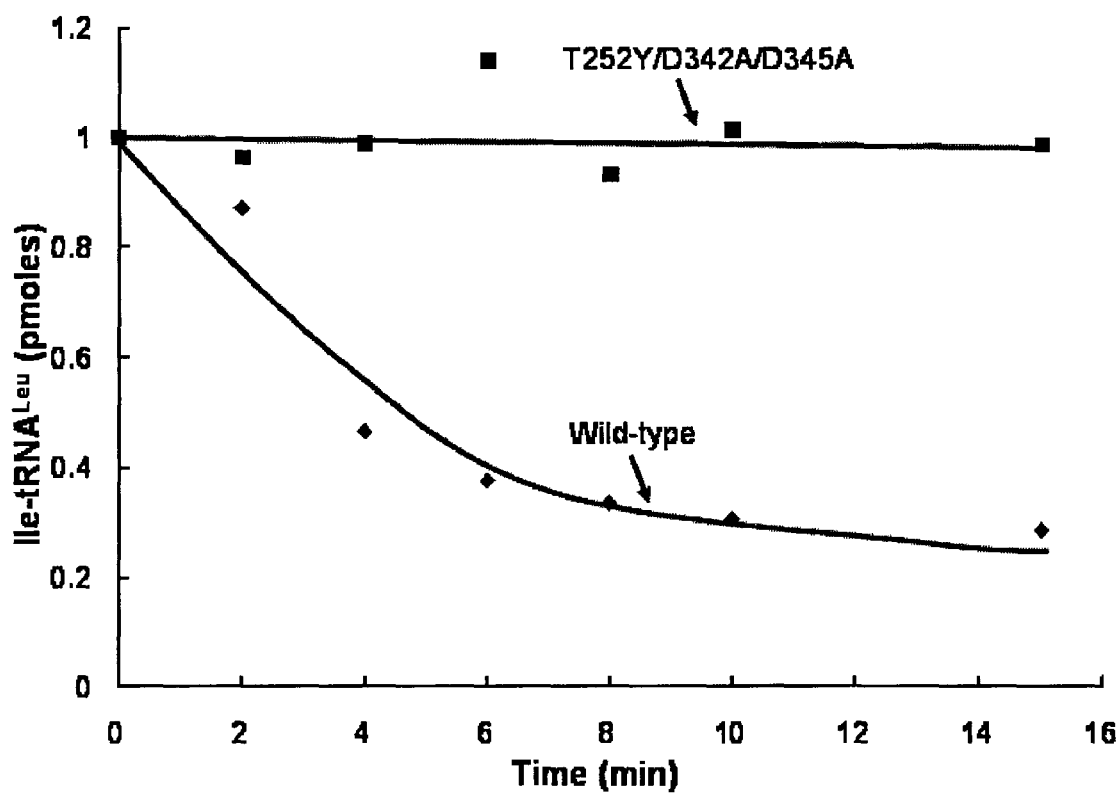
FIG. 49 depicts hydrolytic post-transfer editing of mischarged Ile-tRNA$^{Leu}$, wherein symbols representing amino acid editing activity by wild-type and T252Y/D342A/D345A mutant LeuRSs are: wild-type (wt), solid diamond; T252Y/D342A/D345A, solid square.

The hydrolytic editing activity of E. coli LeuRS T252Y/D342A/D345A was measured using a reaction mixture consisting of 60 mM Tris, pH 7.0, 10 mM $MgCl_2$, and 25% aminoacylated [$^3$H]-isoleucyl-tRNA$^{Leu}$. The reaction was initiated by the addition of 200 nM enzyme. The reaction was quenched by placing a 5 µl aliquot on a Whatman 1003323 filter pad pre-soaked in 10% (v/v) trichloroacetic acid (TCA). The pads were slowly shaken on ice in 5% TCA with four changes over a 1 hour time period. The pads were the washed with 70% ethanol and subsequently with ether (anhydrous). The pads were dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The wild-type LeuRS deacylated the mischarged tRNA. However, E. coli LeuRS T252Y/D342A/D345A did not hydrolyze the misacylated tRNA. (FIG. 49).

Example 11

M40S/T252Y/D342A/D345A—Prokaryotic LeuRS Mutation

Another embodiment of the present invention include leucyl-tRNA synthetase mutants described herein are made for prokaryotic organisms including, but not limited to E. coli LeuRS M40S/T252Y/D342A/D345A.

In the present example the E. coli LeuRS M40S/T252Y/D342A/D345A mutation was introduced via the polymerase chain reaction (PCR) into the plasmid pHAPPY2-1-1-23 harboring mutant E. coli leuS T252Y/D342AID345A gene to create plasmid pHAPPY2-1-1/3-46. Expression of this gene from either plasmid yields an E. coli LeuRS fusion protein that contains an N-terminal six-histidine tag. The mutant leuS gene was amplified using 100 ng pHAPPY2-1-1-23 and 225 pmoles each of a forward and reverse primer [5'-GAA GTA TTA CTG CCT GTC TAG CCT TCC CTA TCC TTC TGG TCG-3' (SEQ ID NO.:21) and 5'-CGA CCA GAA GGA TAG GGA AGG CTA GAC AGG CAG TAA TAC TTC-3' (SEQ ID NO.22), respectively] that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris (hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68 ° C, 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA (pHAPPY2-1-1/3-46) was isolated using Wizard miniprep kits (Promega; Madison, Wis.). Sequencing of pHAPPY2-1-1/3-46 was performed by Lone Star Labs (Houston, Tex.) using a primer Ecr 785 (5'-GTT GTC GTA CGT CCA CGG-3') (SEQ ID NO.:23) that annealed upstream of the mutated DNA region.

Plasmid pHAPPY2-1-1/3-46 harboring E. coli LeuRS M40S/T252Y/D342A/D345A was used to transform E. coli strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS M40S/T252Y/D342A/D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS M40S/T252Y/D342A/D345A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of tRNA$^{Leu}$ by the E. coli LeuRS M40S/T252Y/D342A/D345A mutant was measured in a reaction containing 60 mM Tris, pH 7.5, 10 mM $MgCl_2$, 1 mM dithiothreitol (DTT), 4 mM ATP, 4 mg/ml crude E. coli tRNA, 10.76 µM [$^3$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS M40S/T252Y/D342A/D345A mutant leucylates tRNA$^{Leu}$ at a lower rate compared to the wild-type protein (FIG. 29).

Activation of leucine by the E. coli LeuRS M40S/T252Y/D342A/D345A mutant was measured in an amino acid-dependent pyrophosphate exchange assay. The reaction contained 50 mM N-2-Hydroxyethylpiperazine-N'-2-ethanesulfonic acid (HEPES), pH 8.0, 1 mM ATP, 10 MM $MgCl_2$, 1 mM DTT, and 1 mM [$^{32}$P]-pyrophosphate (53.3 µCi/ml), 50 nM enzyme, and 250 µM leucine. The reaction was initiated with the addition of leucine. TLC cellulose PEI plates (Scientific Adsorbents Inc.) were pre-run in water for 2 hours. 2 µL aliquots of the pyrophosphate reaction were removed at 5, 10, 20, 40, and 80 minutes and placed on the pre-run TLC plates to quench the reaction. The TLC plates were placed in a 75 mM $KH_2PO_4$, pH 3.5, 4 M urea running buffer, and incubated for until the buffer front reached the top of the TLC plate. The TLC plates were dried, wrapped in saran wrap, and placed onto a phosphorimaging screen in a Fujifilm BAS 2040 cassette. The phosphorimaging screen was imaged in the Fujix BAS-1000 phosphorimager and the amount of radiolabel present in the spots on the plates quantified using the quantitation mode of the ImageGuage V3.0 software program. The E. coli LeuRS M40S/T252Y/D342A/D345A mutant activates leucine at a slightly lower efficiency than the wild-type LeuRS protein (FIG. 30).

Activation of norvaline by the E. coli LeuRS M40S/T252Y/D342A/D345A mutant was measured in an amino acid-dependent pyrophosphate exchange assay. The reaction contained 50 mM N-2-Hydroxyethylpiperazine-N'-2-ethanesulfonic acid (HEPES), pH 8.0, 1 mM ATP, 10 mM $MgCl_2$, 1 mM DTT, and 1 mM [$^{32}$P]-pyrophosphate (53.3 µCi/ml), 50 nM enzyme, and 250 µM norvaline. The reaction was initiated with the addition of norvaline. TLC cellulose PEI plates (Scientific Adsorbents Inc.) were pre-run in water for 2 hours. 2 µL aliquots of the reaction were removed at 5, 10, 20, 40, and 80 minutes and placed on the pre-run TLC plates to quench the reaction. The TLC plates were placed in a 75 mM $KH_2PO_4$, pH 3.5, 4 M urea running buffer, and allowed to run for 3 hours. The TLC plates were dried, wrapped in saran wrap, and placed on a phosphoimager screen in a Fujifilm BAS 2040 cassette. The phosphoimaging screen was imaged in the phosphorimager and the amount of radiolabel present in the spots on the plates quantified using the quantitation mode of the ImageGuage V3.0 software program. The E. coli LeuRS M40S/T252Y/D342A/D345A mutant activates norvaline at a significantly lower efficiency than the wild-type LeuRS protein (FIG. 31). Kinetic measurements demonstrated that the E. coli LeuRS M40S/T252Y/D342A/D345A mutant discriminates leucine versus norvaline more efficiently than the wild type LeuRS enzyme.

Example 12

Y330A—Prokaryotic LeuRS Mutation

In another embodiment, leucyl-tRNA synthetase mutants described herein are made for prokaryotic organisms including, but not limited to E. coli LeuRS Y330A.

In the present example the E. coli LeuRS Y330A mutation was introduced via the polymerase chain reaction (PCR) into the plasmid p15ec3-1 harboring the wild-type E. coli leuS gene to create plasmid pMURe13. Expression of this gene from either plasmid yields an E. coli LeuRS fusion protein that contains an N-terminal six-histidine tag. The mutant leuS gene was amplified using 100 ng p15ec3-1 and 225 pmoles each of a forward and reverse primer (5'-CTTCGTAT-TGATGGAGGCCGGCACGGGCGCAG-3' (SEQ ID NO.:24) and 5'-GAAGCATAACTACCTCCGGCCGTGC-CCGCGTC-3' (SEQ ID NO.:25), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA (pMURe13) was isolated using Wizard miniprep kits (Promega; Madison, Wis.). Sequencing of pMURe13 was performed by Lone Star Labs (Houston, Tex.) using a primer (5'-CGGCTCTGAGCCAGATC-3') (SEQ ID NO.: 26) that annealed upstream of the mutated DNA region.

Plasmid pMURe13 harboring E. coli LeuRS Y330A was used to transform E. coli strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS Y330A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The E. coli LeuRS Y330A mutant containing a six-histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Leucylation of $tRNA^{Leu}$ by the E. coli LeuRS Y330A mutant was measured in a reaction containing 60 mM Tris, pH 7.5, 10 mM $MgCl_2$, 1 mM dithiothreitol (DTT), 4 mM ATP, 4 mg/ml crude E. coli tRNA, 21.5 µM [$^3$H]-leucine (150 µCi/ml) and 5 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type E. coli LeuRS. The E. coli LeuRS Y330A mutant leucylates $tRNA^{Leu}$ at a higher efficiency than the wild-type protein (FIG. 32).

Example 13

T319Y—Eukaryotic LeuRS Mutation

Another embodiment of the present invention include leucyl-tRNA synthetase mutants described herein are made for eukaryotic organisms including, but not limited to yeast cytoplasmic LeuRS T319Y.

In the present example the S. cerevisiae cytoplasmic LeuRS T319Y mutation was introduced via the polymerase chain reaction (PCR) into the plasmid p32YL-2-3 harboring yeast CDC60 gene to create plasmid pHAPPY1-1-1-8. Expression of this gene from either plasmid yields a S. cerevisiae LeuRS fusion protein that contains an N-terminal six-histidine tag. The mutant CDC60 gene was amplified using 100 ng p32YL-2-3 and 125 ng each of a forward and reverse primer (5'-GCC ACG TTG AGA CCG GAA <u>TAT</u> ATG TAT GGA CAA AC-3' (SEQ ID NO.:27) and 5'-GTT TGT CCA TAC AT<u>ATAT</u> TCC GGT CTC AAC GTG GC-3' (SEQ ID NO.:28), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-00 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform E. coli strain DH5α (Invitrogen Corporation; Carlsbad, Calif.). Colonies that contained the plasmid were grown and selected on LB media that contained 100 µg/ml ampicillin. The plasmid DNA (pHAPPY1-1-1-8) was isolated using Wizard miniprep kits (Promega; Madison, Wis.). Sequencing of pHAPPY1-1-1-8 was performed by Lone Star Labs (Houston, Tex.) using a primer (5'-GGT GTT ACA CCA CAA GAA TAT ATT GGT-3') (SEQ ID NO.:29) that annealed upstream of the mutated DNA region.

Plasmid pHAPPY1-1-1-8 harboring yeast cytoplasmic LeuRS T319Y was used to transform competent E. coli BL21-CodonPlus cells (Stratagene; La Jolla, Calif.). A 500 ml LB culture that included 100 µg/ml ampicillin and 34 µg/ml chloramphenicol was grown at 37° C to an $A_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS T319Y mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The yeast cytoplasmic LeuRS T319Y mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of tRNA$^{Leu}$ by the yeast cytoplasmic LeuRS T319Y mutant was measured in a reaction containing 60 mM Tris, pH 7.5, 10 mM $MgCl_2$, 1 mM dithiothreitol (DTT), 4 mM ATP, 5 mg/ml crude yeast tRNA, 30 µM [$^{14}$C]-leucine (9.21 µCi/ml) and 100 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic LeuRS T319Y mutant leucylates tRNA$^{Leu}$ at a slightly lower efficiency than the wild-type protein (FIG. 33).

Isoleucylation of tRNA$^{Leu}$ by yeast cytoplasmic LeuRS T319Y was measured in a reaction containing 60 mM Tris pH 7.5, 10 mM $MgCl_2$, 1 mM dithiothreitol (DTT), 4 mM ATP, 5 mg/ml crude yeast tRNA, 22.25 µM [$^3$H]-isoleucine (200 µCi/ml) and 750 nM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS T319Y protein aminoacylated tRNA$^{Leu}$ with isoleucine yielding isoleucine-tRNA$^{Leu}$ in contrast to the wild-type protein (FIG. 34).

Example 14

T319Y/D419A—Eukaryotic LeuRS Mutation

In another embodiment, leucyl-tRNA synthetase mutants described herein are made for eukaryotic organisms including, but not limited to yeast cytoplasmic LeuRS T319Y/D419A.

In the present example the *S. cerevisiae* cytoplasmic LeuRS T319Y/D419A mutation was introduced via the polymerase chain reaction (PCR) into the plasmid p32-AMW1 harboring yeast mutant CDC60 gene encoding the D419A substitution to create plasmid pHAPPY1-1-1-9. Expression of this gene from either plasmid yields a *S. cerevisiae* LeuRS fusion protein that contains an N-terminal six-histidine tag. The mutant CDC60 gene was amplified using 100 ng p32-AMW1 and 125 ng each of a forward and reverse primer (5'-GCC ACG TTG AGA CCG GAA TAT ATG TAT GGA CAA AC-3' (SEQ ID NO.:27) and 5'-GTT TGT CCA TAC AT ATAT TCC GGT CTC AAC GTG GC-3' (SEQ ID NO.:28), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pHAPPY1-1-1-9) was isolated using Wizard miniprep kits (Promega; Madison, Wis.). Sequencing of pHAPPY1-1-1-9 was performed by Lone Star Labs (Houston, Tex.) using a primer (5'-GGT GTT ACA CCA CAA GAA TAT ATT GGT-3') (SEQ ID NO.:29) that annealed upstream of the mutated DNA region.

Plasmid pHAPPY1-1-1-9 harboring yeast cytoplasmic LeuRS T319Y/D419A was used to transform competent *E. coli* BL21-CodonPlus cells (Stratagene; La Jolla, Calif.). A 500 ml LB culture that included 100 µg/ml ampicillin and 34 µg/ml chloramphenicol was grown at 37° C. to an $A_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS T319Y/D419A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The yeast cytoplasmic LeuRS T319Y/D419A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of tRNA$^{Leu}$ by the yeast cytoplasmic LeuRS T319Y/D419A mutant was measured in a reaction containing 60 mM Tris, pH 7.5, 10 mM $MgCl_2$, 1 mM dithiothreitol (DTT), 4 mM ATP, 5 mg/ml crude yeast tRNA, 30 µM [$^{14}$C]-leucine (9.21 µCi/ml) and 100 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of Scinti-Safe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic LeuRS T319Y/D419A mutant leucylates tRNA$^{Leu}$ at a slightly lower efficiency than the wild-type protein (FIG. 35).

Figure 36:
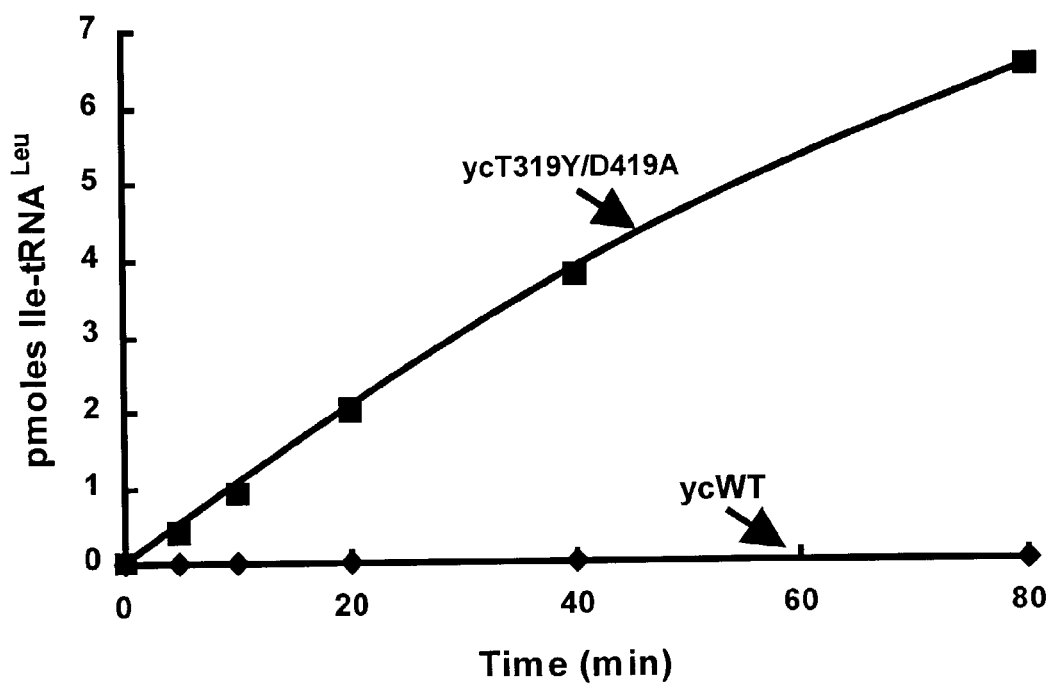
FIG. 36 is a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycT319Y/D419A, closed square.

Isoleucylation of tRNA$^{Leu}$ by yeast cytoplasmic LeuRS T319Y/D419A was measured in a reaction containing 60 mM Tris pH 7.5, 10 mM MgCl$_2$, 1 mM dithiothreitol (DTT), 4 mM ATP, 5 mg/ml crude yeast tRNA, 22.25 μM [$^3$H]-isoleucine (200 μCi/ml) and 750 nM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS T319Y/D419A protein aminoacylated tRNA$^{Leu}$ at high levels with isoleucine yielding isoleucine-tRNA$^{Leu}$ in contrast to the wild-type protein (FIG. 36).

Example 15

N415A—Eukaryotic LeuRS Mutation

In another embodiment, leucyl-tRNA synthetase mutants described herein are made for eukaryotic organisms including, but not limited to yeast cytoplasmic LeuRS N415A.

In the present example the *S. cerevisiae* cytoplasmic LeuRS N415A mutation was introduced via the polymerase chain reaction (PCR) into the plasmid p32YL-2-3 harboring yeast CDC60 gene to create plasmid pHAPPY1-1-1-55. Expression of this gene from either plasmid yields a *S. cerevisiae* LeuRS fusion protein that contains an N-terminal six-histidine tag. The mutant CDC60 gene was amplified using 100 ng p32YL-2-3 and 125 ng each of a forward and reverse primer (5'-CAC GTG TGT ACC ATC TGC TTC ACC AGA TGA CTA C-3' (SEQ ID NO.:30) and 5'-GTA GTC ATC TGG TGA AGC AGA TGG TAC ACA CGT G-3' (SEQ ID NO.:31), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 μl of 20 mM tris (hydroxymethyl) aminomethane (Tris), pH 8.8, 10 mM KCl, 10 mM (NH$_4$)$_2$SO$_4$, 2 mM MgSO$_4$, 0.1% Triton X-100 and 100 μg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 μg/ml ampicillin. The plasmid DNA (pHAPPY1-1-1-55) was isolated using Wizard miniprep kits (Promega; Madison, Wis.). Sequencing of pHAPPY1-1-1-55 was performed by Lone Star Labs (Houston, Tex.) using a primer (5'-GCT ACC AAG GGT ACT GGT GTC GTC-3') (SEQ ID NO.:32) that annealed upstream of the mutated DNA region.

Plasmid pHAPPY1-1-1-55 harboring yeast cytoplasmic LeuRS N415A was used to transform competent *E. coli* BL21-CodonPlus cells (Stratagene; La Jolla, Calif.). A 500 ml LB culture that included 100 μg/ml ampicillin and 34 μg/ml chloramphenicol was grown at 37° C to an A$_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM Na$_2$HPO$_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS N415A mutant was mixed gently at 4° C. for 30 minutes. The resin was separated from the supernatant in a clinical centrifuge (International Equipment Co.; Needham Heights, Mass.). The resin was washed four times with 10 ml of 20 mM Na$_2$HPO$_4$ (pH 7.0), 10 mM Tris, 500 mM NaCl and 10% glycerol. The yeast cytoplasmic LeuRS N415A mutant containing a six histidine tag was eluted with 20 mM Na$_2$HPO$_4$ (pH 8.0), 10 mM Tris (pH 8.0), 300 mM NaCl, 100 mM imidazole and 10% glycerol. The elution fraction was concentrated and dialyzed into its final storage buffer of 20 mM Na$_2$HPO$_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of tRNA$^{Leu}$ by the yeast cytoplasmic LeuRS N415A mutant was measured in a reaction containing 60 mM Tris, pH 7.5, 10 mM MgCl$_2$, 1 mM dithiothreitol (DTT), 4 mM ATP, 5 mg/ml crude yeast tRNA, 30 μM [$^{14}$C]-leucine (9.21 μCi/ml) and 100 nM enzyme. The reaction was initiated by the addition of ATP. The reaction was quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic e LeuRS N415A mutant leucylates tRNA$^{Leu}$ at a slightly lower efficiency than the wild-type protein (FIG. 37).

Isoleucylation of tRNA$^{Leu}$ by yeast cytoplasmic LeuRS N415A was measured in a reaction containing 60 mM Tris pH 7.5, 10 mM MgCl$_2$, 1 mM dithiothreitol (DTT), 4 mM ATP, 5 mg/ml crude yeast tRNA, 22.25 μM [$^3$H]-isoleucine (200 μCi/ml) and 750 nM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS N415A protein aminoacylated tRNA$^{Leu}$ with isoleucine yielding isoleucine-tRNA$^{Leu}$ in contrast to the wild-type protein (FIG. 38).

Example 16

N415A/D419A—Eukaryotic LeuRS Mutation

Other embodiments of the present invention include leucyl-tRNA synthetase mutants described herein are made for eukaryotic organisms including, but not limited to yeast cytoplasmic LeuRS N415A/D419A.

In the present example the *S. cerevisiae* cytoplasmic LeuRS N415A/D419A mutation was introduced via the polymerase chain reaction (PCR) into the plasmid p32-AMW1 harboring the yeast mutant CDC60 gene encoding the D419A substitution to create plasmid pHAPPY1-1-1-59. Expression of this gene from either plasmid yields a *S. cerevisiae* LeuRS fusion protein that contains an N-terminal six-histidine tag. The mutant CDC60 gene was amplified using 100 ng p32-AMW1 and 125 ng each of a forward and reverse primer (5'-CAC GTG TGT ACC ATC TGC TTC ACC AGA TGC CTA C-3' (SEQ ID NO.:30) and 5'-GTA GGC ATC TGG TGA AGC AGA TGG TAC ACA CGT G-3' (SEQ ID NO.:31), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 μl of 20 mM tris(hydroxymethyl) aminomethane (Tris), pH 8.8, 10 mM KCl, 10 mM (NH$_4$)$_2$SO$_4$, 2 mM MgSO$_4$, 0.1% Triton X-100 and 100 μg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 μg/ml ampicillin. The plasmid DNA (pHAPPY1-1-1-59) was isolated using Wizard miniprep kits (Promega; Madison, Wis.). Sequencing of pHAPPY1-1-1-59 was performed by Lone Star Labs (Houston, Tex.) using a primer ycF 1356 (5'-GCT ACC AAG GGT ACT GGT GTC GTC-3') (SEQ ID NO.:32) that annealed upstream of the mutated DNA region.

Plasmid pHAPPY1-1-1-59 harboring yeast cytoplasmic LeuRS N415A/D419A was used to transform competent *E. coli* BL21-CodonPlus cells (Stratagene; La Jolla, Calif.). A 500 ml LB culture that included 100 μg/ml ampicillin and 34 μg/ml chloramphenicol was grown at 37° C. to an A$_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM Na$_2$HPO$_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS N415A/D419A mutant was mixed gently at 4° C. for 30 minutes. The resin was separated from the supernatant in a clinical centrifuge (International Equipment Co.; Needham Heights, Mass.). The resin was washed four times with 10 ml of 20 mM Na$_2$HPO$_4$ (pH 7.0), 10 mM Tris, 500 mM NaCl and 10% glycerol. The yeast cytoplasmic LeuRS N415A/D419A mutant containing a six histidine tag was eluted with 20 mM Na$_2$HPO$_4$ (pH 8.0), 10 mM Tris (pH 8.0), 300 mM NaCl, 100 mM imidazole and 10% glycerol. The elution fraction was concentrated and dialyzed into its final storage buffer of 20 mM Na$_2$HPO$_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of tRNA$^{Leu}$ by the yeast cytoplasmic LeuRS N415A/D419A mutant was measured in a reaction containing 60 mM Tris, pH 7.5, 10 mM MgCl$_2$, 1 mM dithiothreitol (DTT), 4 mM ATP, 5 mg/ml crude yeast tRNA, 30 μM [$^{14}$C]-leucine (9.21 μCi/ml) and 100 nM enzyme. The reaction was initiated by the addition of ATP. The reaction was quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic LeuRS N415A/D419A mutant leucylates tRNA$^{Leu}$ at a slightly lower efficiency than the wild-type protein (FIG. 39).

Figure 40:
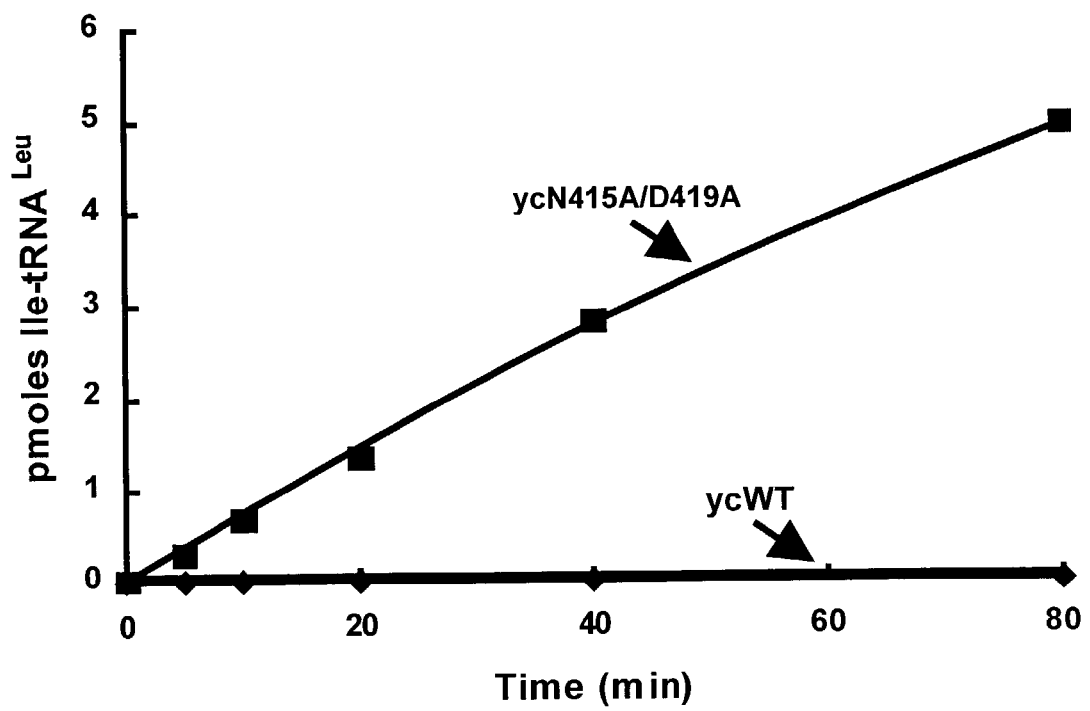
FIG. 40 is a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycN415A/D419A, closed square.

Isoleucylation of tRNA$^{Leu}$ by yeast cytoplasmic LeuRS N415A/D419A was measured in a reaction containing 60 mM Tris pH 7.5, 10 mM MgCl$_2$, 1 mM dithiothreitol (DTT), 4 mM ATP, 5 mg/ml crude yeast tRNA, 22.25 μM [$^3$H]-isoleucine (200 μCi/ml) and 750 nM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS N415A/D419A protein aminoacylated tRNA$^{Leu}$ with isoleucine yielding isoleucine-tRNA$^{Leu}$ in contrast to the wild-type protein (FIG. 40).

Example 17

S416A/D419A—Eukaryotic LeuRS Mutation

Still other embodiments of the present invention include leucyl-tRNA synthetase mutants described herein are made for eukaryotic organisms including, but not limited to yeast cytoplasmic LeuRS S416A/D419A.

In the present example the *S. cerevisiae* cytoplasmic LeuRS S416A/D419A mutation was introduced via the polymerase chain reaction (PCR) into the plasmid p32-AMW1 harboring the yeast mutant CDC60 gene encoding the D419A substitution to create plasmid pHAPPY1-1-1-57. Expression of this gene from either plasmid yields a *S. cerevisiae* LeuRS fusion protein that contains an N-terminal six-histidine tag. The mutant CDC60 gene was amplified using 100 ng p32-AMW1 and 125 ng each of a forward and reverse primer (5'-CGT GTG TAC CAT CTA ATG CAC CAG ATG CCT AC-3' (SEQ ID NO.:33) and 5'-GTA GGC ATC TGG TGC ATT AGA TGG TAC ACA CG-3' (SEQ ID NO.:34), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 μl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 pg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 μg/ml ampicillin. The plasmid DNA (pHAPPY1-1-1-57) was isolated using Wizard miniprep kits (Promega; Madison, Wis.). Sequencing of pHAPPY1-1-1-57 was performed by Lone Star Labs (Houston, Tex.) using a primer ycF 1356 (5'-GCT ACC AAG GGT ACT GGT GTC GTC-3') (SEQ ID NO.:32) that annealed upstream of the mutated DNA region.

Plasmid pHAPPY1-1-1-57 harboring yeast cytoplasmic LeuRS S416A/D419A was used to transform competent *E. coli* BL21-CodonPlus cells (Stratagene; La Jolla, Calif.). A 500 ml LB culture that included 100 μg/ml ampicillin and 34 μg/ml chloramphenicol was grown at 37° C. to an $A_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS S416A/D419A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The yeast cytoplasmic LeuRS S416A/D419A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of $tRNA^{Leu}$ by the yeast cytoplasmic LeuRS S416A/D419A mutant was measured in a reaction containing 60 mM Tris, pH 7.5, 10 mM $MgCl_2$, 1 mM dithiothreitol (DTT), 4 mM ATP, 5 mg/ml crude yeast tRNA, 30 μM [$^{14}$C]-leucine (9.21 μCi/ml) and 100 nM enzyme. The reaction was initiated by the addition of ATP. The reaction was quenched by placing a 5 1l aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared those from experiments performed in parallel using the wild-type yeast LeuRS. The yeast cytoplasmic LeuRS S416A/D419A mutant leucylates $tRNA^{Leu}$ similar to the wild-type protein (FIG. 41).

Figure 42:
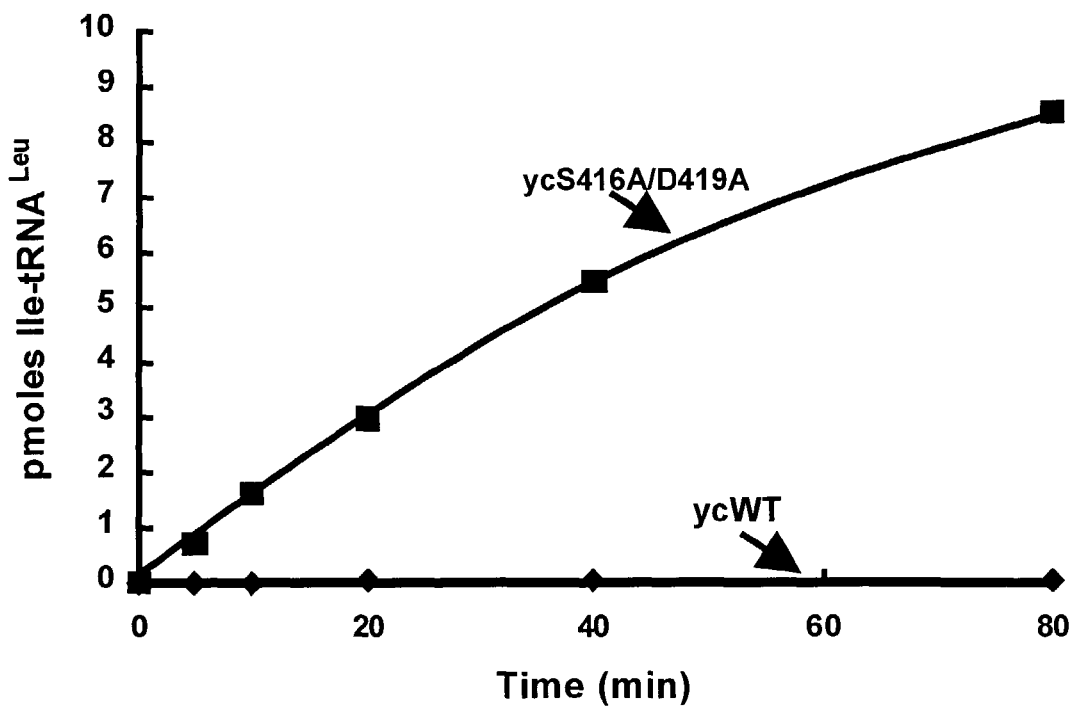
FIG. 42 is a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycS416A/D419A, closed square.

Isoleucylation of $tRNA^{Leu}$ by yeast cytoplasmic LeuRS S416A/D419A was measured in a reaction containing 60 mM Tris pH 7.5, 10 mM $MgCl_2$, 1 mM dithiothreitol (DTT), 4 mM ATP, 5 mg/ml crude yeast tRNA, 22.25 μM [$^{3}$H]-isoleucine (200 μCi/ml) and 750 nM enzyme. The reaction was initiated by the addition of ATP and quenched by placing a 5 μl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS S416A/D419A protein aminoacylated $tRNA^{Leu}$ with isoleucine yielding isoleucine-$tRNA^{Leu}$ in contrast to the wild-type protein (FIG. 42).

Example 18

D418A—Eukaryotic LeuRS Mutation

Still other embodiments of the present invention include leucyl-tRNA synthetase mutants described herein are made for eukaryotic organisms including, but not limited to yeast cytoplasmic LeuRS D418A.

In the present example the *S. cerevisiae* cytoplasmic LeuRS D418A mutation was introduced via the polymerase chain reaction (PCR) into the plasmid p32YL-2-3 harboring yeast CDC60 gene to create plasmid pHAPPY1-1-1-56. Expression of this gene from either plasmid yields a *S. cerevisiae* LeuRS fusion protein that contains an N-terminal six-histidine tag. The mutant CDC60 gene was amplified using 100 ng p32YL-2-3 and 125 ng each of a forward and reverse primer (5'-CCA TCT AAT TCA CCA GCT GAC TAC ATT ACC ACC-3' (SEQ ID NO.:35) and 5'-GGT GGT AAT GTA GTC AGC TGG TGA ATT AGA TGG-3' (SEQ ID NO.:36), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris (hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pHAPPY1-1-1-56) was isolated using Wizard miniprep kits (Promega; Madison, Wis.). Sequencing of pHAPPY1-1-1-56 was performed by Lone Star Labs (Houston, Tex.) using a primer ycF 1356 (5'-GCT ACC AAG GGT ACT GGT GTC GTC-3') (SEQ ID NO.:32) that annealed upstream of the mutated DNA region.

Plasmid pHAPPY1-1-1-56 harboring yeast cytoplasmic LeuRS D418A was used to transform competent *E. coli* BL21-CodonPlus cells (Stratagene; La Jolla, Calif.). A 500 ml LB culture that included 100 µg/ml ampicillin and 34 µg/ml chloramphenicol was grown at 37° C to an $A_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS D418A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The yeast cytoplasmic LeuRS D418A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of $tRNA^{Leu}$ by the yeast cytoplasmic LeuRS D418A mutant was measured in a reaction containing 60 mM Tris, pH 7.5, 10 mM $MgCl_2$, 1 mM dithiothreitol (DTT), 4 mM ATP, 5 mg/ml crude yeast tRNA, 30 µM [$^{14}C$]-leucine (9.21 µCi/ml) and 100 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic LeuRS D418A mutant leucylates $tRNA^{Leu}$ similar to the wild-type protein (FIG. 43).

Isoleucylation of $tRNA^{Leu}$ by yeast cytoplasmic LeuRS D418A was measured in a reaction containing 60 mM Tris pH 7.5, 10 mM $MgCl_2$, 1 mM dithiothreitol (DTT), 4 mM ATP, 5 mg/ml crude yeast tRNA, 22.25 µM [$^3H$]-isoleucine (200 µCi/ml) and 750 nM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS D418A protein aminoacylated $tRNA^{Leu}$ with isoleucine yielding isoleucine-$tRNA^{Leu}$ in contrast to the wild-type protein (FIG. 44).

Example 19

D418A/D419A—Eukaryotic LeuRS Mutation

In the present example compositions of leucyl-tRNA synthetase mutants described herein are made for eukaryotic organisms including, but not limited to yeast cytoplasmic LeuRS D418A/D419A.

In the present example the *S. cerevisiae* cytoplasmic LeuRS D418A/D419A mutation was introduced via the polymerase chain reaction (PCR) into the plasmid p32-AMW1 harboring yeast mutant CDC60 gene encoding the D419A mutation to create plasmid pHAPPY1-1-1-58. Expression of this gene from either plasmid yields a *S. cerevisiae* LeuRS fusion protein that contains an N-terminal six-histidine tag. The mutant CDC60 gene was amplified using 100 ng p32-AMW1 and 125 ng each of a forward and reverse primer (5'-CGT TCT AAT TCA CCA GCT GCC TAC ATT ACC ACC-3' (SEQ ID NO.:37) and 5'-GGT GGT AAT GTA GGC AGC TGG TGA ATT AGA TGG-3' (SEQ ID NO.:38), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris(hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pHAPPY1-1-1-58) was isolated using Wizard miniprep kits (Promega; Madison, Wis.). Sequencing of pHAPPY1-1-1-58 was performed by Lone Star Labs (Houston, Tex.) using a primer ycF 1356 (5'-GCT ACC AAG GGT ACT GGT GTC GTC-3') (SEQ ID NO.:32) that annealed upstream of the mutated DNA region.

Plasmid pHAPPY1-1-58 harboring yeast cytoplasmic LeuRS D418A/D419A was used to transform competent *E. coli* BL21-CodonPlus cells (Stratagene; La Jolla, Calif.). A 500 ml LB culture that included 100 µg/ml ampicillin and 34 µg/ml chloramphenicol was grown at 37° C. to an $A_{600}$ of approximately 0.6. Protein expression was induced by the addition of 1 mM isopropyl-thiogalactopyranoside (IPTG) for 30 minutes at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 2 ml bed volume of TALON affinity resin (Clontech; Palo Alto, Calif.) that had been pre-equilibrated in the cell resuspension buffer. The batch preparation for affinity purification of the yeast cytoplasmic LeuRS D418A/D419A mutant was mixed gently at 4° C. for 30 minutes. The resin was separated from the supernatant in a clinical centrifuge (International Equipment Co.; Needham Heights, Mass.). The resin was washed four times with 10 ml of 20 mM $Na_2HPO_4$ (pH 7.0), 10 mM Tris, 500 mM NaCl and 10% glycerol. The yeast cytoplasmic LeuRS D418A/D419A mutant containing a six histidine tag was eluted with 20 mM $Na_2HPO_4$ (pH 8.0), 10 mM Tris (pH 8.0), 300 mM NaCl, 100 mM imidazole and 10% glycerol. The elution fraction was concentrated and dialyzed into its final storage buffer of 20 mM $Na_2HPO_4$ (pH 8.0), 10 mM Tris, pH 7.0, 200 mM NaCl, <10 mM imidazole and 50% glycerol. The purified LeuRS fusion protein was identified by sodium dodecyl sulfate-polyacrylamide gel electrophoresis (SDS-PAGE) at about 150 kDa.

Leucylation of $tRNA^{Leu}$ by the yeast cytoplasmic LeuRS D418A/D419A mutant was measured in a reaction containing 60 mM Tris, pH 7.5, 10 mM $MgCl_2$, 1 mM dithiothreitol (DTT), 4 mM ATP, 5 mg/ml crude yeast tRNA, 30 µM [$^{14}$C]-leucine (9.21 µCi/ml) and 100 nM enzyme. The reaction was initiated by the addition of ATP. The reaction was quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The washed pads were dried and combined with 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast LeuRS. The yeast cytoplasmic LeuRS D418A/D419A mutant leucylates $tRNA^{Leu}$ similar to the wild-type protein (FIG. 45).

Figure 46:
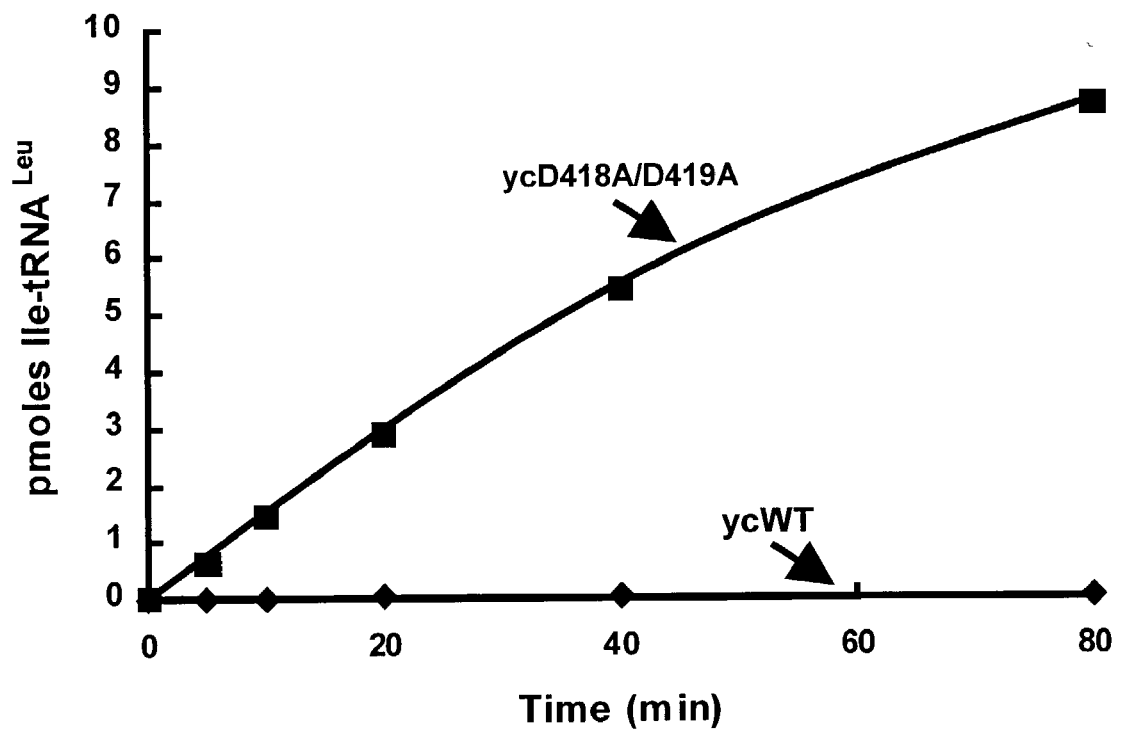
FIG. 46 is a graph of misaminoacylation of tRNA$^{Leu}$ with isoleucine by yeast cytoplasmic wild-type LeuRS and a CP1-based mutant LeuRS, wherein symbols representing aminoacylation activity by wild-type and mutant LeuRS are: wild-type (ycWT), closed diamond; ycD418A/D419A, closed square.

Isoleucylation of $tRNA^{Leu}$ by yeast cytoplasmic LeuRS D418A/D419A was measured in a reaction containing 60 mM Tris pH 7.5, 10 mM $MgCl_2$, 1 mM dithiothreitol (DTT), 4 mM ATP, 5 mg/ml crude yeast tRNA, 22.25 µM [$^{3}$H]-isoleucine (200 µCi/ml) and 750 nM enzyme. The reaction was initiated by the addition of ATP and quenched by placing a 5 µl aliquot on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from experiments performed in parallel using the wild-type yeast cytoplasmic LeuRS. The yeast cytoplasmic LeuRS D418A/D419A protein aminoacylated $tRNA^{Leu}$ with isoleucine yielding isoleucine-$tRNA^{Leu}$ in contrast to the wild-type protein (FIG. 46).

Example 20

Y330A/D342A/D345A—Eukaryotic LeuRS Mutation

Other embodiments of the present invention include leucyl-tRNA synthetase mutants described herein are made for prokaryotic organisms including, but not limited to *E. coli* LeuRS Y330A/D342A/D345A.

In the present example the *E. coli* LeuRS Y330A/D342A/D345A mutation was introduced via the polymerase chain reaction (PCR) into the plasmid pHAPPY2-1-1-29 harboring the D342A/D345A mutant *E. coli* leuS gene to create plasmid pMURet1. Expression of this gene from either plasmid yields an *E. coli* LeuRS fusion protein that contains an N-terminal six-histidine tag. The mutant leuS gene was amplified using 100 ng pMURet1 and 225 pmoles each of a forward and reverse primer (5'-CTTCGTATTGATGGAGGCCG-GCACGGGCGCAG-3' (SEQ ID NO.:24) and 5'-GAAG-CATAACTACCTCCGGCCGTGCCCGCGTC-3' (SEQ ID NO.:25), respectively) that encoded the gene mutation. The PCR reaction mixture also contained 10 nmoles each of dATP, dTTP, dGTP and dCTP, 3 units of Pfu DNA polymerase (Promega; Madison, Wis.) in 50 µl of 20 mM tris (hydroxymethyl) aminomethane (Tris), pH 8.8, 10 mM KCl, 10 mM $(NH_4)_2SO_4$, 2 mM $MgSO_4$, 0.1% Triton X-100 and 100 µg/ml bovine serum albumen (BSA). The PCR reaction was thermocycled 18 times. Each cycle was as follows: denaturation (95° C., 1 min.), annealing (60° C., 30 sec.) and extension (68° C., 20 min). The PCR products were stored at 4° C. until removal from thermocycler. Following PCR amplification, the parental plasmid was digested with 10 units of Dpn I (New England BioLabs, Inc.; Beverly, Mass.). The PCR product was then used to transform *E. coli* strain DH5α (Invitrogen Corporation; Carlsbad, Calif.). Colonies that contained the plasmid were grown and selected on LB media that contained 100 µg/ml ampicillin. The plasmid DNA (pMURet1) was isolated using Wizard miniprep kits (Promega; Madison, Wis.). Sequencing of pMURet1 was performed by Lone Star Labs (Houston, Tex.) using a primer Ecr 1582 (5'-CGGCTCTGAGCCAGATC-3') (SEQ ID NO.: 26) that annealed upstream of the mutated DNA region.

Plasmid pMURet1 harboring *E. coli* LeuRS Y330A/D342A/D345A was used to transform *E. coli* strain BL21 pLysS (Invitrogen Corporation; Carlsbad, Calif.). A 500 ml LB culture that included 100 µg/ml ampicillin was grown at 37° C. to an $A_{600}$ of approximately 0.6. Protein expression was induced by the addition of 1 mM isopropyl-thiogalactopyranoside (IPTG) for 2 hours at 25° C. The cells were recovered by centrifugation and were resuspended in 10 ml of 20 mM $Na_2HPO_4$ (pH 8.0), 10 mM Tris, 300 mM NaCl and 5% glycerol called hereafter resuspension buffer. The cells were lysed by sonication twice in a Vibra Cell (Sonics & Materials, Inc.; Danbury, Conn.) at 50% power for 1.5 minutes on ice. Cell debris was pelleted by centrifugation and discarded. The supernatant or lysate was added to a 1 ml bed volume of TALON affinity resin (Clontech; Palo Alto, Calif.) that had been pre-equilibrated in the cell resuspension buffer. The batch preparation for affinity purification of the E. coli LeuRS Y330A/D342A/D345A mutant was mixed gently at 4° C. for 30 minutes. The resin was separated from the supernatant in a clinical centrifuge (International Equipment Co.; Needham Heights, Mass.). The resin was washed four times with 10 ml of 20 mM Na$_2$HPO$_4$ (pH 7.0), 10 mM Tris, 500 mM NaCl and 10% glycerol. The E. coli LeuRS Y330A/D342A/D345A mutant containing a six-histidine tag was eluted with 20 mM Na$_2$HPO$_4$ (pH 8.0), 10 mM Tris (pH 8.0), 300 mM NaCl, 100 mM imidazole and 10% glycerol. The elution fraction was concentrated and dialyzed into its final storage buffer of 20 mM Na$_2$HPO$_4$ (pH 8.0), 10 mM Tris, pH 7.0, 200 mM NaCl, <10 mM imidazole and 50% glycerol. The purified 98.5 kDa LeuRS fusion protein was identified by sodium dodecyl sulfate-polyacrylamide gel electrophoresis (SDS-PAGE).

Preliminary studies involve the complete isolation of charged tRNA with either leucine or isoleucine. Aminoacylated tRNA$^{Leu}$ linked to leucine or isoleucine was generated in a reaction that contained 60 mM Tris (pH 7.5), 10 mM MgCl$_2$, 4 mM ATP, 1 mM DTT, 10 µM tRNA$_{UAA}^{Leu}$, 20.5 µM [$^3$H]-leucine (200 µCi/ml) or [$^3$H]-isoleucine (550 µCi/ml), and 200 nM enzyme. The reaction mixture was incubated at room temperature for 2 hours and then quenched by lowering the pH to approximately 6.0 with 0.2% acetic acid to stabilize the labile aminoacyl bond (Schreier and Schimmel, 1972; Mursinna et al., 2001; Mursinna and Martinis, 2002). The mischarged tRNA was concentrated by butanol extraction and then immediately extracted using phenol/chloroform/isoamyl alcohol (125:24:1) (pH 4.3) (Fisher Biotech, Fair Lawn, N.J.) and Eppendorf Phase Lock Gel (Brinkmann Instruments, Inc., Westbury, N.Y.), followed by ethanol precipitation. The RNA pellet was washed three times with 70% ethanol, resuspended in 20 mM potassium phosphate (pH 5.0), and stored at –20° C. To quantitate the percentage yield of charged tRNA, an aliquot of the resuspended charged tRNA was placed on a Whatman 1003323 filter pad pre-soaked in 5% (v/v) trichloroacetic acid (TCA). The pads were slowly shaken on ice in 5% TCA with four changes over a 1 hour time period. The pads were then washed with 70% ethanol and subsequently with ether (anhydrous). The pads were then dried and added to 3 ml of ScintiSafe™ Econo F scintillation solution (Fisher Scientific; Fair Lawn, N.J.). This mixture was quantitated by scintillation counting in a Beckman LS 6000IC (Beckman Instruments, Inc.; Fullerton, Calif.). Results were compared with those obtained from similar experiments performed with other mutant LeuRSs (FIGS. 47A and B). The LeuRS Y330A/D342A/D345A aminoacylates isoleucine to tRNA$^{Leu}$ at high levels, particularly compared to the levels yielded by the E. coli LeuRS D342A/D345A mutant.

Although making and using various embodiments of the present invention are discussed in detail below, it will be appreciated that the present invention provides many applicable inventive concepts that can be embodied in a wide variety of specific contexts. The specific embodiments discussed herein are merely illustrative of specific ways to make and use the invention, and do not delimit the scope of the invention.

REFERENCES

Apostol, I., J. Levine, J. Lippincott, J. Leach, E. Hess, C. B. Glascock, M. Weickert, and R. Blackmore. 1997. Incorporation of norvaline at leucine positions in recombinant human hemoglobin expressed in Escherichia coli. J Biol Chem 272: 28980-28988.

Asahara, H., H. Himeno, K. Tamura, T. Hasegawa, K. Watanabe, and M. Shimizu. 1993. Recognition nucleotides of Escherichia coli tRNA$^{Leu}$ and its elements facilitating discrimination from tRNA$^{Ser}$ and tRNA$^{Tyr}$. J. Mol. Biol. 231: 219-229.

Asahara, H., N. Nameki, and T. Hasegawa. 1998. In vitro selection of RNAs aminoacylated by Escherichia coli leucyl-tRNA synthetase. J Mol Biol 283:605-18.

Baldwin, A. N., and Berg, P. 1966. Transfer ribonucleic acid-induced hydrolysis of valyladenylate bound to isoleucyl ribonucleic acid synthetase. J Biol Chem 241, 839-845.

Chen, J. F., N. N. Guo, T. Li, E. D. Wang, and Y. L. Wang. 2000. CP1 domain in Escherichia coli leucyl-tRNA synthetase is crucial for its editing function. Biochemistry 39:6726-31.

Chen, J. F., Li, T., Wang, E. D., and Wang, Y. L. 2001. Effect of alanine-293 replacement on the activity, ATP binding, and editing of Escherichia coli leucyl-tRNA synthetase. Biochemistry 40, 1144-1149.

Cornish, V., K. Hahn, and P. Schultz. 1996. Site-specific protein modification using a ketone handle. J. Am. Chem. Soc. 118:8150-8151.

Cusack, S., A. Yaremchuk, and M. Tukalo. 2000. The 2 Å crystal structure of leucyl-tRNA synthetase and its complex with a leucyl-adenylate analogue. EMBO J 19:2351-2361.

Dietrich, A., P. Romby, L. Marechal-Drouard, P. Guillemaut, and R. Giegé. 1990. Solution conformation of several free tRNA$^{Leu}$ species from bean, yeast and Escherichia coli and interaction of these tRNAs with bean cytoplasmic leucyl-tRNA synthetase. A phosphate alkylation study with ethylnitrosourea. Nucl. Acids Res. 18:2589-2597.

Doring, V., H. D. Mootz, L. A. Nangle, T. L. Hendrickson, V. de Crecy-Lagard, P. Schimmel, and P. Marliere. 2001. Enlarging the amino acid set of Escherichia coli by infiltration of the valine coding pathway. Science 292:501-4.

Englisch, S., Englisch, U., von der Haar, F., and Cramer, F. 1986. The proofreading of hydroxy analogues of leucine and isoleucine by leucyl-tRNA synthetases from E. coli and yeast. Nucleic Acids Res 14, 7529-7539.

Fersht, A. R. 1977. Editing mechanisms in protein synthesis. Rejection of valine by the isoleucyl-tRNA synthetase. Biochemistry 16, 1025-1030.

Fukai, S., Nureki, O., Sekine, S., Shimada, A., Tao, J., Vassylyev, D. G., and Yokoyama, S. 2000. Structural basis for double-sieve discrimination of L-valine from L-isoleucine and L-threonine by the complex of tRNA(Val) and valyl-tRNA synthetase. Cell 103, 793-803.

Giegé, R., M. Sissler, and C. Florentz. 1998. Universal rules and idiosyncratic features in tRNA identity. Nucl. Acids. Res. 26:5017-35.

Heckler, T. G., L. H. Chang, Y. Zama, T. Naka, M. S. Chorghade, and S. M. Hecht. 1984. T4 RNA ligase mediated preparation of novel "chemically misacylated" tRNAPheS. Biochemistry 23:1468-73.

Hendrickson, T. L., T. K. Nomanbhoy, and P. Schimmel. 2000. Errors from selective disruption of the editing center in a tRNA synthetase. Biochemistry 39:8180-6.

Higgins, D. G., Thompson, J. D., and Gibson, T. J. 1996. Using CLUSTAL for multiple sequence alignments. Methods Enzymol 266, 383-402.

Hohmann, S. 1991. Genbank Release 710.

Hohmann, S., and Thevelein, J. M. 1992. The cell division cycle gene CDC60 encodes cytosolic leucyl-tRNA synthetase in Saccharomyces cerevisiae. Gene 120, 43-49.

Kiick, K. L., J. C. van Hest, and D. A. Tirrell. 2000. Expanding the Scope of Protein Biosynthesis by Altering the Methionyl-tRNA Synthetase Activity of a Bacterial Expression Host Angew Chem Int Ed Engl 39:2148-2152.

Kiick, K. L., R. Weberskirch, and D. A. Tirrell. 2001. Identification of an expanded set of translationally active methionine analogues in *Escherichia coli*. FEBS Lett 502:25-30.

Lee, K. W., J. M. Briggs. 2002 Molecular Modeling Study of the Editing Activity of *Escherichia coli* Leucyl-tRNA Synthetase: Two Amino Acid Binding Sites in the editing domain., Proteins: Str. Function Gen., in press.

Lee, N., and H. Suga. 2001. A minihelix-loop RNA acts as a trans-aminoacylation catalyst. Rna 7:1043-51.

Lin, L., S. P. Hale, and P. Schimmel. 1996. Aminoacylation error correction. Nature 384:33-34.

Lincecum, T. L., and S. A. Martinis. 2000. The tRNA synthetase proofreading and editing active sites: A novel antibiotic target. SAAS Bulletin Biochem. Biotech. 13:25-33.

Liu, D. R., T. J. Magliery, M. Pastmak, and P. G. Schultz. 1997a. Engineering a tRNA and aminoacyl-tRNA synthetase for the site-specific incorporation of unnatural amino acids into proteins in vivo. Proc Natl Acad Sci U S A 94:10092-7.

Liu, D. R., T. J. Magliery, and P. G. Schultz. 1997b. Characterization of an 'orthogonal' suppressor tRNA derived from *E. coli* tRNA2(Gln). Chem Biol 4:685-91.

Lohse, P. A., and J. W. Szostak. 1996. Ribozyme-catalysed amino-acid transfer reactions. Nature 381:442-4.

Martinis, S. A., and P. Schimmel. 1992. Enzymatic Aminoacylation of Sequence-Specific RNA Minihelices and Hybrid Duplexes with Methionine. Proc. Natl. Acad. Sci. U.S.A. 89:65-69.

Martinis, S. A., and P. Schimmel. 1996. Aminoacyl tRNA Synthetases: General Structures and Relationships., p. 887-901. In F. C. Neidhardt (ed.), *Escherichia coli* and Salmonella Cellular and Molecular Biology, 2nd Ed. ASM Press, Washington D.C.

Martinis, S. A., and G. E. Fox. 1997. Non-standard amino acid recognition by *Escherichia coli* leucyl-tRNA synthetase. Nucleic Acids Symp Ser 36:125-8.

Martinis, S. A., P. Plateau, J. Cavarelli, and C. Florentz. 1999a. Aminoacyl-tRNA Synthetases: A Family of Expanding Functions. EMBO J. 18:4591-4596.

Martinis, S. A., P. Plateau, J. Cavarelli, and C. Florentz. 1999b. Aminoacyl-tRNA Synthetases: A New Image for a Classical Family. Biochimie 81:683-700.

Mendel, D., V. W. Cornish, and P. G. Schultz. 1995. Site-directed mutagenesis with an expanded genetic code. Annu Rev Biophys Biomol Struct 24:435-62.

Mursinna, R. S., T. L. Lincecum, Jr., and S. A. Martinis. 2001. A conserved threonine within *Escherichia coli* leucyl-tRNA synthetase prevents hydrolytic editing of leucyl-tRNA$^{Leu}$. Biochemistry 40:5376-81.

Mursinna, R. S. and S. A. Martinis. 2002. Rational Design to Block Amino Acid Editing of a tRNA Synthetase. J. Am. Chem. Soc. 124: 7286-7287.

Niemz, A., and D. A. Tirrell. 2001. Self-association and membrane-binding behavior of melittins containing trifluoroleucine. J Am Chem Soc 123:7407-13.

Noren, C. J., S. J. Anthony-Cahill, M. C. Griffith, and P. G. Schultz. 1989. A general method for site-specific incorporation of unnatural amino acids into proteins. Science 244:182-8.

Normanly, J., R. C. Ogden, S. J. Horvath, and J. Abelson. 1986. Changing the Identity of a Transfer RNA. Nature 321: 213-219.

Norris, A. T., and Berg, P. 1964. Mechanism of aminoacyl RNA synthesis: studies with isolated aminoacyl adenylate complexes of isoleucyl RNA synthetase. Biochemistry 52: 330-337.

Nureki, O., D. G. Vassylyev, M. Tateno, A. Shimada, T. Nakama, S. Fukai, M. Konno, T. L. Hendrickson, P. Schimmel, and S. Yokoyama. 1998. Enzyme structure with two catalytic sites for double-sieve selection of substrate. Science 280:578-582.

Nureki, O., D. G. Vassylyev, M. Tateno, A. Shimada, T. Nakama, S. Fukai, M. Konno, T. L. Hendrickson, P. Schimmel, and S. Yokoyama. 1999. Proofreading by isoleucyl-tRNA synthetase: response. Science 283:453.

Payne, R. C., B. P. Nichols, and S. M. Hecht. 1987. *Escherichia coli* tryptophan synthase: synthesis of catalytically competent alpha subunit in a cell-free system containing preacylated tRNAs. Biochemistry 26:3197-205.

Rennert, O., and H. Anker. 1963. On the incorporation of 5',5',5'-trifluoroleucine into proteins of *E. coli*. Biochemistry 3:471-476.

Saito, H., and H. Suga. 2001. A Ribozyme Exclusively Aminoacylates the 3'-Hydroxyl Group of the tRNA Terminal Adenosine. J Am Chem Soc 123:7178-9.

Sampson, J. R., and Uhlenbeck, O. C. 1988. Biochemical and physical characterization of an unmodified yeast phenylalanine transfer RNA transcribed in vitro. *Proc. Natl. Acad. Sci., U.S.A.* 85, 1033-1037.

Schimmel, P., and Schmidt, E. 1995. Making connections: RNA-dependent amino acid recognition. Trends Biochem Sci 20, 1-2.

Schimmel, P., and D. Soll. 1997. When protein engineering confronts the tRNA world. Proc Natl Acad Sci USA 94:10007-9.

Sharma, N., R. Furter, P. Kast, and D. A. Tirrell. 2000. Efficient introduction of aryl bromide functionality into proteins in vivo. FEBS Lett 467:37-40.

Starzyk, R. M., T. A. Webster, and P. Schimmel. 1987. Evidence for dispensable sequences inserted into a nucleotide fold. Science 237:1614-1618.

Suga, H., J. A. Cowan, and J. W. Szostak. 1998a. Unusual metal ion catalysis in an acyl-transferase ribozyme. Biochemistry 37:10118-25.

Suga, H., P. A. Lohse, and J. W. Szostak. 1998b. Structural and kinetic characterization of an acyl transferase ribozyme. J. Am. Chem. Soc. 120:1151-1156.

Szostak, J. W. 1992. In vitro Genetics. Trends Biochem. Sci. 17:89-93.

Tang, Y., G. Ghirlanda, W. A. Petka, T. Nakajima, W. F. DeGrado, and D. A. Tirrell. 2001 a. Fluorinated Coiled-Coil Proteins Prepared In Vivo Display Enhanced Thermal and Chemical Stability This work was supported by a grant from the U.S. Army Research Office. Angew Chem Int Ed Engl 40:1494-1496.

Tang, Y., G. Ghirlanda, N. Vaidehi, J. Kua, D. T. Mainz, I. W. Goddard, W. F. DeGrado, and D. A. Tirrell. 2001b. Stabilization of coiled-coil peptide domains by introduction of trifluoroleucine. Biochemistry 40:2790-6.

Thompson, J. D., D. G. Higgins, and T. J. Gibson. 1994. CLUSTAL 2: Improving the sensitivity of progressive multiple sequence alignment through sequence weighting, positions-specific gap penalties, and weight matrix choice. Nucl. Acids Res. 22:4673-4680.

Tuerk, C., and L. Gold. 1990. Systematic Evolution of Ligands by Exponential Enrichment: RNA Ligands to Bacteriophage T4 DNA Polymerase. Science 249:505-510.

Varshney, U., C.-P. Lee, and U. L. RajBhandary. 1991. Direct Analysis of Aminoacylation Levels of tRNAs in vivo:

Application to Studying Recognition of *E. coli* Initiator tRNA Mutants by Glutaminyl-tRNA Synthetase. J. Biol. Chem. 266:24712-24718.

Wang, L., A. Brock, B. Herberich, and P. G. Schultz. 2001. Expanding the genetic cde of *Escherichia coli*. Science 292: 498-500.

What is claimed is:

1. A method for producing a mutated leucyl-tRNA synthetase that misaminoacylates non-leucine amino acids comprising the steps of:

mutating one to three amino acids in a conserved editing active site region of a connective polypeptide 1 domain of a leucyl-tRNA synthetase, wherein the conserved editing active site region is selected from the group consisting of a threonine-rich region at a position corresponding to amino acids 247 to 257 relative to the *E. coli* leucyl-tRNA synthetase numbering and a region surrounding a conserved aspartic acid corresponding to amino acid 345 including seven amino acids preceding amino acid 345 relative to the *E. coli* leucyl-tRNA synthetase numbering, and combinations thereof, wherein mutating the one to three amino acids inactivates editing activity of the leucyl-tRNA synthetase and produces a mutated leucyl-tRNA synthetase that misaminoacylates non-leucine amino acids; and aminoacylating a tRNA molecule with the mutated leucyl-tRNA synthetase in the presence of at least one non-leucine amino acid, thereby aminoacylating the non-leucine amino acid onto the tRNA molecule, wherein the non-leucine amino acid is an amino acid activated by the mutated leucyl-tRNA synthetase.

2. The method of claim 1, wherein mutating includes mutating a threonine at a position corresponding to amino acid 252 relative to the *E. coli* leucyl-tRNA synthetase numbering.

3. The method of claim 2, wherein the threonine is mutated to a phenylalanine.

4. The method of claim 2, wherein the threonine is mutated to a tyrosine.

5. The method of claim 2, wherein the threonine is mutated to an alanine.

6. The method of claim 2, wherein the threonine is mutated to a tryptophan.

7. The method of claim 1, wherein mutating includes mutating a threonine at a position corresponding to amino acid 252 relative to the *E. coli* leucyl-tRNA synthetase numbering to another amino acid and mutating an aspartic acid at a position corresponding to amino acid 342 relative to the *E. coli* leucyl-tRNA synthetase numbering to alanine.

8. The method of claim 1, wherein mutating includes mutating a threonine at a position corresponding to amino acid 252 relative to the *E. coli* leucyl-tRNA synthetase numbering to another amino acid and mutating an aspartic acid at a position corresponding to amino acid 345 relative to the *E. coli* leucyl-tRNA synthetase numbering to an alanine.

9. The method of claim 1, wherein mutating includes mutating a threonine at a position corresponding to amino acid 252 relative to the *E. coli* leucyl-tRNA synthetase numbering to an amino acid from the group consisting of alanine, tyrosine, and phenylalanine and mutating an aspartic acid at a position corresponding to amino acid 345 relative to the *E. coli* leucyl-tRNA synthetase numbering to any amino acid.

10. The method of claim 1, wherein mutating includes mutating a threonine at a position corresponding to amino acid 252 relative to the *E. coli* leucyl-tRNA synthetase numbering to an amino acid from the group consisting of alanine, tyrosine, and phenylalanine and mutating an aspartic acid at a position corresponding to amino acid 342 relative to the *E. coli* leucyl-tRNA synthetase numbering to any amino acid.

11. The method of claim 1, wherein mutating includes mutating a threonine at a position corresponding to amino acid 252 relative to the *E. coli* leucyl-tRNA synthetase numbering an aspartic acid at a position corresponding to amino acid 342 relative to the *E. coli* leucyl-tRNA synthetase numbering and mutating an aspartic acid at a position corresponding to amino acid 345 relative to the *E. coli* leucyl-tRNA synthetase numbering to alanine.

12. The method of claim 1, wherein mutating includes mutating a threonine at a position corresponding to amino acid 252 relative to the *E. coli* leucyl-tRNA synthetase numbering an aspartic acid at a position corresponding to amino acid 342 relative to the *E. coli* leucyl-tRNA synthetase numbering and mutating an aspartic acid at a position corresponding to amino acid 345 relative to the *E. coli* leucyl-tRNA synthetase numbering to any amino acid.

13. A mutated leucyl-tRNA synthetase for aminoacylating at least one non-leucine amino acid onto a tRNA molecule comprising:

mutated leucyl tRNA synthetase having one to three amino acids mutated in a conserved editing active site region of a connective polypeptide 1 domain of leucyl tRNA synthetase, wherein the conserved editing active site region is selected from the group consisting of a threonine-rich region at a position corresponding to amino acids 247 to 257 relative to *E. coli* leucyl-tRNA synthetase numbering and a region surrounding a conserved aspartic acid corresponding to amino acid 345 including seven amino acids preceding amino acid 345 relative to the *E. coli* leucyl-tRNA synthetase numbering and combinations thereof, wherein mutation of the one to three amino acids inactivates editing activity of the mutated leucyl tRNA synthetase.

14. A method for aminoacylating non-leucine amino acids onto tRNA molecules comprising the steps of:

mutating one to three amino acids in a conserved editing active site region of a connective polypeptide 1 domain of a leucyl-tRNA synthetase, wherein the conserved editing active site region is selected from the group consisting of a threonine-rich region at a position corresponding to amino acids 247 to 257 relative to the *E. coli* leucyl-tRNA synthetase numbering and a region surrounding a conserved aspartic acid corresponding to amino acid 345 including seven amino acids preceding amino acid 345 relative to the *E. coli* leucyl-tRNA synthetase numbering, and combinations thereof, wherein mutating the one to three amino acids inactivates editing activity of the leucyl-tRNA synthetase and produces a mutated leucyl-tRNA synthetase that misaminoacylates non-leucine amino acids; and aminoacylating a tRNA molecule with the mutated leucyl-tRNA synthetase in the presence of at least one non-leucine amino acid, thereby aminoacylating the non-leucine amino acid onto the tRNA molecule, wherein the non-leucine amino acid is an amino acid activated by the mutated leucyl-tRNA synthetase.

15. A mutated leucyl-tRNA synthetase for incorporating at least one non-leucine amino acid onto a tRNA molecule comprising:

a mutated leucyl tRNA synthetase having one to three amino acids mutated in a conserved editing active site region of a connective polypeptide 1 domain of leucyl tRNA synthetase, wherein the conserved editing active site region is selected from the group consisting of a threonine-rich region at a position corresponding to amino acids 247 to 257 relative to the *E. coil* leucyl-tRNA synthetase numbering and a region surrounding a conserved aspartic acid corresponding to amino acid 345 including seven amino acids preceding amino acid 345 relative to the *E. coil* leucyl-tRNA synthetase numbering, and combinations thereof, wherein mutation of the one to three amino acids inactivates editing activity of the mutated leucyl tRNA synthetase and produces a mutated leucyl-tRNA synthetase that misaminoacylates non-leucine amino acids.

16. The mutated leucyl-tRNA synthetase of claim 13, wherein the mutated leucyl-tRNA synthetase has altered specificity for a cognate amino acid.

17. The mutated leucyl-tRNA synthetase of claim 13, wherein the mutated leucyl-tRNA synthetase has altered specificity for a non-leucine amino acid.

18. The mutated leucyl-tRNA synthetase of claim 15, wherein the mutated leucyl-tRNA synthetase has altered specificity for a cognate amino acid.

19. The method of claim 14, wherein mutating includes mutating an aspartic acid to an alanine at a position corresponding to position 345 relative to the *E. coli* leucyl-tRNA synthetase numbering.

20. The method of claim 14, wherein mutating includes mutating an aspartic acid to any amino acid at a position corresponding to position 345 relative to the *E. coli* leucyl-tRNA synthetase numbering.

21. The method of claim 14, wherein mutating includes mutating an aspartic acid to any amino acid at a position corresponding to amino acid position 342 relative to the *E. coli* leucyl -tRNA synthetase numbering.

22. The method of claim 14, wherein mutating includes mutating an aspartic acid at a position corresponding to amino acid position 342 relative to the *E. coli* leucyl-tRNA synthetase numbering and an aspartic acid to alanine at a position corresponding to amino acid 345 relative to the *E. coli* leucyl-tRNA synthetase numbering.

23. The method of claim 14, wherein mutating includes mutating an aspartic acid at a position corresponding to amino acid position 342 relative to the *E. coli* leucyl-tRNA synthetase numbering and an aspartic acid at a position corresponding to amino acid 345 relative to the *E. coli* leucyl-tRNA synthetase numbering to any amino acid.

24. The mutated leucyl-tRNA synthetase of claim 13, wherein the mutated leucyl tRNA synthetase aminoacylates the non-leucine amino acids on a tRNA molecule.

25. A mutated leucyl-tRNA synthetase for aminoacylating at least one non-leucine amino acid onto a tRNA molecule comprising:

a mutated leucyl tRNA synthetase having one to three amino acids mutated in a conserved editing active site region of a connective polypeptide 1 domain of leucyl tRNA synthetase, wherein the conserved editing active site region is selected from the group consisting of a threonine-rich region at a position corresponding to amino acids 247 to 257 relative to the *E. coli* leucvl-tRNA synthetase numbering and a region surrounding a conserved aspartic acid corresponding to amino acid 345 including seven amino acids preceding amino acid 345 relative to the *E. coli* leucyl-tRNA synthetase numbering, and combinations thereof, wherein mutation of the one to three amino acids inactivates editing activity of the mutated leucyl tRNA synthetase and produces a mutated leucyl-tRNA synthetase that misaminoacylates non-leucine amino acids.

26. The mutated leucyl-tRNA synthetase of claim 25, wherein the mutated leucyl-tRNA synthetase has altered specificity for a cognate amino acid.

27. The mutated leucyl-tRNA synthetase of claim 25, wherein the mutated leucyl-tRNA synthetase has altered specificity for a non-leucine amino acid.

28. The mutated leucyl-tRNA synthetase of claim 25, wherein the mutated leucyl tRNA synthetase is from the group consisting of a derivative, natural, synthetic analog, engineered enzyme, mimetic, single mutant, multiple mutant, mutant with deletions, chimeric molecule, versions that are cognate to other amino acids, and combinations thereof 29. The mutated leucyl-tRNA synthetase of claim 25, wherein the mutated leucyl tRNA synthetase incorporates the non-leucine amino acids on a tRNA molecule.

\* \* \* \* \*